(12) United States Patent
Erbey, II et al.

(10) Patent No.: US 11,752,300 B2
(45) Date of Patent: *Sep. 12, 2023

(54) CATHETER DEVICE AND METHOD FOR INDUCING NEGATIVE PRESSURE IN A PATIENT'S BLADDER

(71) Applicant: Roivios Limited, Nassau (BS)

(72) Inventors: John R. Erbey, II, Milton, GA (US);
Jacob L. Upperco, Atlanta, GA (US);
David E. Orr, Piedmont, SC (US);
Andrew Wilbourn, Crestwood, KY (US); Daisy Smith, Marietta, GA (US);
Colin Huber, Roswell, GA (US);
Morgan Hinchey, Woodstock, GA (US)

(73) Assignee: Roivios Limited, Nassau (BS)

(*) Notice: Subject to any disclaimer, the term of this patent is extended or adjusted under 35 U.S.C. 154(b) by 239 days.

This patent is subject to a terminal disclaimer.

(21) Appl. No.: 17/089,757

(22) Filed: Nov. 5, 2020

(65) Prior Publication Data

US 2021/0046278 A1  Feb. 18, 2021

Related U.S. Application Data

(63) Continuation of application No. 15/879,869, filed on Jan. 25, 2018, now Pat. No. 10,918,827, which is a
(Continued)

(51) Int. Cl.
*A61M 25/00* (2006.01)
*A61B 5/20* (2006.01)
*A61B 5/00* (2006.01)

(52) U.S. Cl.
CPC ............ *A61M 25/003* (2013.01); *A61B 5/205* (2013.01); *A61M 25/0017* (2013.01); *A61B 5/6852* (2013.01); *A61M 2210/1085* (2013.01)

(58) Field of Classification Search
CPC ............ A61M 27/008; A61M 25/0017; A61M 25/04; A61M 25/007; A61M 2210/1085;
(Continued)

(56) References Cited

U.S. PATENT DOCUMENTS 1,870,942 A  8/1932  Beatty
2,285,980 A  6/1942  Jeckel
(Continued)

FOREIGN PATENT DOCUMENTS

AU  2013332448 A1  4/2015
CA     1243581 A  10/1988
(Continued)

OTHER PUBLICATIONS

Bart et al.; "Ultrafiltration in Decompensated Heart Failure with Cardiorenal Syndrome"; N Engl J Med; 2012; p. 2296-2304; vol. 367.
(Continued)

*Primary Examiner* — Adam Marcetich
(74) *Attorney, Agent, or Firm* — THE WEBB LAW FIRM

(57) ABSTRACT

A catheter includes an elongated tube having a distal portion having a distal end and a sidewall defining at least one drainage lumen. The catheter also includes a permeable material. The permeable material is configured to be deployed in the urinary tract to maintain the distal end of the elongated tube at a predetermined position in a bladder, a ureter, a renal pelvis, or a kidney of the patient. When deployed, the permeable material defines a three-dimensional shape of sufficient size to permit flow of at least a portion of fluid from the urinary tract through the permeable material and the at least one drainage lumen.

22 Claims, 24 Drawing Sheets

Related U.S. Application Data continuation-in-part of application No. 15/687,064, filed on Aug. 25, 2017, now Pat. No. 10,765,834, which is a continuation-in-part of application No. 15/411,884, filed on Jan. 20, 2017, now Pat. No. 10,512,713, which is a continuation-in-part of application No. 15/214,955, filed on Jul. 20, 2016, now Pat. No. 10,307,564, said application No. 15/879,869 is a continuation-in-part of application No. 15/687,083, filed on Aug. 25, 2017, now Pat. No. 10,926,062, which is a continuation-in-part of application No. 15/411,884, filed on Jan. 20, 2017, now Pat. No. 10,512,713, which is a continuation-in-part of application No. 15/214,955, filed on Jul. 20, 2016, now Pat. No. 10,307,564, said application No. 15/879,869 is a continuation-in-part of application No. 15/745,823, filed as application No. PCT/US2016/043101 on Jul. 20, 2016, now abandoned.

(60) Provisional application No. 62/300,025, filed on Feb. 25, 2016, provisional application No. 62/278,721, filed on Jan. 14, 2016, provisional application No. 62/260,966, filed on Nov. 30, 2015, provisional application No. 62/194,585, filed on Jul. 20, 2015, provisional application No. 62/489,789, filed on Apr. 25, 2017, provisional application No. 62/489,831, filed on Apr. 25, 2017.

(58) Field of Classification Search
CPC ...... A61M 25/0068; A61M 2210/1089; A61M 2202/0496; A61M 2210/1082; A61M 2210/1078; A61F 2/04; A61F 2002/048; A61F 2/042; A61F 2002/047; A61F 2/82; A61F 2/94; A61F 2230/0067; A61F 2230/0093; A61B 5/208; A61B 5/201
See application file for complete search history.

(56) References Cited

U.S. PATENT DOCUMENTS

| | | |
|---|---|---|
| 2,649,092 A | 8/1953 | Wallace |
| 3,108,595 A | 10/1963 | Overment |
| 3,397,699 A | 8/1968 | Kohl |
| 3,561,431 A | 2/1971 | Pannier, Jr. |
| 3,707,967 A | 1/1973 | Kitrilakis |
| 3,875,941 A | 4/1975 | Adair |
| 3,938,529 A | 2/1976 | Gibbons |
| 3,938,530 A | 2/1976 | Santomier |
| 3,943,929 A | 3/1976 | Patel |
| 4,265,243 A | 5/1981 | Taylor |
| 4,306,557 A | 12/1981 | North |
| 4,324,663 A | 4/1982 | Hirel et al. |
| 4,349,029 A | 9/1982 | Mott |
| 4,425,124 A | 1/1984 | Womack |
| 4,437,856 A | 3/1984 | Valli |
| 4,531,933 A | 7/1985 | Norton et al. |
| 4,568,338 A | 2/1986 | Todd |
| 4,571,241 A | 2/1986 | Christopher |
| 4,575,371 A | 3/1986 | Nordqvist et al. |
| 4,629,015 A | 12/1986 | Fried et al. |
| 4,681,564 A | 7/1987 | Landreneau |
| 4,710,169 A | 12/1987 | Christopher |
| 4,738,667 A | 4/1988 | Galloway |
| 4,813,935 A | 3/1989 | Haber et al. |
| 4,834,724 A | 5/1989 | Geiss et al. |
| 4,932,938 A | 6/1990 | Goldberg et al. |
| 4,935,004 A | 6/1990 | Cruz |
| 4,945,895 A | 8/1990 | Takai et al. |
| 4,950,228 A | 8/1990 | Knapp, Jr. et al. |
| 4,957,479 A | 9/1990 | Roemer |
| 5,009,639 A | 4/1991 | Keymling |
| 5,011,488 A | 4/1991 | Ginsburg |
| 5,041,093 A | 8/1991 | Chu |
| 5,044,902 A | 9/1991 | Malbec |
| 5,059,169 A | 10/1991 | Zilber |
| 5,078,684 A | 1/1992 | Yasuda |
| 5,098,440 A | 3/1992 | Hillstead |
| 5,116,309 A | 5/1992 | Coll |
| 5,141,502 A | 8/1992 | Macaluso, Jr. |
| 5,193,533 A | 3/1993 | Body et al. |
| 5,256,146 A | 10/1993 | Ensminger et al. |
| 5,370,690 A | 12/1994 | Barrett |
| 5,401,257 A | 3/1995 | Chevalier, Jr. et al. |
| 5,451,215 A | 9/1995 | Wolter |
| 5,451,218 A | 9/1995 | Moore |
| 5,505,717 A | 4/1996 | Moore |
| 5,514,112 A | 5/1996 | Chu et al. |
| 5,523,092 A | 6/1996 | Hanson et al. |
| 5,536,274 A | 7/1996 | Neuss |
| 5,540,701 A | 7/1996 | Sharkey |
| 5,554,144 A | 9/1996 | Wallace et al. |
| 5,562,622 A | 10/1996 | Tihon |
| 5,599,291 A | 2/1997 | Balbierz et al. |
| 5,647,843 A | 7/1997 | Mesrobian et al. |
| 5,662,713 A | 9/1997 | Andersen et al. |
| 5,709,874 A | 1/1998 | Hanson et al. |
| 5,727,555 A | 3/1998 | Chait |
| 5,762,599 A | 6/1998 | Sohn |
| 5,769,821 A | 6/1998 | Abrahamson et al. |
| 5,785,641 A | 7/1998 | Davis |
| 5,795,319 A | 8/1998 | Ali |
| 5,865,764 A | 2/1999 | Moorhead |
| 5,873,865 A | 2/1999 | Horzewski et al. |
| 5,895,398 A | 4/1999 | Wensel et al. |
| 5,902,336 A | 5/1999 | Mishkin |
| 5,915,386 A | 6/1999 | Lloyd et al. |
| 5,957,867 A | 9/1999 | Lloyd et al. |
| 5,972,019 A | 10/1999 | Engelson et al. |
| 5,989,207 A | 11/1999 | Hughes |
| 6,066,113 A | 5/2000 | Overtoom |
| 6,090,069 A | 7/2000 | Walker |
| 6,111,520 A | 8/2000 | Allen et al. |
| 6,200,485 B1 | 3/2001 | Kitaevich et al. |
| 6,214,037 B1 | 4/2001 | Mitchell et al. |
| 6,283,940 B1 | 9/2001 | Mulholland |
| 6,332,892 B1 | 12/2001 | Desmond, III et al. |
| 6,364,868 B1 | 4/2002 | Ikeguchi |
| 6,402,736 B1 | 6/2002 | Brown et al. |
| 6,442,415 B1 | 8/2002 | Bis et al. |
| 6,461,346 B1 | 10/2002 | Buelna |
| 6,478,778 B1 | 11/2002 | Jacobsen et al. |
| 6,482,222 B1 | 11/2002 | Bruckheimer et al. |
| 6,500,158 B1 | 12/2002 | Ikeguchi |
| 6,558,350 B1 | 5/2003 | Hart et al. |
| 6,569,150 B2 | 5/2003 | Teague et al. |
| 6,620,202 B2 | 9/2003 | Bottcher et al. |
| 6,648,863 B2 | 11/2003 | Reever |
| 6,676,623 B2 | 1/2004 | Whitmore, III |
| 6,685,744 B2 | 2/2004 | Gellman et al. |
| 6,702,834 B1 | 3/2004 | Boylan et al. |
| 6,764,519 B2 | 7/2004 | Whitmore, III |
| 6,780,322 B1 | 8/2004 | Bissler et al. |
| 6,837,868 B1 | 1/2005 | Fajnszlajn |
| 7,025,753 B2 | 4/2006 | Reever |
| 7,037,345 B2 | 5/2006 | Bottcher et al. |
| 7,044,981 B2 | 5/2006 | Liu et al. |
| 7,316,663 B2 | 1/2008 | Whitmore, III |
| 7,329,226 B1 | 2/2008 | Ni et al. |
| 7,396,366 B2 | 7/2008 | Ward |
| 7,507,218 B2 | 3/2009 | Aliski et al. |
| 7,550,978 B2 | 6/2009 | Joy et al. |
| 7,603,170 B2 | 10/2009 | Hatlestad et al. |
| 7,682,401 B2 | 3/2010 | Deal |
| 7,722,677 B2 | 5/2010 | Ward |
| 7,727,222 B2 | 6/2010 | Da Silva et al. |
| 7,736,354 B2 | 6/2010 | Gelfand et al. |
| 7,758,562 B2 | 7/2010 | Gelfand et al. |
| 7,758,563 B2 | 7/2010 | Gelfand et al. |
| 7,766,961 B2 | 8/2010 | Patel et al. |
| 7,837,667 B2 | 11/2010 | Gelfand et al. |

(56) References Cited

U.S. PATENT DOCUMENTS

| | | |
|---|---|---|
| 7,850,704 B2 | 12/2010 | Burnett et al. |
| 7,857,803 B1 | 12/2010 | Salinas et al. |
| 7,879,020 B1 | 2/2011 | Salinas et al. |
| 7,938,817 B2 | 5/2011 | Gelfand et al. |
| 7,972,292 B2 | 7/2011 | Behl et al. |
| 8,007,460 B2 | 8/2011 | Gelfand et al. |
| 8,021,307 B2 | 9/2011 | White et al. |
| 8,075,513 B2 | 12/2011 | Rudko et al. |
| 8,088,170 B2 | 1/2012 | Whitmore, III |
| 8,105,317 B2 | 1/2012 | Reever et al. |
| 8,152,786 B2 | 4/2012 | Shapland et al. |
| 8,157,785 B2 | 4/2012 | Salinas et al. |
| 8,177,741 B2 | 5/2012 | Hammack et al. |
| 8,252,065 B2 | 8/2012 | Ward |
| 8,328,877 B2 | 12/2012 | Gellman |
| 8,444,623 B2 | 5/2013 | Gelfand et al. |
| 8,486,010 B2 | 7/2013 | Nomura |
| 8,512,795 B2 | 8/2013 | Dias et al. |
| 8,568,387 B2 | 10/2013 | Paz |
| 8,585,675 B2 | 11/2013 | Salinas et al. |
| 8,597,260 B2 | 12/2013 | Tucker |
| 8,597,273 B2 | 12/2013 | Salinas et al. |
| 8,747,388 B2 | 6/2014 | Pandey et al. |
| 8,795,305 B2 | 8/2014 | Martin et al. |
| 8,827,924 B2 | 9/2014 | Paz et al. |
| 8,852,289 B2 | 10/2014 | Whitmore, III |
| 8,865,063 B2 | 10/2014 | Burnett |
| 9,014,815 B2 | 4/2015 | Yang et al. |
| 9,060,888 B2 | 6/2015 | Gellman |
| 9,308,348 B2 | 4/2016 | Mulvihill et al. |
| 9,339,636 B1 | 5/2016 | Khan et al. |
| 9,682,220 B2 | 6/2017 | Schertiger et al. |
| 9,744,331 B2 | 8/2017 | Erbey, II et al. |
| 9,750,634 B2 | 9/2017 | Bar-Am |
| 9,788,928 B2 | 10/2017 | Forsell |
| 9,849,224 B2 | 12/2017 | Angwin et al. |
| 9,980,663 B2 | 5/2018 | Wabel et al. |
| 10,182,747 B2 | 1/2019 | Charlez et al. |
| 10,226,606 B2 | 3/2019 | Wan et al. |
| 10,307,566 B2 | 6/2019 | Bishawi |
| 10,449,329 B2 | 10/2019 | Foley et al. |
| 11,040,180 B2 | 6/2021 | Erbey, II et al. |
| 2001/0053936 A1 | 12/2001 | Whitmore, III |
| 2001/0056273 A1* | 12/2001 | C. ............... A61M 25/04 604/509 |
| 2002/0052576 A1 | 5/2002 | Massengale |
| 2002/0062148 A1 | 5/2002 | Hart |
| 2002/0068093 A1 | 6/2002 | Trogolo et al. |
| 2002/0082547 A1 | 6/2002 | Deniega et al. |
| 2002/0085951 A1 | 7/2002 | Gelfand et al. |
| 2002/0143292 A1 | 10/2002 | Flinchbaugh |
| 2002/0143389 A1 | 10/2002 | St. Pierre |
| 2002/0177902 A1 | 11/2002 | Rioux et al. |
| 2002/0183852 A1 | 12/2002 | McWeeney |
| 2002/0183853 A1 | 12/2002 | Mitchell et al. |
| 2002/0188246 A1 | 12/2002 | Hayner et al. |
| 2002/0193667 A1 | 12/2002 | McNair |
| 2003/0009132 A1 | 1/2003 | Schwartz et al. |
| 2003/0018291 A1 | 1/2003 | Hill et al. |
| 2003/0060806 A1 | 3/2003 | Ikeguchi |
| 2003/0069534 A1 | 4/2003 | Work et al. |
| 2003/0074082 A1 | 4/2003 | Bottcher et al. |
| 2003/0109930 A1 | 6/2003 | Bluni et al. |
| 2003/0120261 A1 | 6/2003 | Gellman |
| 2003/0135147 A1 | 7/2003 | Rosenberg et al. |
| 2003/0135195 A1 | 7/2003 | Jimenez et al. |
| 2003/0144623 A1 | 7/2003 | Heath et al. |
| 2003/0153970 A1 | 8/2003 | Rao et al. |
| 2003/0171708 A1 | 9/2003 | Segura et al. |
| 2003/0176831 A1 | 9/2003 | Gellman et al. |
| 2003/0181842 A1 | 9/2003 | Gellman |
| 2003/0181887 A1 | 9/2003 | Castillo Deniega et al. |
| 2003/0191452 A1 | 10/2003 | Meglin et al. |
| 2003/0195456 A1 | 10/2003 | Robertson |
| 2003/0195537 A1* | 10/2003 | Dubrul ............... A61B 17/221 606/159 |
| 2003/0199805 A1 | 10/2003 | McWeeney |
| 2003/0216710 A1 | 11/2003 | Hurt |
| 2003/0224033 A1 | 12/2003 | Li et al. |
| 2004/0019358 A1 | 1/2004 | Kear |
| 2004/0054315 A1 | 3/2004 | Levin et al. |
| 2004/0054351 A1 | 3/2004 | Deniega et al. |
| 2004/0057037 A1 | 3/2004 | Ohishi et al. |
| 2004/0073194 A1 | 4/2004 | Olsen et al. |
| 2004/0097891 A1 | 5/2004 | Bolmsjo |
| 2004/0129616 A1 | 7/2004 | Mori et al. |
| 2004/0143209 A1 | 7/2004 | Liu et al. |
| 2004/0147871 A1 | 7/2004 | Burnett |
| 2004/0167415 A1 | 8/2004 | Gelfand et al. |
| 2004/0167634 A1 | 8/2004 | Atala et al. |
| 2004/0193098 A1 | 9/2004 | Wentling et al. |
| 2005/0042240 A1 | 2/2005 | Utterberg et al. |
| 2005/0049575 A1* | 3/2005 | Snell ............... A61M 25/04 604/544 |
| 2005/0049577 A1 | 3/2005 | Snell et al. |
| 2005/0101941 A1 | 5/2005 | Hakky et al. |
| 2005/0107736 A1 | 5/2005 | Landman et al. |
| 2005/0124969 A1 | 6/2005 | Fitzgerald et al. |
| 2005/0124978 A1 | 6/2005 | Kim |
| 2005/0177102 A1 | 8/2005 | Hart et al. |
| 2005/0187564 A1 | 8/2005 | Jayaraman |
| 2005/0240141 A1 | 10/2005 | Aliski et al. |
| 2005/0240280 A1 | 10/2005 | Aliski et al. |
| 2005/0256441 A1 | 11/2005 | Lotan et al. |
| 2005/0256447 A1 | 11/2005 | Richardson et al. |
| 2005/0288722 A1 | 12/2005 | Eigler et al. |
| 2006/0015015 A1 | 1/2006 | Kawamoto et al. |
| 2006/0015089 A1 | 1/2006 | Meglin et al. |
| 2006/0052879 A1 | 3/2006 | Kolb |
| 2006/0074388 A1 | 4/2006 | Dextradeur et al. |
| 2006/0074409 A1 | 10/2006 | Schuermann |
| 2006/0229553 A1 | 10/2006 | Hammack et al. |
| 2006/0229573 A1 | 10/2006 | Lamborne |
| 2006/0259151 A1 | 11/2006 | Ward |
| 2006/0271019 A1 | 11/2006 | Stoller et al. |
| 2007/0010797 A1 | 1/2007 | Nishtala et al. |
| 2007/0010798 A1 | 1/2007 | Stoller et al. |
| 2007/0055198 A1 | 3/2007 | O'Mahony et al. |
| 2007/0073271 A1 | 3/2007 | Brucker et al. |
| 2007/0088333 A1 | 4/2007 | Levin et al. |
| 2007/0112302 A1 | 5/2007 | Yu |
| 2007/0197957 A1 | 8/2007 | Hunter et al. |
| 2007/0208291 A1 | 9/2007 | Patel |
| 2007/0219488 A1 | 9/2007 | Francescatti |
| 2007/0255230 A1 | 11/2007 | Gross et al. |
| 2008/0051678 A1 | 2/2008 | Lindahl |
| 2008/0051691 A1 | 2/2008 | Dragoon et al. |
| 2008/0058650 A1 | 3/2008 | Saadat et al. |
| 2008/0097463 A1 | 4/2008 | House |
| 2008/0119907 A1 | 5/2008 | Stahmann |
| 2008/0142023 A1 | 6/2008 | Schmid et al. |
| 2008/0183299 A1 | 7/2008 | Monga et al. |
| 2008/0243091 A1 | 10/2008 | Humphreys et al. |
| 2008/0255550 A1 | 10/2008 | Bell |
| 2008/0281291 A1 | 11/2008 | Tihon et al. |
| 2008/0288082 A1 | 11/2008 | Deal |
| 2008/0312550 A1 | 12/2008 | Nishtala et al. |
| 2009/0024091 A1 | 1/2009 | Li et al. |
| 2009/0030370 A1 | 1/2009 | Nishtala et al. |
| 2009/0030435 A1 | 1/2009 | Burnett et al. |
| 2009/0043229 A1 | 2/2009 | Dunn et al. |
| 2009/0088677 A1 | 4/2009 | Cohen |
| 2009/0093748 A1 | 4/2009 | Patterson et al. |
| 2009/0105719 A1 | 4/2009 | Honey et al. |
| 2009/0143713 A1 | 6/2009 | Van Dam et al. |
| 2009/0162530 A1 | 6/2009 | Nesbitt |
| 2009/0171137 A1 | 7/2009 | Farnan et al. |
| 2009/0171241 A1 | 7/2009 | Garcia et al. |
| 2009/0281507 A1 | 11/2009 | Humphreys |
| 2009/0318844 A1 | 12/2009 | Burnett |
| 2010/0057000 A1* | 3/2010 | Melsheimer ............ D03D 3/02 139/420 A |
| 2010/0081148 A1 | 4/2010 | Singbartl et al. |

(56) References Cited

U.S. PATENT DOCUMENTS

| | | |
|---|---|---|
| 2010/0086580 A1 | 4/2010 | Nyman et al. |
| 2010/0121159 A1 | 5/2010 | Burnett et al. |
| 2010/0191183 A1 | 7/2010 | Fanghoej et al. |
| 2010/0204682 A1 | 8/2010 | Tanghoj et al. |
| 2010/0241240 A1 | 9/2010 | Willard et al. |
| 2010/0261985 A1 | 10/2010 | Cohen-Solal et al. |
| 2010/0298857 A1 | 11/2010 | Zook et al. |
| 2010/0312163 A1 | 12/2010 | Forsell |
| 2011/0009799 A1 | 1/2011 | Mullick et al. |
| 2011/0009831 A1 | 1/2011 | Burkholz et al. |
| 2011/0015558 A1 | 1/2011 | Kaye et al. |
| 2011/0089111 A1 | 4/2011 | Mori et al. |
| 2011/0098683 A1 | 4/2011 | Wiita et al. |
| 2011/0118537 A1 | 5/2011 | Wampler |
| 2011/0132838 A1 | 6/2011 | Curtis et al. |
| 2011/0208319 A1 | 8/2011 | Laster |
| 2011/0230950 A1 | 9/2011 | Knapp |
| 2011/0238163 A1 | 9/2011 | Andrews et al. |
| 2011/0269167 A1 | 11/2011 | Bene |
| 2011/0276024 A1 | 11/2011 | Randolph et al. |
| 2011/0282264 A1 | 11/2011 | Hurt |
| 2011/0301553 A1 | 12/2011 | Goral et al. |
| 2011/0301662 A1 | 12/2011 | Bar-Yoseph et al. |
| 2011/0320008 A1 | 12/2011 | Teague et al. |
| 2012/0029937 A1 | 2/2012 | Neftel et al. |
| 2012/0042427 A1 | 2/2012 | Messier |
| 2012/0053700 A1 | 3/2012 | Rickner |
| 2012/0078226 A1 | 3/2012 | Latere Dwan'isa et al. |
| 2012/0083899 A1 | 4/2012 | Whitmore, III |
| 2012/0107420 A1 | 5/2012 | Breit et al. |
| 2012/0136343 A1 | 5/2012 | Burnett |
| 2012/0154264 A1 | 6/2012 | Wang et al. |
| 2012/0165641 A1 | 6/2012 | Burnett et al. |
| 2012/0179144 A1 | 7/2012 | Carleo |
| 2012/0179145 A1 | 7/2012 | Nishtala et al. |
| 2012/0220926 A1 | 8/2012 | Soykan et al. |
| 2012/0238802 A1 | 9/2012 | Knight et al. |
| 2012/0265020 A1 | 10/2012 | Pandey et al. |
| 2012/0277155 A1 | 11/2012 | VanAntwerp et al. |
| 2012/0316656 A1 | 12/2012 | Deal et al. |
| 2013/0030262 A1 | 1/2013 | Burnett et al. |
| 2013/0066166 A1 | 3/2013 | Burnett et al. |
| 2013/0085468 A1 | 4/2013 | Buydenok |
| 2013/0090648 A1 | 4/2013 | Nagale et al. |
| 2013/0131621 A1 | 5/2013 | Van Holten et al. |
| 2013/0138077 A1 | 5/2013 | O'Day |
| 2013/0150828 A1 | 6/2013 | Conway |
| 2013/0172807 A1 | 7/2013 | Cruz |
| 2013/0172881 A1 | 7/2013 | Hill et al. |
| 2013/0184545 A1 | 7/2013 | Blomqvist et al. |
| 2013/0187563 A1 | 7/2013 | Sasai et al. |
| 2013/0197471 A1 | 8/2013 | Williams et al. |
| 2013/0199998 A1 | 8/2013 | Kelly et al. |
| 2013/0218135 A1 | 8/2013 | Dein |
| 2013/0231640 A1 | 9/2013 | Terry et al. |
| 2013/0231752 A1 | 9/2013 | Rosenbaum et al. |
| 2013/0253409 A1 | 9/2013 | Burnett |
| 2013/0267845 A1 | 10/2013 | Howle et al. |
| 2013/0274644 A1 | 10/2013 | Hertz |
| 2013/0274783 A1 | 10/2013 | Wynberg |
| 2013/0303865 A1 | 11/2013 | Rebec et al. |
| 2013/0303961 A1 | 11/2013 | Wolff et al. |
| 2013/0304082 A1 | 11/2013 | Aklog et al. |
| 2013/0317322 A1 | 11/2013 | Andrijauskas |
| 2013/0331824 A1 | 12/2013 | Kim |
| 2013/0338580 A1 | 12/2013 | Yamatani et al. |
| 2013/0345670 A1 | 12/2013 | Rajagopalan et al. |
| 2014/0031773 A1 | 1/2014 | Mikkaichi |
| 2014/0031787 A1 | 1/2014 | Burnes et al. |
| 2014/0039375 A1 | 2/2014 | Jimenez et al. |
| 2014/0058316 A1 | 2/2014 | Gupta et al. |
| 2014/0073926 A1 | 3/2014 | Rajendran et al. |
| 2014/0074144 A1* | 3/2014 | Shrivastava ......... A61B 17/221 |
| | | 606/200 |
| 2014/0135941 A1 | 5/2014 | Smouse et al. |
| 2014/0142539 A1 | 5/2014 | Salinas et al. |
| 2014/0148648 A1 | 5/2014 | Tycast et al. |
| 2014/0148754 A1 | 5/2014 | Soykan et al. |
| 2014/0155818 A1 | 6/2014 | Salinas et al. |
| 2014/0188248 A1 | 7/2014 | Gandhi |
| 2014/0214009 A1 | 7/2014 | Reyes |
| 2014/0228801 A1 | 8/2014 | Keeling |
| 2014/0275984 A1 | 9/2014 | Hermann et al. |
| 2014/0276341 A1 | 9/2014 | Ludin et al. |
| 2014/0276628 A1 | 9/2014 | Gandras et al. |
| 2014/0364820 A1 | 12/2014 | Solazzo et al. |
| 2015/0011855 A1 | 1/2015 | Burnett et al. |
| 2015/0011928 A1 | 1/2015 | Burnett |
| 2015/0017682 A1 | 1/2015 | Adam |
| 2015/0080844 A1 | 3/2015 | Donovan et al. |
| 2015/0094548 A1 | 4/2015 | Sabatini et al. |
| 2015/0094696 A1 | 4/2015 | Adams, Jr. et al. |
| 2015/0100009 A1 | 4/2015 | Bearss |
| 2015/0134073 A1 | 5/2015 | Tang et al. |
| 2015/0164370 A1 | 6/2015 | Wabel et al. |
| 2015/0194052 A1 | 7/2015 | Sagan et al. |
| 2015/0223953 A1 | 8/2015 | Pendleton et al. |
| 2015/0224241 A1 | 8/2015 | Fontanazzi et al. |
| 2015/0273120 A1 | 10/2015 | Zamarripa et al. |
| 2015/0283362 A1 | 10/2015 | Shelton et al. |
| 2015/0290411 A1 | 10/2015 | Warrington et al. |
| 2015/0306364 A1 | 10/2015 | Shevgoor |
| 2015/0328027 A1 | 11/2015 | Nishio et al. |
| 2015/0352339 A1 | 12/2015 | Wang |
| 2016/0045302 A1* | 2/2016 | Nishio ................ A61F 2/04 |
| | | 623/23.66 |
| 2016/0051176 A1 | 2/2016 | Ramos et al. |
| 2016/0058489 A1 | 3/2016 | Fischell et al. |
| 2016/0213881 A9 | 7/2016 | Adams, Jr. et al. |
| 2016/0303303 A1 | 10/2016 | Rovatti et al. |
| 2016/0310711 A1 | 10/2016 | Luxon et al. |
| 2016/0331294 A1 | 11/2016 | Imran et al. |
| 2016/0367747 A1 | 12/2016 | Loske |
| 2017/0020724 A1 | 1/2017 | Burnett et al. |
| 2017/0021128 A1 | 1/2017 | Erbey, II et al. |
| 2017/0095323 A1 | 4/2017 | Garcia |
| 2017/0095641 A1 | 4/2017 | Scarpine et al. |
| 2017/0119519 A1 | 5/2017 | Sambusseti et al. |
| 2017/0128639 A1 | 5/2017 | Erbey, II et al. |
| 2017/0128654 A1* | 5/2017 | Feld ................ A61M 25/10 |
| 2017/0136222 A1 | 5/2017 | Hakim et al. |
| 2017/0196576 A1 | 7/2017 | Long et al. |
| 2017/0197028 A1 | 7/2017 | Goldsmith |
| 2017/0232153 A1 | 8/2017 | Babu et al. |
| 2017/0266414 A1 | 9/2017 | Rocha-Singh et al. |
| 2017/0325927 A1 | 11/2017 | Gobel |
| 2017/0348507 A1 | 12/2017 | Erbey, II et al. |
| 2017/0348512 A1 | 12/2017 | Or et al. |
| 2017/0367636 A1 | 12/2017 | Mantinband et al. |
| 2018/0001055 A1 | 1/2018 | Utas et al. |
| 2018/0116751 A1 | 5/2018 | Schwartz et al. |
| 2018/0117288 A1 | 5/2018 | Lindsay et al. |
| 2018/0177458 A1 | 6/2018 | Burnett |
| 2018/0193618 A1 | 7/2018 | Erbey, II et al. |
| 2018/0207412 A1 | 7/2018 | Malek et al. |
| 2018/0344250 A1 | 12/2018 | McKinney et al. |
| 2019/0030303 A1 | 1/2019 | Holman et al. |
| 2019/0091442 A1 | 3/2019 | Erbey, II et al. |
| 2019/0105465 A1 | 4/2019 | Erbey, II et al. |
| 2019/0201662 A1 | 7/2019 | Lad et al. |
| 2019/0240448 A1 | 8/2019 | Murdock |
| 2019/0247615 A1 | 8/2019 | Bishawi |
| 2020/0001045 A1* | 1/2020 | McIntyre .......... A61M 25/0026 |
| 2020/0094017 A1 | 3/2020 | Erbey, II et al. |
| 2021/0178133 A1 | 6/2021 | Walish et al. |

FOREIGN PATENT DOCUMENTS

| | | |
|---|---|---|
| CA | 2205473 C | 6/2006 |
| CN | 2175619 Y | 8/1994 |
| CN | 2562776 Y | 7/2003 |
| CN | 2588940 Y | 12/2003 |
| CN | 1479596 A | 3/2004 |
| CN | 2753382 Y | 1/2006 |

(56) References Cited

FOREIGN PATENT DOCUMENTS

| | | |
|---|---|---|
| CN | 2928043 Y | 8/2007 |
| CN | 101224148 A | 7/2008 |
| CN | 101426540 A | 5/2009 |
| CN | 201814968 U | 5/2011 |
| CN | 102176928 A | 9/2011 |
| CN | 202459720 U | 10/2012 |
| CN | 202526754 U | 11/2012 |
| CN | 202802478 U | 3/2013 |
| CN | 103096964 A | 5/2013 |
| CN | 103203062 A | 7/2013 |
| CN | 103841905 A | 6/2014 |
| CN | 203777060 U | 8/2014 |
| CN | 203842151 U | 9/2014 |
| CN | 204158867 U | 2/2015 |
| CN | 204246651 U | 4/2015 |
| CN | 204446944 U | 7/2015 |
| CN | 205126495 U | 4/2016 |
| CN | 106237417 A | 12/2016 |
| CN | 106473847 A | 3/2017 |
| CN | 106693092 A | 5/2017 |
| CN | 107261294 A | 10/2017 |
| DE | 102012016049 A1 | 2/2014 |
| EP | 873760 A1 | 10/1998 |
| EP | 1011803 B1 | 1/2004 |
| EP | 1980292 A2 | 10/2008 |
| EP | 3488897 A1 | 5/2019 |
| EP | 3970775 A1 | 3/2022 |
| JP | 59111748 A | 6/1984 |
| JP | H42361 A | 1/1992 |
| JP | 200250536 A | 4/2002 |
| JP | 2002291879 A | 10/2002 |
| JP | 200253888 | 11/2002 |
| JP | 2002537893 A | 11/2002 |
| JP | 2003530165 A | 10/2003 |
| JP | 2004215787 A | 8/2004 |
| JP | 2006516214 A | 6/2006 |
| JP | 2006526464 A | 11/2006 |
| JP | 2009505802 A | 2/2009 |
| JP | 2009238520 A | 10/2009 |
| JP | 2009537256 A | 10/2009 |
| JP | 20105282 A | 1/2010 |
| JP | 2010508984 A | 3/2010 |
| JP | 2010119737 A | 6/2010 |
| JP | 2010230618 A | 10/2010 |
| JP | 2013149498 A | 1/2012 |
| JP | 2012505022 A | 3/2012 |
| JP | 2012530575 A | 12/2012 |
| JP | 2014136116 A | 7/2014 |
| JP | 2014176689 A | 9/2014 |
| RU | 2113245 C1 | 6/1998 |
| RU | 2300399 C1 | 6/2007 |
| RU | 149161 U1 | 12/2014 |
| TW | M540625 U | 5/2017 |
| WO | 9529716 A1 | 11/1995 |
| WO | 9716218 A1 | 5/1997 |
| WO | 9816171 A1 | 4/1998 |
| WO | 9850088 A1 | 11/1998 |
| WO | 0054701 A1 | 9/2000 |
| WO | 0160260 A1 | 8/2001 |
| WO | 6558350 A1 | 12/2001 |
| WO | 03017870 A1 | 3/2003 |
| WO | 2004064681 A1 | 8/2004 |
| WO | 2006017439 A2 | 2/2006 |
| WO | 2006023589 A2 | 3/2006 |
| WO | 2006044621 A2 | 4/2006 |
| WO | 2007001978 A2 | 1/2007 |
| WO | 2007027830 A1 | 3/2007 |
| WO | 2008066625 A1 | 6/2008 |
| WO | 2010082197 A2 | 7/2010 |
| WO | 2011109570 A2 | 9/2011 |
| WO | 2011139498 A1 | 11/2011 |
| WO | 2013022005 A1 | 2/2013 |
| WO | 2013029622 A1 | 3/2013 |
| WO | 2014025367 A1 | 2/2014 |
| WO | 2014043650 A2 | 3/2014 |
| WO | 2014062225 A1 | 4/2014 |
| WO | 2015105916 A1 | 7/2015 |
| WO | 2015157467 A1 | 10/2015 |
| WO | 2015198333 A1 | 12/2015 |
| WO | 2016049654 A1 | 3/2016 |
| WO | 2016103256 A1 | 6/2016 |
| WO | 2017015345 A2 | 1/2017 |
| WO | 2017015351 A2 | 1/2017 |
| WO | 2017019974 A1 | 2/2017 |
| WO | 2017087182 A1 | 5/2017 |
| WO | 2018186781 A1 | 10/2018 |
| WO | 2018200050 A1 | 11/2018 |
| WO | 2019038730 A1 | 2/2019 |
| WO | 2020236748 A1 | 11/2020 |

OTHER PUBLICATIONS

Burr et al.; "Urinary catheter blockage depends on urine pH, calcium and rate of flow"; Spinal Cord; 1997; p. 521-525; vol. 35.
Clinical Practice Guidelines for Chronic Kidney Disease: Evaluation, Classification and Stratification; National Kidney Foundation; Am. J. Kidney Dis.; 2002; p. S1-S266; Suppl. 1.
"The Criteria Committee of the New York Heart Association", (1994), Nomenclature and Criteria for Diagnosis of Diseases of the Heart and Great Vessels, (9th ed.), Boston: Little, Brown & Co. p. 253-256 (Abstract).
Harris et al., "Relationship between patients' outcomes and the changes in serum creatinine and urine output and RIFLE classification in a large critical care cohort database", Kidney International, 2015, p. 369-377, vol. 88.
Jessup et al.; "The Cardiorenal Syndrome—Do We Need a Change of Strategy or a Change of Tactics?"; Journal of the American College of Cardiology; 2009; p. 597-599; vol. 53:7.
Mardis et al., "Comparative Evaluation of Materials Used for Internal Ureteral Stents", Journal of Endourology, 1993, pp. 105-115, vol. 7:2.
Mullens et al.; "Importance of Venous Congestion for Worsening of Renal Function in Advanced Decompensated Heart Failure"; Journal of the American College of Cardiology; 2009; p. 589-596; vol. 53:7.
Peters et al.; "Short and Long-Term Effects of the Angiotensin II Receptor Blocker Irbesartan on Intradialytic Central Hemodynamics: A Randomized Double-Blind Placebo-Controlled One-Year Intervention Trial (the SAFIR Study)" PLoS One; Jun. 1, 2015; p. 1-22.
"Standard Specification for Ureteral Stents", ASTM International, 2014, Designation F1828-97, p. 1-6.
Verbrugge et al.; "The kidney in congestive heart failure: are natriuresis, sodium, and diuretics really the good, the bad and the ugly? "; European Journal of Heart Failure; 2014; p. 133-142; vol. 16.
Wolf, Jr. et al.; "Comparative Ureteral Microanatomy"; Journal of Endourology; 1996; p. 527-531; vol. 10:6.
Zelenko et al.; "Normal Ureter Size on Unenhanced Helical CT"; American Journal of Roentgenology; 2004; p. 1039-1041; vol. 182.
Johnson et al., "Clinical Practice Guidelines for Chronic Kidney Disease in Adults: Part I. Definition, Disease Stages, Evaluation, Treatment, and Risk Factors", American Family Physician, Sep. 1, 2004, p. 869-876, vol. 70 Issue 5.
Mordi et al., "Renal and Cardiovascular Effects of sodium-glucose cotransporter 2 (SGLT2) inhibition with loop Diuretics in diabetic patents with Chronic Heart Failure (REEDE-CHF): protocol for a randomised controlled double-blind cross-over trail". BJM open, 2017, vol. 7, pp. 1-9.
Quadra-Coil | Olympus America | Medical, Ureteral Stents, https://www.medical.olympusamerica.com/products/quadra-coil (downloaded from the Internet Aug. 31, 2022) 2 pages.
14 Stents—Urology | Olympus America | Medical. Ureteral Stents, https://www.medical.olympusamerica.com/products/stents-Urology (downloaded from the Internet Aug. 31, 2022) 2 pages.
Ureteral stent—Quadra-Coil—Olympus Medical Europa, https://www.medicalexpo.com/prod/olympus-medical-europa/product-69587-661607.html (downloaded from the Internet Aug. 31, 2022) 5 pages.

(56) References Cited

OTHER PUBLICATIONS

Damman et al., "Increased Central Venous Pressure Is Associated With Impaired Renal Function and Mortality in a Broad Spectrum of Patients With Cardiocascular Disease", 2009, Journal of the American College of Cardiology, vol. 53:7, pp. 582-588.
Dixon et al., "The musculature of the human renal calices, pelvis and upper ureter", J, Anat., 1982, vol. 135, pp. 129-137.
Gregersen et al., "Regional Differences Exist in Elastic Wall Properties in the Ureter", SJUN, 1996, vol. 30, pp. 343-348.
Kiil, "Urinary Flow and Ureteral Peristalsis" in: Lutzeyer W., Melchior H. (Eds.) Urodynamics, 1973, Springer, Berlin, Heidelberg (pp. 57-70).
Lala et al., "Relief and Recurrence of Congestion During and After Hospitalization for Acute Heart Failure: Insights from DOSE-AHF and CARRESS-HF", Circ Heart Fail, 2015, vol. 8:4, pp. 741-748.
Legrand et al. "Association between systemic hemodynamics and septic acute kidney injury in critically ill patients: a retrospective observational study", Critical Care, 2013, vol. 17:R278, pp. 1-8.
Nohria et al., "Cardiorenal Interactions Insights from the ESCAPE Trial", Heart Failure, 2008, vol. 51:13, pp. 1268-1274.
Uthoff et al., "Central venous pressure and impaired renal function in patients with acute heart failure", European Journal of Heart Failure, 2011. vol. 13, pp. 432-439.
Walker, "Annals of Surgery" 1913, Lippincott Williams & Wilkins, p. 58, Figs. 3 and 9.
Webb, "Percutaneous Renal Surgery: A Practical Clinical Handbook", 2016, Springer International Publishing, Switzerland, p. 92.
Woodburne et al., "The Uretal Lumen during Peristalsis", Am. J. Anat., 1972. vol. 133, pp. 255-258.

\* cited by examiner

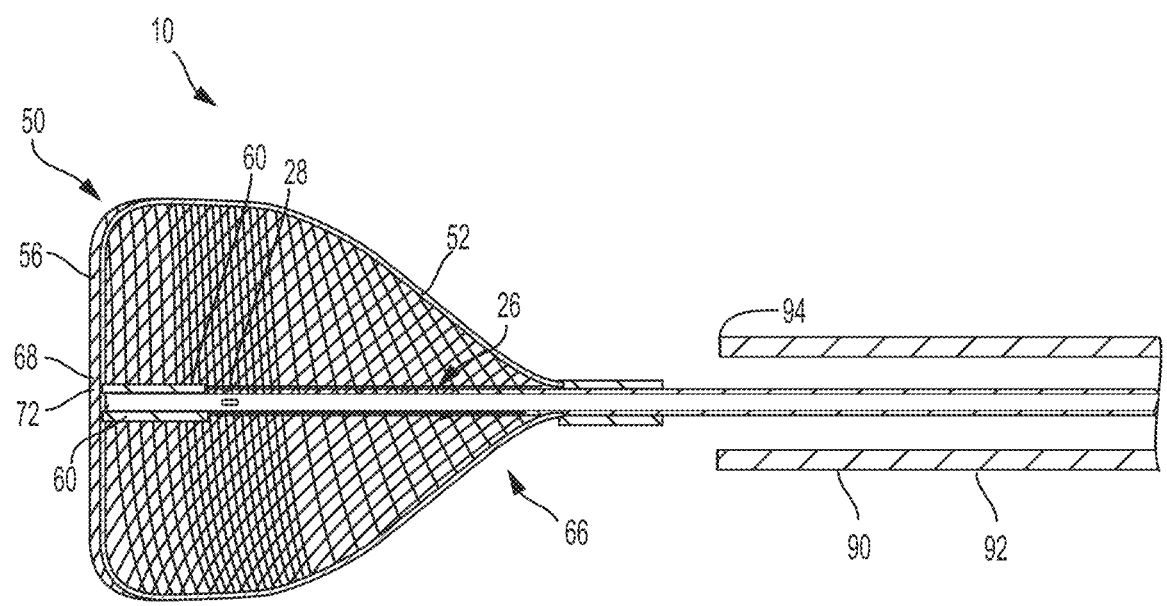
FIG. 5A
FIG. 5B
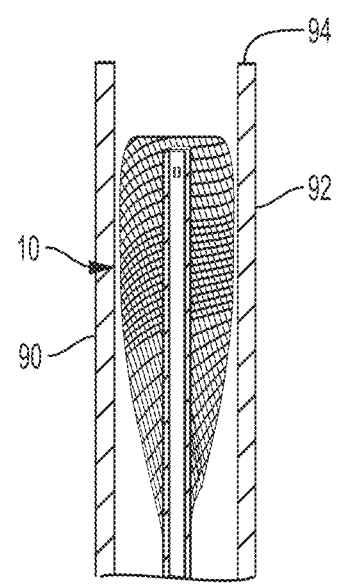

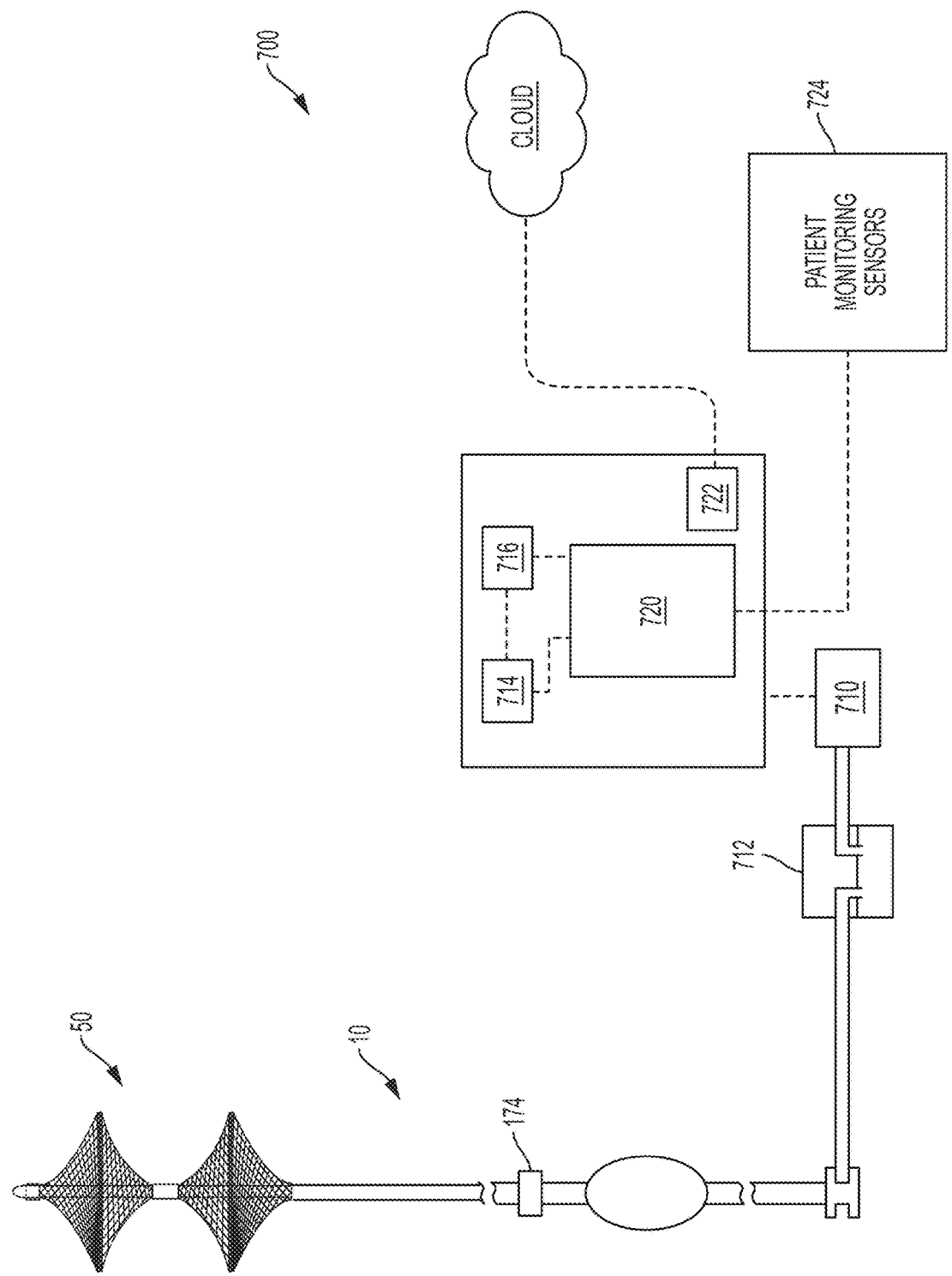

CATHETER DEVICE AND METHOD FOR INDUCING NEGATIVE PRESSURE IN A PATIENT'S BLADDER

CROSS REFERENCE TO RELATED APPLICATIONS

This application is a continuation of U.S. patent application Ser. No. 15/879,869 filed Jan. 25, 2018, which is a continuation-in-part of U.S. patent application Ser. No. 15/687,064 filed Aug. 25, 2017, now issued as U.S. Pat. No. 10,765,834, which is a continuation-in-part of U.S. patent application Ser. No. 15/411,884 filed Jan. 20, 2017, now issued as U.S. Pat. No. 10,512,713, which is a continuation-in-part of U.S. patent application Ser. No. 15/214,955 filed Jul. 20, 2016, now issued as U.S. patent Ser. No. 10/307,564, which claims the benefit of U.S. Provisional Application No. 62/300,025 filed Feb. 25, 2016, U.S. Provisional Application No. 62/278,721, filed Jan. 14, 2016, U.S. Provisional Application No. 62/260,966 filed Nov. 30, 2015, and U.S. Provisional Application No. 62/194,585, filed Jul. 20, 2015, each of which is incorporated by reference herein in its entirety.

Also, U.S. patent application Ser. No. 15/879,976, filed Jan. 25, 2018, is a continuation-in-part of U.S. patent application Ser. No. 15/687,083 filed Aug. 25, 2017, which is a continuation-in-part of U.S. patent application Ser. No. 15/411,884 filed Jan. 20, 2017, now issued as U.S. Pat. No. 10,512,713, which is a continuation-in-part of U.S. patent application Ser. No. 15/214,955 filed Jul. 20, 2016, now issued as U.S. patent Ser. No. 10/307,564, which claims the benefit of U.S. Provisional Application No. 62/300,025 filed Feb. 25, 2016, U.S. Provisional Application No. 62/278,721, filed Jan. 14, 2016, U.S. Provisional Application No. 62/260, 966 filed Nov. 30, 2015, and U.S. Provisional Application No. 62/194,585, filed Jul. 20, 2015, each of which is incorporated by reference herein in its entirety.

Also, U.S. patent application Ser. No. 15/879,976, filed Jan. 25, 2018, is a continuation-in-part of U.S. patent application Ser. No. 15/745,823 filed Jan. 18, 2018, which is the U.S. national phase of PCT/US2016/043101, filed Jul. 20, 2016, which claims the benefit of U.S. Provisional Application No. 62/300,025 filed Feb. 25, 2016, U.S. Provisional Application No. 62/278,721, filed Jan. 14, 2016, U.S. Provisional Application No. 62/260,966 filed Nov. 30, 2015, and U.S. Provisional Application No. 62/194,585, filed Jul. 20, 2015, each of which is incorporated by reference herein in its entirety.

Also, U.S. patent application Ser. No. 15/879,976, filed Jan. 25, 2018, claims the benefit of U.S. Provisional Application No. 62/489,789 filed Apr. 25, 2017 and U.S. Provisional Application No. 62/489,831 filed Apr. 25, 2017.

BACKGROUND

Technical Field

The present disclosure relates to devices and methods for treating impaired renal function across a variety of disease states and, in particular, to devices and methods for collection of urine and inducement of negative and/or positive pressure in portions of a patient's urinary tract.

Background

The renal or urinary system includes a pair of kidneys, each kidney being connected by a ureter to the bladder, and a urethra for draining urine produced by the kidneys from the bladder. The kidneys perform several vital functions for the human body including, for example, filtering the blood to eliminate waste in the form of urine. The kidneys also regulate electrolytes (e.g., sodium, potassium and calcium) and metabolites, blood volume, blood pressure, blood pH, fluid volume, production of red blood cells, and bone metabolism. Adequate understanding of the anatomy and physiology of the kidneys is useful for understanding the impact that altered hemodynamics other fluid overload conditions have on their function.

In normal anatomy, the two kidneys are located retroperitoneally in the abdominal cavity. The kidneys are bean-shaped encapsulated organs. Urine is formed by nephrons, the functional unit of the kidney, and then flows through a system of converging tubules called collecting ducts. The collecting ducts join together to form minor calyces, then major calyces, which ultimately join near the concave portion of the kidney (renal pelvis). A major function of the renal pelvis is to direct urine flow to the ureter. Urine flows from the renal pelvis into the ureter, a tube-like structure that carries the urine from the kidneys into the bladder. The outer layer of the kidney is called the cortex, and is a rigid fibrous encapsulation. The interior of the kidney is called the medulla. The medulla structures are arranged in pyramids.

Each kidney is made up of approximately one million nephrons. A schematic drawing of a nephron $1102$ is shown in FIG. 39. Each nephron includes the glomerulus $1110$, Bowman's capsule $1112$, and tubules $1114$. The tubules $1114$ include the proximal convoluted tubule $1116$, the loop of Henle $1118$, the distal convoluted tubule $1120$, and the collecting duct $1122$. The nephrons $1102$ contained in the cortex layer of the kidney are distinct from the anatomy of those contained in the medulla. The principal difference is the length of the loop of Henle $1118$. Medullary nephrons contain a longer loop of Henle, which, under normal circumstances, allows greater regulation of water and sodium reabsorption than in the cortex nephrons.

The glomerulus is the beginning of the nephron, and is responsible for the initial filtration of blood. Afferent arterioles pass blood into the glomerular capillaries, where hydrostatic pressure pushes water and solutes into Bowman's capsule. Net filtration pressure is expressed as the hydrostatic pressure in the afferent arteriole minus the hydrostatic pressure in Bowman's space minus the osmotic pressure in the efferent arteriole.

$$\text{Net Filtration Pressure} = \text{Hydrostatic Pressure(Afferent Arteriole)} - \text{Hydrostatic Pressure(Bowman's Space)} - \text{Osmotic Pressure(Efferent Arteriole)} \quad \text{(Equation 1)}$$

The magnitude of this net filtration pressure defined by Equation 1 determines how much ultra-filtrate is formed in Bowman's space and delivered to the tubules. The remaining blood exits the glomerulus via the efferent arteriole. Normal glomerular filtration, or delivery of ultra-filtrate into the tubules, is about 90 ml/min/1.73 m$^2$.

The glomerulus has a three-layer filtration structure, which includes the vascular endothelium, a glomerular basement membrane, and podocytes. Normally, large proteins such as albumin and red blood cells, are not filtered into Bowman's space. However, elevated glomerular pressures and mesangial expansion create surface area changes on the basement membrane and larger fenestrations between the podocytes allowing larger proteins to pass into Bowman's space.

Ultra-filtrate collected in Bowman's space is delivered first to the proximal convoluted tubule. Re-absorption and secretion of water and solutes in the tubules is performed by a mix of active transport channels and passive pressure gradients. The proximal convoluted tubules normally reabsorb a majority of the sodium chloride and water, and nearly all glucose and amino acids that were filtered by the glomerulus. The loop of Henle has two components that are designed to concentrate wastes in the urine. The descending limb is highly water permeable and reabsorbs most of the remaining water. The ascending limb reabsorbs 25% of the remaining sodium chloride, creating a concentrated urine, for example, in terms of urea and creatinine. The distal convoluted tubule normally reabsorbs a small proportion of sodium chloride, and the osmotic gradient creates conditions for the water to follow.

Under normal conditions, there is a net filtration of approximately 14 mmHg. The impact of venous congestion can be a significant decrease in net filtration, down to approximately 4 mmHg. See Jessup M., *The cardiorenal syndrome: Do we need a change of strategy or a change of tactics?*, JACC 53(7):597-600, 2009 (hereinafter "Jessup"). The second filtration stage occurs at the proximal tubules. Most of the secretion and absorption from urine occurs in tubules in the medullary nephrons. Active transport of sodium from the tubule into the interstitial space initiates this process. However, the hydrostatic forces dominate the net exchange of solutes and water. Under normal circumstances, it is believed that 75% of the sodium is reabsorbed back into lymphatic or venous circulation. However, because the kidney is encapsulated, it is sensitive to changes in hydrostatic pressures from both venous and lymphatic congestion. During venous congestion the retention of sodium and water can exceed 85%, further perpetuating the renal congestion. See Verbrugge et al., *The kidney in congestive heart failure: Are natriuresis, sodium, and diruetucs really the good, the bad and the ugly? European Journal of Heart Failure* 2014:16, 133-42 (hereinafter "Verbrugge").

Venous congestion can lead to a prerenal form of acute kidney injury (AKI). Prerenal AKI is due to a loss of perfusion (or loss of blood flow) through the kidney. Many clinicians focus on the lack of flow into the kidney due to shock. However, there is also evidence that a lack of blood flow out of the organ due to venous congestion can be a clinically important sustaining injury. See Damman K, *Importance of venous congestion for worsening renal function in advanced decompensated heart failure*, JACC 17:589-96, 2009 (hereinafter "Damman").

Prerenal AKI occurs across a wide variety of diagnoses requiring critical care admissions. The most prominent admissions are for sepsis and Acute Decompensated Heart Failure (ADHF). Additional admissions include cardiovascular surgery, general surgery, cirrhosis, trauma, burns, and pancreatitis. While there is wide clinical variability in the presentation of these disease states, a common denominator is an elevated central venous pressure. In the case of ADHF, the elevated central venous pressure caused by heart failure leads to pulmonary edema, and, subsequently, dyspnea in turn precipitating the admission. In the case of sepsis, the elevated central venous pressure is largely a result of aggressive fluid resuscitation. Whether the primary insult was low perfusion due to hypovolemia or sodium and fluid retention, the sustaining injury is the venous congestion resulting in inadequate perfusion.

Hypertension is another widely recognized state that creates perturbations within the active and passive transport systems of the kidney(s). Hypertension directly impacts afferent arteriole pressure and results in a proportional increase in net filtration pressure within the glomerulus. The increased filtration fraction also elevates the peritubular capillary pressure, which stimulates sodium and water re-absorption. See Verbrugge.

Because the kidney is an encapsulated organ, it is sensitive to pressure changes in the medullary pyramids. The elevated renal venous pressure creates congestion that leads to a rise in the interstitial pressures. The elevated interstitial pressures exert forces upon both the glomerulus and tubules. See Verburgge. In the glomerulus, the elevated interstitial pressures directly oppose filtration. The increased pressures increase the interstitial fluid, thereby increasing the hydrostatic pressures in the interstitial fluid and peritubular capillaries in the medulla of the kidney. In both instances, hypoxia can ensue leading to cellular injury and further loss of perfusion. The net result is a further exacerbation of the sodium and water re-absorption creating a negative feedback. See Verbrugge, 133-42. Fluid overload, particularly in the abdominal cavity is associated with many diseases and conditions, including elevated intra-abdominal pressure, abdominal compartment syndrome, and acute renal failure. Fluid overload can be addressed through renal replacement therapy. See Peters, C. D., *Short and Long-Term Effects of the Angiotensin II Receptor Blocker Irbesartanon Intradialytic Central Hemodynamics: A Randomized Double-Blind Placebo-Controlled One-Year Intervention Trial (the SAFIR Study)*, PLoS ONE (2015) 10(6): e0126882. doi:10.1371/journal.pone.0126882 (hereinafter "Peters"). However, such a clinical strategy provides no improvement in renal function for patients with the cardiorenal syndrome. See Bart B, *Ultrafiltration in decompensated heart failure with cardiorenal syndrome*, NEJM 2012; 367:2296-2304 (hereinafter "Bart").

In view of such problematic effects of fluid retention, devices and methods for improving removal of urine from the urinary tract and, specifically for increasing quantity and quality of urine output from the kidneys, are needed.

SUMMARY

According to an aspect of the disclosure, a fluid collection catheter configured to be deployed in a urinary tract of a patient includes: an elongated tube having a proximal portion configured for placement in a urethra of the patient, a distal portion comprising a distal end, and a sidewall extending between a proximal end and the distal end of the elongated tube defining at least one drainage lumen extending through the tube, the sidewall comprising a drainage portion which allows fluid to pass through the sidewall and into the drainage lumen. The catheter also includes a permeable tissue support directly or indirectly connected to the distal portion of the elongated tube and extending axially and/or radially therefrom, the tissue support being configured to be deployed in the urinary tract to maintain the distal end of the elongated tube at a predetermined position in a bladder, a ureter, a renal pelvis, or a kidney of the patient. When deployed, the permeable tissue support defines a three-dimensional shape of sufficient size to permit flow of at least a portion of fluid from the urinary tract through the tissue support and drainage portion of the elongated tube to the at least one drainage lumen.

According to another aspect of the disclosure, a method of inducing a negative pressure to a urinary tract of a patient for enhancing urine excretion therefrom includes: inserting a distal portion of an elongated tube of a urine collection catheter into the urinary tract, the elongated tube comprising a proximal portion configured for placement in a urethra of the patient, a distal portion comprising a distal end, and a sidewall extending between a proximal end and the distal end of the elongated tube defining at least one drainage lumen extending through the tube, the sidewall comprising a drainage portion which allows fluid to pass through the sidewall and into the drainage lumen. The method also includes a step of deploying a permeable tissue support directly or indirectly connected to and extending axially and/or radially from the elongated tube at a predetermined position in a bladder, a ureter, a renal pelvis, or a kidney of the patient, wherein the permeable tissue support is configured to be deployed in the urinary tract to maintain the distal end of the elongated tube at the predetermined position, and wherein, when deployed, the permeable tissue support defines a three-dimensional shape of sufficient size to permit flow of at least a portion of fluid from the urinary tract through the permeable tissue support and drainage portion of the sidewall to the at least one drainage lumen extending through the elongated tube. The method also includes a step of inducing a negative pressure through the at least one drainage lumen of the elongated tube to draw urine from the urinary tract into the drainage lumen.

According to another aspect of the disclosure, a system for drawing urine from a urinary tract of a patient includes an elongated tube comprising a proximal portion configured for placement in a urethra of the patient, a distal portion comprising a distal end, and a sidewall extending between a proximal end and the distal end of the elongated tube defining at least one drainage lumen extending through the tube, the sidewall comprising a drainage portion which allows fluid to pass through the sidewall and into the drainage lumen. The system also includes a permeable tissue support directly or indirectly connected to the distal portion of the elongated tube and extending axially and/or radially therefrom, the tissue support being configured to be deployed in the urinary tract to maintain the distal end of the elongated tube at a predetermined position in a bladder, a ureter, a renal pelvis, or a kidney of the patient. When deployed, the permeable tissue support defines a three-dimensional shape of sufficient size to permit flow of at least a portion of fluid from the urinary tract through the permeable tissue support and drainage portion of the sidewall to the at least one drainage lumen extending through the elongated tube. The system also includes a pump in fluid connection with the drainage lumen of the elongated tube, wherein the pump is configured to introduce an internal negative pressure through the drainage lumen to the urinary tract of the patient to draw urine from the urinary tract.

Non-limiting examples of the present invention will now be described in the following numbered clauses:

Clause 1: A fluid collection catheter configured to be deployed in a urinary tract of a patient, comprising: an elongated tube comprising a proximal portion configured for placement in a urethra of the patient, a distal portion comprising a distal end, and a sidewall extending between a proximal end and the distal end of the elongated tube defining at least one drainage lumen extending through the tube, the sidewall comprising a drainage portion which allows fluid to pass through the sidewall and into the drainage lumen; and a permeable tissue support directly or indirectly connected to the distal portion of the elongated tube and extending axially and/or radially therefrom, the tissue support being configured to be deployed in the urinary tract to maintain the distal end of the elongated tube at a predetermined position in a bladder, a ureter, a renal pelvis, or a kidney of the patient, wherein, when deployed, the permeable tissue support defines a three-dimensional shape of sufficient size to permit flow of at least a portion of fluid from the urinary tract through the tissue support and drainage portion of the elongated tube to the at least one drainage lumen.

Clause 2: The catheter of clause 1, wherein, when deployed, the permeable tissue support at least partially encloses the drainage portion of the sidewall.

Clause 3: The catheter of clause 1 or clause 2, wherein the permeable tissue support comprises a permeable material.

Clause 4: The catheter of clause 3, wherein the permeable material comprises at least one of biocompatible polymer fiber(s); metallic fiber(s), porous film(s), film(s) comprising one or more apertures, fabric(s), or any combination thereof.

Clause 5: The catheter of clause 3 or clause 4, wherein the permeable material has a thickness of from about 0.5 mm to about 5 mm.

Clause 6: The catheter of any of clauses 1 to 5, wherein the permeable tissue support comprises a plurality of elongated members having a first end and/or a second end connected to the elongated tube woven together to form a mesh of elongated members.

Clause 7: The catheter of any of clauses 1 to 6, wherein, when deployed in the patient's bladder, the permeable tissue support is configured to maintain a volume of the three dimensional shape when an interior of the bladder is exposed to an internal negative pressure.

Clause 8: The catheter of any of clauses 1 to 7, wherein, when deployed in the patient's bladder, the permeable tissue support is configured to maintain a volume of the three dimensional shape when an interior of the bladder is exposed to an internal negative pressure of from 5 to 150 mmHg.

Clause 9: The catheter of any of clauses 1 to 8, wherein, when deployed in the patient's bladder, the permeable tissue support is configured to inhibit mucosal tissue from occluding at least a portion of the drainage portion of the sidewall.

Clause 10: The catheter of any of clauses 1 to 9, wherein the permeable tissue support has a maximum outer diameter of from about 10 mm to about 100 mm.

Clause 11: The catheter of any of clauses 1 to 10, wherein a length between a proximal end and a distal end of the permeable tissue support is from about 10 mm to about 100 mm.

Clause 12: The catheter of any of clauses 1 to 11, wherein the elongated tube has an outer diameter of from about 0.5 mm to about 10 mm.

Clause 13: The catheter of any of clauses 1 to 12, wherein the elongated tube has an inner diameter of from about 0.5 mm to about 9 mm.

Clause 14: The catheter of any of clauses 1 to 13, wherein, when deployed, the three dimensional shape has a volume of from 0.1 cm$^3$ to 500 cm$^3$.

Clause 15: The catheter of any of clauses 1 to 14, wherein, when deployed, a middle portion of the permeable tissue support bulges radially outward from proximal and distal ends of the permeable tissue support, such that an outer diameter of the permeable tissue support increases from the proximal end to the middle portion thereof and decreases from the middle portion to the distal end thereof.

Clause 16: The catheter of any of clauses 1 to 14, wherein, when deployed, the permeable tissue support comprises at least one middle portion located between a proximal portion and a distal portion of the tissue support, and wherein the middle portion has a minimum outer diameter which is less than a maximum outer diameter of the proximal portion and the distal portion of the permeable tissue support.

Clause 17: The catheter of clause 16, wherein the minimum outer diameter of the middle portion is from about 2.5 mm to about 20 mm less than the maximum outer diameter of the proximal portion or the distal portion of the tissue support.

Clause 18: The catheter of clause 16 or clause 17, wherein the minimum outer diameter of the middle portion is from equal to an outer diameter of the elongated to about 40 mm greater than an outer diameter of the elongated tube.

Clause 19: The catheter of any of clauses 16 to 18, wherein the minimum outer diameter of the middle portion is from about 10% to about 99% less than the maximum outer diameter of the proximal portion or the distal portion of the tissue support.

Clause 20: The catheter of any of clauses 1 to 19, wherein the drainage portion of the sidewall comprises a perforated section of tubing comprising at least one perforation permitting fluid to flow through the sidewall of the elongated tube into the at least one drainage lumen.

Clause 21: The catheter of clause 20, wherein the at least one perforation has one or more shapes, each shape being selected from at least one of a circular shape, an elliptical shape, a square shape, a regular polygonal shape, an irregular circular shape, or an irregular polygonal shape, or combinations thereof.

Clause 22: The catheter of clause 20 or clause 21, wherein the at least one perforation has a diameter of about 0.05 mm to about 2.0 mm.

Clause 23: The catheter of any of clauses 20 to 22, wherein, when deployed in the patient's bladder, the permeable tissue support is configured to inhibit any portion of a wall of the bladder from occluding the at least one perforation of the drainage portion upon delivery of negative pressure to an interior of the bladder through the drainage lumen of the elongated tube.

Clause 24: The catheter of any of clauses 1 to 23, wherein, when deployed in the patient's bladder, the permeable tissue support is configured to inhibit any portion of the bladder wall from occluding or obstructing ureteral orifice upon delivery of negative pressure to the bladder through the drainage lumen of the tube.

Clause 25: The catheter of any of clauses 1 to 24, further comprising at least one collar slidably connected to the elongated tube, wherein at least a portion of the permeable tissue support is connected to the collar.

Clause 26: The catheter of clause 25, wherein sliding the collar along the elongated tube deploys or retracts the permeable tissue support.

Clause 27: The catheter of any of clauses 1 to 24, wherein the elongated tube comprises an inner tube, further comprising an elongated outer tube at least partially surrounding the inner tube, the outer tube having a proximal end portion, a distal end portion, and a sidewall extending therebetween, wherein a distal portion of the permeable tissue support is connected to the inner tube and a proximal portion of the permeable tissue support is connected to the outer elongated tube.

Clause 28: The catheter of clause 27, wherein sliding the inner tube relative to the outer tube causes at least one of deployment and retraction of the permeable tissue support.

Clause 29: The catheter of clause 27 or clause 28, wherein the drainage portion of the sidewall comprises one or more perforations, and wherein at least one perforation is at least partially enclosed by the permeable tissue support, when the permeable tissue support is deployed.

Clause 30: The catheter of any of clauses 1 to 29, further comprising a delivery catheter comprising a proximal end configured to remain external to the body, a distal end for insertion into the bladder, a sidewall extending therebetween, and at least one lumen sized to receive the elongated tube and permeable tissue support, wherein the delivery catheter is configured to maintain the permeable tissue support in a retracted position during insertion of the permeable tissue support to the urinary tract of the patient.

Clause 31: The catheter of clause 30, wherein the delivery catheter has an inner diameter of from about 5 mm to about 20 mm.

Clause 32: The catheter of clause 30 or clause 31, wherein the permeable tissue support is biased to a deployed position, such that when pushed from the distal end of the delivery sheath, the permeable tissue support adopts its deployed configuration.

Clause 33: The catheter of any of clauses 1 to 32, wherein the permeable tissue support is configured to transition from a retracted position in which at least a portion of an inner surface of the tissue support contacts an outer surface of the sidewall to a deployed position in which the portion of the inner surface of the tissue support is spaced apart from the sidewall.

Clause 34: A method of inducing a negative pressure to a urinary tract of a patient for enhancing urine excretion therefrom, the method comprising: inserting a distal portion of an elongated tube of a urine collection catheter into the urinary tract, the elongated tube comprising a proximal portion configured for placement in a urethra of the patient, a distal portion comprising a distal end, and a sidewall extending between a proximal end and the distal end of the elongated tube defining at least one drainage lumen extending through the tube, the sidewall comprising a drainage portion which allows fluid to pass through the sidewall and into the drainage lumen; deploying a permeable tissue support directly or indirectly connected to and extending axially and/or radially from the elongated tube at a predetermined position in a bladder, a ureter, a renal pelvis, or a kidney of the patient, wherein the permeable tissue support is configured to be deployed in the urinary tract to maintain the distal end of the elongated tube at the predetermined position, and wherein, when deployed, the permeable tissue support defines a three-dimensional shape of sufficient size to permit flow of at least a portion of fluid from the urinary tract through the permeable tissue support and drainage portion of the sidewall to the at least one drainage lumen extending through the elongated tube; and inducing a negative pressure through the at least one drainage lumen of the elongated tube to draw urine from the urinary tract into the drainage lumen.

Clause 35: The method of clause 34, wherein, when deployed, the permeable tissue support at least partially encloses the drainage portion of the sidewall.

Clause 36: The method of clause 34 or clause 35, wherein the permeable tissue support comprises a permeable material.

Clause 37: The method of clause 36, wherein the permeable material comprises at least one of biocompatible polymer fiber(s); metallic fiber(s), porous film(s), film(s) comprising one or more apertures, fabric(s), or any combination thereof.

Clause 38: The method of any of clauses 34 to 37, wherein, when deployed in the patient's bladder, the permeable tissue support is configured to maintain a volume of the three dimensional shape when an interior of the bladder is exposed to an internal negative pressure.

Clause 39: The method of any of clauses 34 to 38, wherein, when deployed in the patient's bladder, the permeable tissue support is configured to maintain a volume of the three dimensional shape when an interior of the bladder is exposed to an internal negative pressure of from about 5 mmHg to about 125 mmHg.

Clause 40: The method of any of clauses 34 to 39, wherein inducing the negative pressure in the drainage lumen comprises coupling a mechanical pump in fluid communication with the proximal end of the drainage lumen to draw urine from the bladder into the drainage lumen through the drainage portion of the sidewall.

Clause 41: The method of any of clauses 34 to 40, wherein inducing negative pressure comprises applying a negative pressure of from about 0.1 mmHg to about 150 mmHg to the proximal end of the elongated tube.

Clause 42: The method of any of clauses 34 to 41, wherein the elongated tube is inserted into the bladder in a delivery catheter, and wherein deploying the permeable tissue support comprises retracting the delivery catheter to expose the permeable tissue support.

Clause 43: The method of clause 42, wherein the permeable tissue support adopts a deployed position when the delivery catheter is retracted.

Clause 44: A system for drawing urine from a urinary tract of a patient, the system comprising: a urine collection catheter comprising: an elongated tube comprising a proximal portion configured for placement in a urethra of the patient, a distal portion comprising a distal end, and a sidewall extending between a proximal end and the distal end of the elongated tube defining at least one drainage lumen extending through the tube, the sidewall comprising a drainage portion which allows fluid to pass through the sidewall and into the drainage lumen; and a permeable tissue support directly or indirectly connected to the distal portion of the elongated tube and extending axially and/or radially therefrom, the tissue support being configured to be deployed in the urinary tract to maintain the distal end of the elongated tube at a predetermined position in a bladder, a ureter, a renal pelvis, or a kidney of the patient, wherein, when deployed, the permeable tissue support defines a three-dimensional shape of sufficient size to permit flow of at least a portion of fluid from the urinary tract through the permeable tissue support and drainage portion of the sidewall to the at least one drainage lumen extending through the elongated tube; and a pump in fluid connection with the drainage lumen of the elongated tube, wherein the pump is configured to introduce an internal negative pressure through the drainage lumen to the urinary tract of the patient to draw urine from the urinary tract.

Clause 45: The system of clause 44, wherein the permeable tissue support at least partially encloses the open distal end of the elongated tube.

Clause 46: The system of clause 44 or clause 45, wherein the permeable tissue support comprises a permeable material comprising at least one of biocompatible polymer fiber(s); metallic fiber(s), porous film(s), film(s) comprising one or more apertures, fabric(s), or any combination thereof.

Clause 47: The system of any of clauses 44 to 46, wherein, when deployed in the patient's bladder, the permeable tissue support is configured to maintain a volume of the three dimensional shape when an interior of the bladder is exposed to an internal negative pressure.

Clause 48: The system of any of clauses 44 to 47, wherein, when deployed in the patient's bladder, the permeable tissue support is configured to maintain a volume of the three dimensional shape when an interior of the bladder is exposed to an internal negative pressure of from about 5 mmHg to about 150 mmHg.

Clause 49: The system of any of clauses 44 to 48, wherein, when deployed in the patient's bladder, the permeable tissue support is configured to inhibit mucosal tissue from occluding at least a portion of the drainage portion of the sidewall.

Clause 50: The system of any of clauses 44 to 49, wherein the pump provides a sensitivity of about 10 mmHg or less.

Clause 51: The system of any of clauses 44 to 50, wherein the pump is configured to provide a negative pressure of from about 0.1 mmHg to about 150 mmHg.

Clause 52: The system of any of clauses 44 to 51, wherein the pump is configured to provide intermittent negative pressure.

Clause 53: The system of any of clauses 44 to 52, wherein the pump is configured to alternate between providing negative pressure and providing positive pressure.

Clause 54: The system of any of clauses 44 to 53, wherein the pump is configured to alternate between providing negative pressure and equalizing pressure to atmosphere.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which:

FIG. 5A is a side view of the urine collection catheter of FIG. 4A in a deployed position and including a delivery catheter according to an example of the disclosure;

FIG. 5B is a side view of the urine collection catheter of FIG. 4A retracted within the delivery catheter of FIG. 5A according to an example of the disclosure;

FIG. 13 is a schematic drawing of a system for inducing negative pressure to the urinary tract of a patient according to an example of the present disclosure;

DETAILED DESCRIPTION OF THE INVENTION

Figure 1:
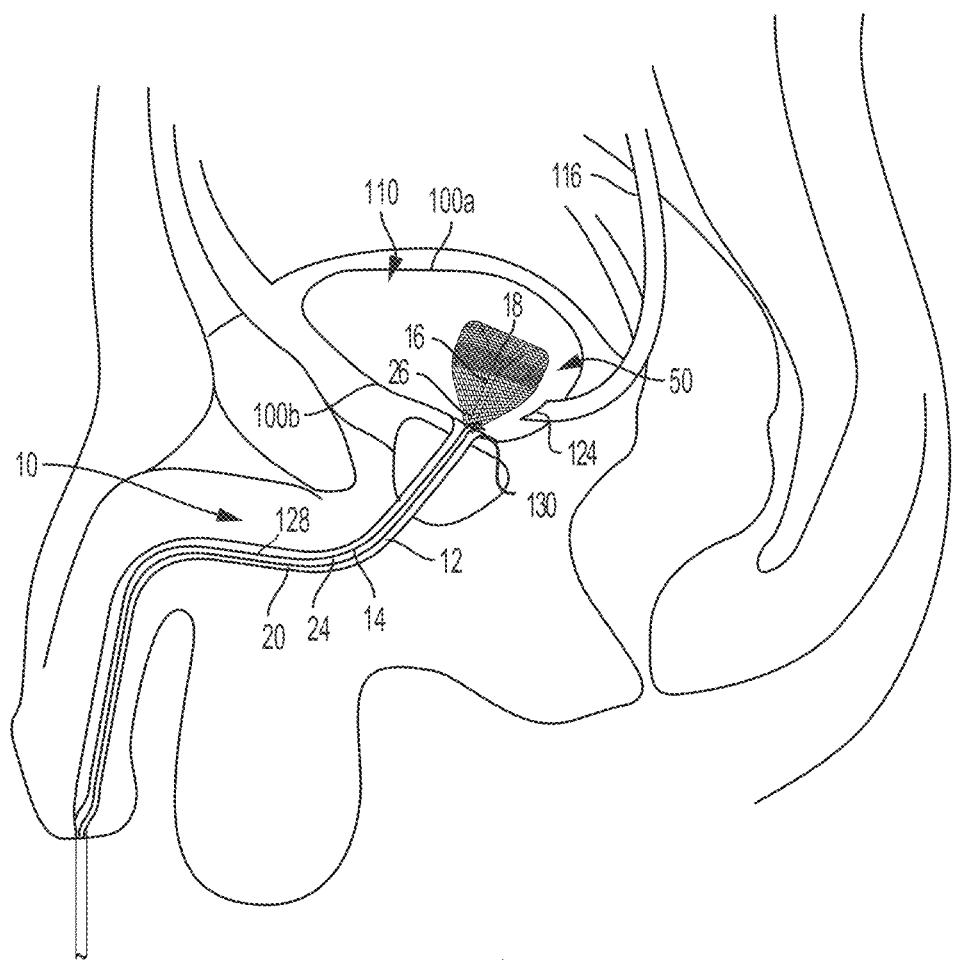
FIG. 1 is a schematic drawing of a urine collection catheter deployed within the bladder of a male patient according to an example of the disclosure.

As used herein, the singular form of "a", "an", and "the" include plural referents unless the context clearly states otherwise.

As used herein, the terms "right", "left", "top", and derivatives thereof shall relate to the invention as it is oriented in the drawing figures. The term "proximal" refers to the portion of the catheter device that is manipulated or contacted by a user and/or to a portion of an indwelling catheter nearest to the urinary tract access site. The term "distal" refers to the opposite end of the catheter device that is configured to be inserted into a patient and/or to the portion of the device that is inserted farthest into the patient's urinary tract. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

For the purposes of this specification, unless otherwise indicated, all numbers expressing quantities of ingredients, reaction conditions, dimensions, physical characteristics, and so forth used in the specification and claims are to be understood as being modified in all instances by the term "about." Unless indicated to the contrary, the numerical parameters set forth in the following specification and attached claims are approximations that can vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all sub-ranges beginning with a minimum value equal to or greater than 1 and ending with a maximum value equal to or less than 10, and all sub-ranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

Fluid retention and venous congestion are central problems in the progression to advanced renal disease. Excess sodium ingestion coupled with relative decreases in excretion leads to isotonic volume expansion and secondary compartment involvement. In some examples, the present invention is generally directed to devices and methods for facilitating drainage of urine or waste from the bladder, ureter, and/or kidney(s) of a patient. In some examples, the present invention is generally directed to devices and methods for inducing a negative pressure in the bladder, ureter, and/or kidney(s) of a patient. While not intending to be bound by any theory, it is believed that applying a negative pressure to the bladder, ureter, and/or kidney(s) can offset the medullary nephron tubule re-absorption of sodium and water in some situations. Offsetting re-absorption of sodium and water can increase urine production, decrease total body sodium, and improve erythrocyte production. Since the intra-medullary pressures are driven by sodium and, therefore, volume overload, the targeted removal of excess sodium enables maintenance of volume loss. Removal of volume restores medullary hemostasis. Normal urine production is 1.48-1.96 L/day (or 1-1.4 ml/min).

Fluid retention and venous congestion are also central problems in the progression of prerenal Acute Kidney Injury (AKI). Specifically, AKI can be related to loss of perfusion or blood flow through the kidney(s). Accordingly, in some examples, the present invention facilitates improved renal hemodynamics and increases urine output for the purpose of relieving or reducing venous congestion. Further, it is anticipated that treatment and/or inhibition of AKI positively impacts and/or reduces the occurrence of other conditions, for example, reduction or inhibition of worsening renal function in patients with NYHA Class III and/or Class IV heart failure. Classification of different levels of heart failure are described in *The Criteria Committee of the New York Heart Association*, (1994), *Nomenclature and Criteria for Diagnosis of Diseases of the Heart and Great Vessels*, (9th ed.), Boston: Little, Brown & Co. pp. 253-256, the disclosure of which is incorporated by reference herein in its entirety. Reduction or inhibition of episodes of AKI and/or chronically decreased perfusion may also be a treatment for Stage 4 and/or Stage 5 chronic kidney disease. Chronic kidney disease progression is described in National Kidney Foundation, K/DOQI *Clinical Practice Guidelines for Chronic Kidney Disease: Evaluation, Classification and Stratification*. Am. J. Kidney Dis. 39:S1-S266, 2002 (Suppl. 1), the disclosure of which is incorporated by reference herein in its entirety.

Figure 2:
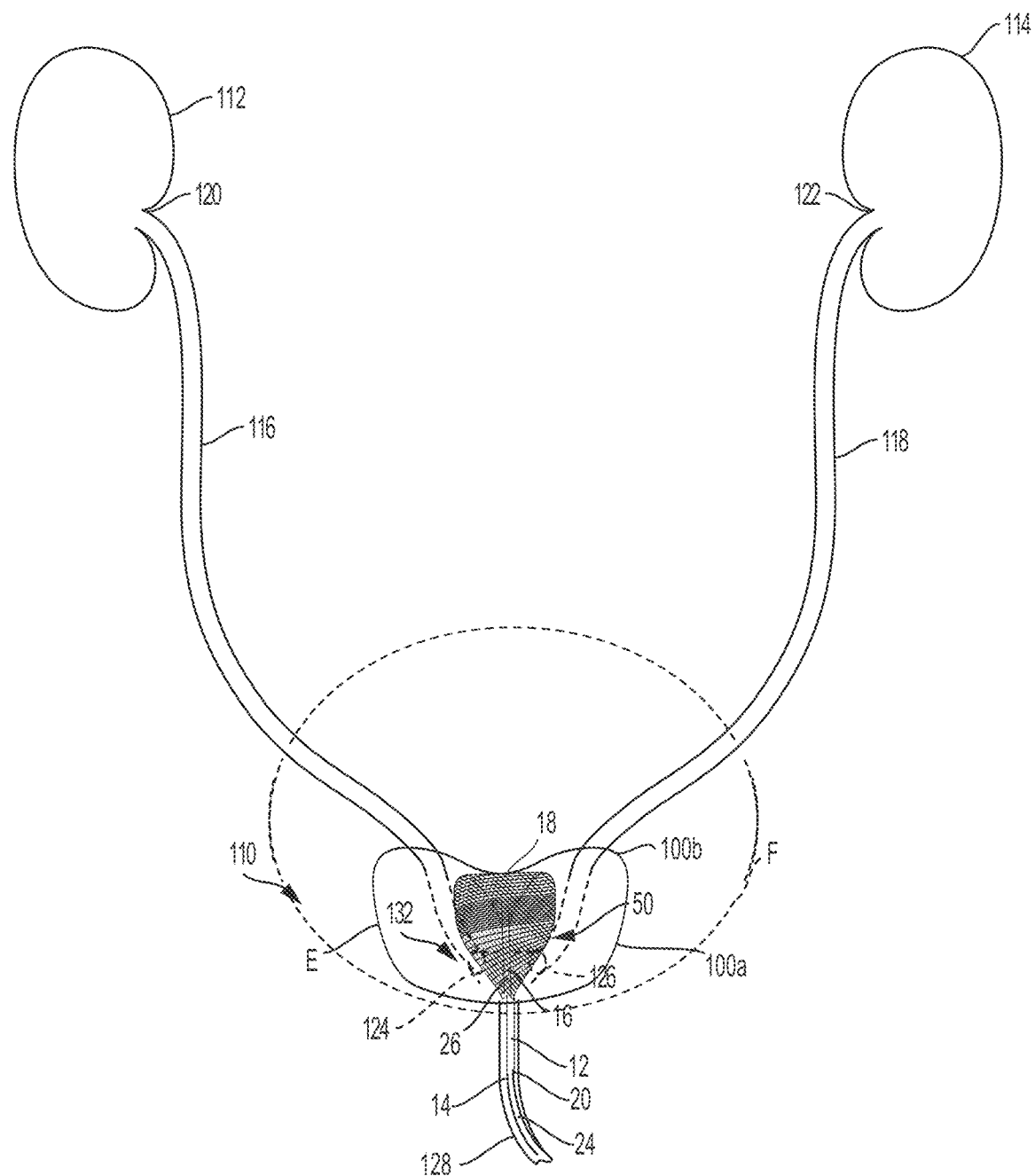
FIG. 2 is another schematic drawing of the urine collection catheter deployed within a patient's bladder according to an example of the disclosure.
Figure 3:
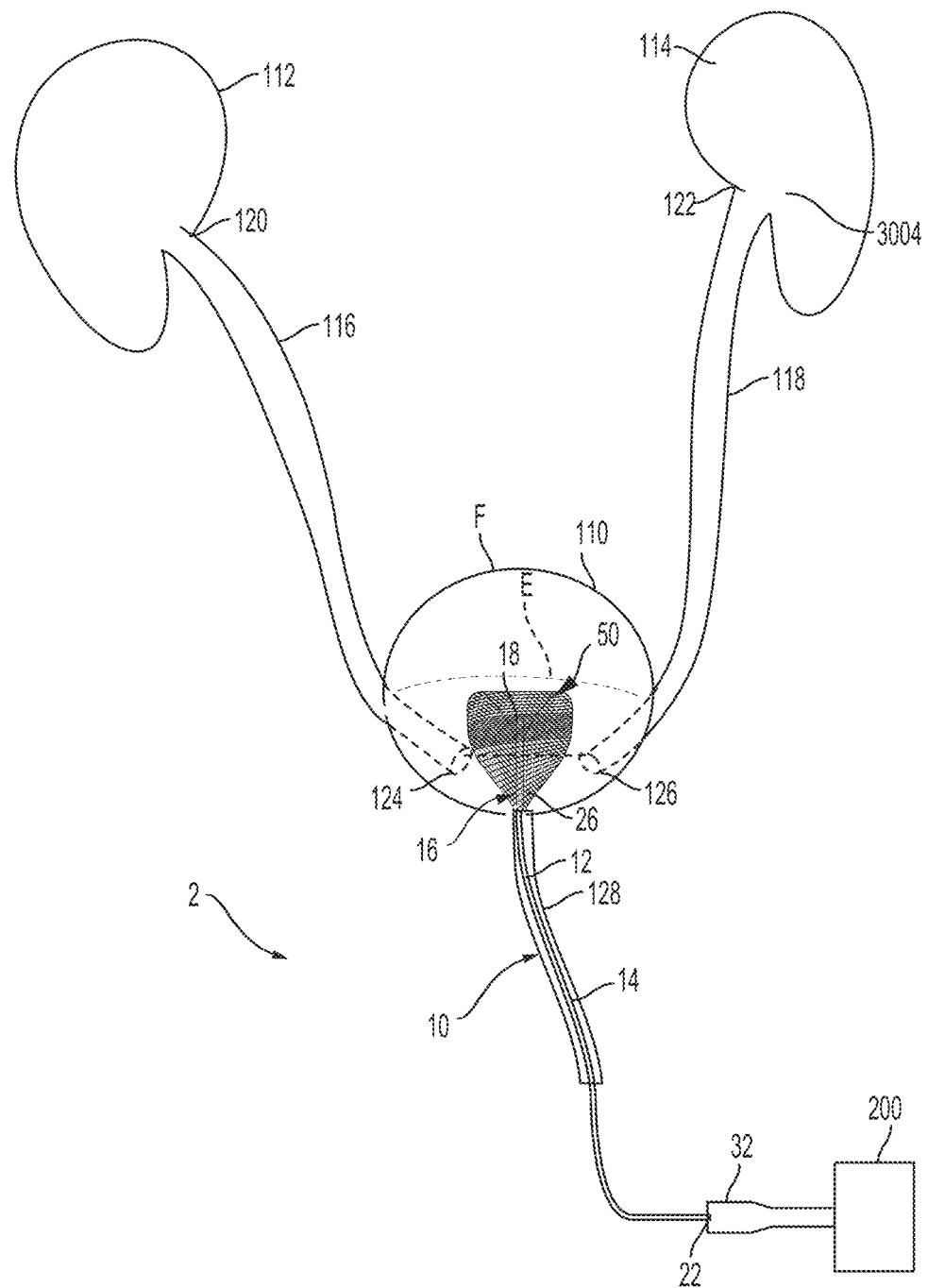
FIG. 3 is a schematic drawing of a urine collection system including a urine collection catheter deployed in a bladder of a patient and a fluid pump for providing negative pressure to the urinary tract according to example of the disclosure.

With reference to FIGS. 1-3, an exemplary system 100 for inducing negative pressure in a urinary tract of a patient for increasing renal perfusion is illustrated. It is noted, however, that the system 2 described herein is but one example of a negative pressure system for inducing negative pressure that can be used with urine collection catheters 10 disclosed herein. The catheters 10 and other elements disclosed herein can also be used with other medical devices for collecting fluid and/or providing negative pressure therapy within the scope of the present disclosure. In addition, in other examples, the urine collection catheters 10 disclosed herein can be connected to an unpressurized fluid collection container.

The system 2 comprises a urine collection catheter 10 deployed in the urinary tract and a pump 200 (shown in FIG. 3) for inducing the negative pressure in the urinary tract through the catheter 10. The patient's urinary tract comprises a patient's right kidney 112 and left kidney 114. The kidneys 112, 114 are responsible for blood filtration and clearance of waste compounds from the body through urine. Urine produced by the right kidney 112 and the left kidney 114 is drained into a patient's bladder 110 through tubules, namely a right ureter 116 and a left ureter 118, which are connected to the kidneys 112, 114 at a renal pelvis 120, 122. Urine may be conducted through the ureters 116, 118 by peristalsis of the ureter walls, as well as by gravity. The ureters 116, 118 enter the bladder 110 through ureter orifices or openings 124, 126. As shown in FIGS. 1-3, the ureteral orifices or openings 124, 126 are positioned at a midline of the bladder 110, approximately half way between an inferior bladder wall 100a and a superior bladder wall 100b (shown in FIG. 2). As such, proximal portions of the ureters 116, 118 are shown in phantom in FIGS. 2 and 3 to indicate that such structures pass behind the bladder 110 and connect to the bladder 110 at the orifices or openings 124, 126.

The ureter orifices or openings 124, 126 are covered by soft tissue which essentially forms a one-way flap valve. When the bladder 110 is collecting urine, the soft tissue is able to accommodate pressure from the peristalsis so that urine can pass from the ureters 116, 118 into the bladder 110. When the bladder 110 contracts to expel urine therefrom, the soft tissue is restrained against the ureter openings 124, 126 to prevent backflow of urine from the bladder 110 back into the ureters 116, 118. As described herein, in some examples, restraints, such as stents, catheters, tubes, and similar structures, can be positioned to allow the ureter openings 124, 126 to remain open during negative pressure therapy so that the negative pressure can draw urine into the bladder 110 and into catheter devices positioned in the bladder 110.

The bladder 110 is a flexible and substantially hollow structure adapted to collect urine until the urine is excreted from the body. The bladder 110 is transitionable from an empty position (signified by reference line E in FIGS. 2 and 3) to a full position (signified by reference line F in FIGS. 2 and 3). Normally, when the bladder 110 reaches a substantially full state, urine is permitted to drain from the bladder 110 to a urethra 128 through a urethral sphincter or opening 130 located at a lower portion of the bladder 110. Contraction of the bladder 110 can be responsive to stresses and pressure exerted on a trigone region 132 (shown in FIG. 2) of the bladder 110, which is the triangular region extending between the ureteral openings 124, 126 and the urethral opening 130. The trigone region 132 is sensitive to stress and pressure, such that as the bladder 110 begins to fill, pressure on the trigone region 132 increases. When a threshold pressure on the trigone region 132 is exceeded, the ureteral sphincter or opening 130 relaxes and allows the bladder 110 to contract to expel collected urine through the urethra 128.

Urine Collection Catheters

The urine collection catheter 10 is shown deployed in the patient's bladder 10 in FIGS. 1-3. Catheters configured to be deployed in other portions of the urinary tract, such as the ureters 116, 118, renal pelvis 120, 122, or kidney(s) 112, 114, including similar support structures and deployment mechanisms to catheter 10 are described elsewhere in the present application.

With continued reference to FIGS. 1-3, the urine collection catheter 110 comprises an elongated tube 12 comprising a proximal portion 14, which can be configured for placement in the urethra 128 of the patient, a distal portion 16 comprising a distal end 18, and a sidewall 20 extending between a proximal end 22 and the distal end 18 of the elongated tube 12 defining at least one drainage lumen 24 extending through the tube 12. The sidewall 20 of the elongated tube 12 comprises a drainage portion 26 which allows fluid to pass through the sidewall 20 and into the drainage lumen 24.

The elongated tube 12 can have any suitable length to accommodate anatomical differences for gender and/or patient size. In some examples, the tube 12 has a length from about 30 cm to about 120 cm. Further, the elongated tube 1002 can have a maximum outer diameter OD of about 0.25 mm to about 10 mm or about 0.33 mm to about 3.0 mm. The elongated tube 12 can also have an inner diameter ID of about 0.1 mm to 9.0 mm or about 0.16 mm to about 2.40 mm. It is appreciated that the outer and inner diameters of the elongated tube 12 can include any of the subranges of the previously described ranges.

The elongated tube 12 can be formed from any suitable flexible and/or deformable material. Such materials facilitate advancing and/or positioning the tube 12 in the bladder 110 or ureters 116, 118. Non-limiting examples of such materials include biocompatible polymers, polyvinyl chloride, polytetrafluoroethylene (PTFE) such as Teflon®, silicon coated latex, or silicon. At least a portion or all of the catheter device 10, particularly the tube 12, can be coated with a hydrophilic coating to facilitate insertion and/or removal and/or to enhance comfort. In some examples, the coating is a hydrophobic and/or lubricious coating. For example, suitable coatings can comprise ComfortCoat® hydrophilic coating which is available from Koninklijke DSM N.V. or hydrophilic coatings comprising polyelectrolyte(s) such as are disclosed in U.S. Pat. No. 8,512,795, which is incorporated herein by reference. In some examples, the tube 12 is impregnated with or formed from a material viewable by fluoroscopic imaging. For example, the biocompatible polymer which forms the tube 12 can be impregnated with barium sulfate or a similar radiopaque material. As such, the structure and position of the tube 12 is visible to fluoroscopy.

The drainage portion 26 of the drainage tube 12 can be provided in a variety of configurations depending on the fluid volume and flow rate intended to be drawn into the drainage lumen 24 from the bladder 110. For example, as shown in FIGS. 4A-7B, the drainage portion 26 comprises at least one fluid port or opening 28 for permitting fluid to flow through the sidewall 20 of the tube 12 into the at least one drainage lumen 24. The drainage port(s) or opening(s) 28 can have any shape desired, such as circular or non-circular, ellipsoid, etc. For example, the opening(s) 28 can be one or more of a circular shape, an elliptical shape, a square shape, a regular polygonal shape, an irregular circular shape, or an irregular polygonal shape, or combinations thereof. The port(s) or opening(s) 28 can be have an area of between about 0.02 sq. inches to about 1.0 sq. inches or more. In other examples, the drainage portion 26 of the elongated tube 12 comprises a perforated portion of sidewall 20 comprising a plurality of perforations.

Desirably, the perforations or fluid openings 28 are positioned so that negative pressure provided to the bladder 110 through the drainage lumen 24 is evenly distributed through the bladder 110. In some examples, the perforations or openings 28 are positioned so that negative pressure is provided from the drainage lumen 24 of the elongated tube 12 in all directions (e.g., so that a 360 degree negative pressure is provided to the bladder 110). In some examples, a diameter of the openings 28 and/or perforations 30 can range from about 0.005 mm to about 1.0 mm. The configuration of each perforations or opening 28 can be the same or different, as desired. The perforations or openings 28 can be spaced in any arrangement, for example, linear or offset. In some examples, each port or perforation can be circular or non-circular. In other examples, the drainage portion 26 comprises a mesh material, for example, formed from a woven filament and comprising a plurality of openings for conducting fluid from the bladder 110 into the drainage lumen 24 of the tube 12.

With specific reference to FIG. 3, aspects of the proximal portion 14 of the elongated tube 12 and external elements of the system 2 are described. The proximal portion 14 of the tube 12 is configured for placement in a portion of the urinary tract proximal to the bladder, such as the urethra 128. Proximal portions of the elongated tube 12 can also extend from the body and, for example, can be connected to a fluid collection container or to the pump 200. In some examples, the proximal portion 14 of the tube 12 is essentially free of or free of openings or perforations. While not intending to be bound by any theory, it is believed that when negative pressure is applied at the proximal portion 14 of the tube 12, that openings in the proximal portion of the tube 12 may be undesirable as such openings may diminish the negative pressure at the distal portion 16 of the urine collection catheter 10 and thereby diminish the draw or flow of fluid or urine from the kidney 112, 116, and renal pelvis 120, 122. It is desirable that the flow of fluid from the ureter 114, 116 and/or kidney 112, 114 is not prevented by occlusion of the ureter 116, 118 and/or kidney 112, 114 by the catheter 10.

In some examples, the proximal end 22 of the tube 12 comprises and/or is connected to a port 32 (shown in FIG. 3) for attaching the catheter 10 to the pump 200. The connection between the tube 12 and the pump 200 or another fluid collection container can be a standard connection mechanism, such as a luer lock or snap fit connection. In other examples, a dedicated or customized connector or connection device can be used for connecting the proximal end of the catheter device 10 or port 32 to other elements of the fluid collection system. In some examples, the customized connector can be structured to prevent a user from connecting the catheter 10 to unsuitable pressure sources. For example, the customized connector may be sized to prevent a user from connecting the catheter 10 to sources of wall suction or other sources of elevated vacuum pressures.

As described in further detail in connection with FIGS. 13-14B, the fluid pump 200 (shown in FIG. 3) is configured to generate a negative pressure to extract urine from the patient's urinary tract. In some examples, the pump 200 may also generate a positive pressure and, for example, may be configured to alternate between providing negative pressure, positive pressure, and equalizing pressure to atmosphere based on a selection from a user or automatically according to a predetermined schedule. The pump 200 can be configured to provide a low level negative pressure of 100 mmHg or less to a proximal end of the catheter 10. In some examples, the pump 200 can be configured to operate at a number of discrete pressure levels. For example, the pump 200 may be configured to operate at pressure levels of 15 mmHg, 30 mmHg, and 45 mmHg. A user can select one of the pressure levels using a switch, dial, or controller as are known in the art.

A commercially available pump which can be adapted for use with the system 10 is the Air Cadet Vacuum Pump from Cole-Parmer Instrument Company (Model No. EW-07530-85). The pump 200 can be connected in series to the regulator, such as the V-800 Series Miniature Precision Vacuum Regulator—1/8 NPT Ports (Model No. V-800-10-W/K), manufactured by Airtrol Components Inc. Pumps which can be adapted for use with the system 200 are also available from Ding Hwa Co., Ltd (DHCL Group) of Dacun, Changhua, China.

In other non-limiting examples, at least a portion of the pump 200 can be positioned within the patient's urinary tract, for example within the bladder 110. For example, the pump 200 can comprise a pump module and a control module coupled to the pump module, the control module being configured to direct motion of the pump module. At least one (one or more) of the pump module, the control module, or the power supply may be positioned within the patient's urinary tract. The pump module can comprise at least one pump element positioned within the fluid flow channel to draw fluid through the channel. Some examples of suitable pump assemblies, systems and methods of use are disclosed in U.S. Patent Application No. 62/550,259, entitled "Indwelling Pump for Facilitating Removal of Urine from the Urinary Tract", which is incorporated by reference herein in its entirety.

Tissue Support Structure

Having described elements of the urine collection catheter 10 and pump 200, various structures for maintaining the distal portion 16 and distal end 18 of the elongated tube 12 at a desired position in the bladder, ureter, or other positions in the urinary tract will now be discussed in detail. In particular, with reference to FIGS. 4A-7B, the urine collection catheter 10 further comprises a permeable tissue support 50 directly or indirectly connected to the distal portion 16 of the elongated tube 12 and extending axially (e.g., in a direction of arrow A1 in FIG. 4A) and/or radially (e.g., in a direction of arrow A2 in FIG. 4A) therefrom. As used herein, the tissue support 50 is directly connected to the elongated tube 12 when portions of the tissue support connect or are adhered to the tube 12. The tissue support 50 is indirectly connected to the tube 50, when it is connected through another fastener, element, or component, such as a sleeve, bracket, or collar, as are known in the art. The tissue support 50 is configured to be deployed in the patient's urinary tract to maintain the distal end 18 of the elongated tube 12 at a predetermined position in the urinary tract. For example, as shown in FIGS. 1-3, the tissue support 50 is deployed in the patient's bladder 110. In other examples of a urine collection catheter, the tissue support 50 can be deployed, for example, in the ureter(s) 116, 118, renal pelvis 120, 122, or kidney(s) 112, 114 of the patient. When deployed in the bladder, the permeable tissue support 50 can have a maximum outer diameter D1 (in FIG. 4A) of from about 10 mm to about 100 mm or about 25 mm to 50 mm and a longitudinal length L1 (in FIG. 4A) of about 10 mm to 100 mm or about 25 mm to 50 mm. In one example, in a retracted position, the tissue support is about 8 to about 16 Fr (e.g., about 2.5 mm to about 5 mm) and in the deployed position is from 10 mm to 100 mm.

When deployed, the permeable tissue support 50 defines a three-dimensional shape of sufficient size to permit flow of at least a portion of fluid from the patient's urinary tract through the tissue support 50 and drainage portion 26 of the elongated tube 12 to the at least one drainage lumen 24. For instance, when deployed in the bladder 110, the tissue support 50 can be configured to inhibit mucosal or uroendothelium tissue of the bladder 110 from occluding at least a portion of the tissue support 50 or drainage portion 26 of the tube 12. When deployed in other portions of the urinary tract, the tissue support 50 can be sized to maintain patency of fluid through the tissue support 50 to the drainage portion 26 of the tube 12 in a patient's kidney(s) 112, 114, ureter(s) 116, 118, and/or in the renal pelvis 120, 122.

When configured to be deployed in the bladder 110, the three-dimensional shape enclosed by the tissue support 50 has a volume of from about 10 cm³ to about 500 cm³. When used in the ureter(s) 116, 118, renal pelvis 120, 122, or kidney 112, 114, the volume of the tissue support 50 is from about 0.10 cm³ to about 100 cm³. As used herein, the three-dimensional shape is defined as a regular shape (e.g., a sphere, cylinder, pyramid, cube, or triangular prism) defined by outer surfaces of the tissue support 50. For example, if the tissue support 50 comprises a spherical outer surface (e.g., a spherical balloon) having a radius (r), then a volume (V) of the three dimensional shape is $$V = \frac{4}{3}\pi r^3.$$

In a similar manner, a tissue support 50 formed by axially or radially extending filaments or wires which outline a sphere of radius (r) also has a volume (V) of $$V = \frac{4}{3}\pi r^3,$$

even when the tissue support 50 is not a fully enclosed shape.

When deployed, the permeable tissue support 50 is configured to maintain a volume of the three dimensional shape when portions of the urinary tract contract around the tissue support 50. For example, when an interior of the bladder 110 is exposed to an internal negative pressure, portions of the superior and inferior bladder walls 100a, 100b contract and come into contact with the tissue support 50. The tissue support 50 should provide sufficient structure to prevent or inhibit such portions of the bladder wall 100a, 100b from occluding the ureters 116, 118 and ureteral orifices or openings 124, 126 so that fluid and urine continue to travel through the ureters 126, 128 and into the bladder 110. In a similar manner, the ureteral orifices or openings 124, 126 and ureters 126, 128 should remain open so that internal negative pressure applied in the bladder 110 is transferred from the bladder 110, through the ureters 116, 118 and to the kidneys 112, 114. As discussed above, while not intending to be bound by theory, it is believed that applying internal negative pressure to the kidneys 112, 114 induces urine production to achieve desired therapeutic results. In view of the need to maintain open fluid flow into the bladder 110, a shape and size of the deployed tissue support 50 is selected to prevent portions of the bladder 110 in proximity to the ureteral orifices or openings 124, 126 from collapsing or occluding. For example, the tissue support 50 can be shaped so that, when deployed, a widest portion of the tissue support 50 is adjacent to the orifices or openings 124, 126 to prevent such portions of the bladder 110 from collapsing.

The tissue support 50 also desirably provides sufficient structural support so that openings 28 of the drainage portion 26 of the tube 12 are not occluded by tissues of the bladder wall when negative pressure is delivered to the bladder. Specifically, as described above, while not intending to be bound by theory, it is believed that upon delivery of negative pressure, the bladder wall contracts around the tissue support 50, as shown by the empty bladder E in FIGS. 2 and 3. The tissue support 50 should provide sufficient structure to resist such contraction to prevent or inhibit portions of the bladder wall from collapsing the tissue support 50 and contracting against the drainage portion 26 of the tube 12, which would prevent fluid and urine from flowing through the tissue support 50 and into the drainage lumen 24 of the tube 12. Further, in some examples, the tissue support 50 is desirably formed from a material that does not appreciably abrade, irritate, or damage a mucosal lining of the bladder wall or other portions of the urinary tract when positioned adjacent to the mucosal lining of the bladder wall or the urethra.

In addition to providing sufficient structural support to maintain patency of fluid or urine from the kidneys 112, 116 through the ureter(s) 116, 118, and bladder 100, and into the drainage lumen 24 of the tube 12, the permeable tissue support 50 is also formed from a material capable of permitting fluid to pass therethrough. More specifically, as used herein, a permeable support is a support which permits fluid, such as urine, to pass from a portion of urinary tract, such as the bladder 110, through the tissue support 50 and into the drainage lumen 24 of the drainage tube 12.

In some examples, in order to provide such permeability, the permeable tissue support 50 is formed from one of biocompatible polymer fiber(s); metallic fiber(s), porous film(s), film(s) comprising one or more apertures, fabric(s), or any combination thereof. The support generally has a thickness of from about 0.5 mm to about 5 mm. In other examples, the permeable tissue support 50 comprises plurality of elongated members, such as wire filaments 52, having a first end 54 and/or a second end 56 connected to the elongated tube 12 and woven together to form a wire filament mesh. The elongated members or wire filaments 52 can be formed from any suitable material which provides sufficient structural support to prevent tissues of the urinary tract from occluding the drainage portion 26 of the tube 12, such as one or more of biocompatible plastics, such as polyethylene, and/or metal, such as nitinol. In one example, the elongated members or wire filaments 52 are a nitinol monofilament wire. The filament may have a diameter of about 25 µm to about 5 mm or about 100 µm to about 1.5 mm. In some examples, an outer surface of the tissue support 50 is primarily formed from a continuous surface, as is the case for a support 50 formed from a film with only a small number of openings for permitting fluid to pass through the support 50 toward the drainage portion 26. In other examples, such as in embodiments formed from a wire filament mesh, the tissue support is primarily an open structure in which only a small portion of the outer surface of the support 50 is covered by wire filaments 52. In either case, desirably, a total surface area of openings of the tissue support member is at least equal to a total surface area of the opening 28 or perforations 30 of the drainage portion 26 of the tube 12 to permit sufficient fluid flow into the drainage lumen 14.

The tissue support 50 can be mounted to the tube 12 using a variety of different types of fasteners, adhesives, brackets, and other mechanisms. For example, the tissue support 50 can be connected to the elongated tube 12 by one or more mechanical connectors, such as an annular collar 58, 60 or cap. In that case, portions of the mesh, such as wire filaments or elongated members 52, are crimped against the elongated tube 12 at a desired position and locked in place by the collar 58 or cap. In this way, the collar 58, 60 effectively mounts the crimped portions of the elongated members or wire filaments 52 to the tube 12, thereby fixedly attaching the elongated members or wire filaments 52 to the tube 12.

In other examples, wire filaments 52 of the tissue support 50 can be connected to the tube 12 through the collar 58. In that case, the collar 58 can be configured to slide along the elongated tube 12 to deploy the tissue support 50 and/or to adjust sizing of the tissue support 50 by sliding the collar 58 toward the distal end 18 of the tube 12 (to increase a maximum outer diameter of the tissue port) or proximally to retract or reduce the maximum outer diameter of the tissue support.

Figure 4A:
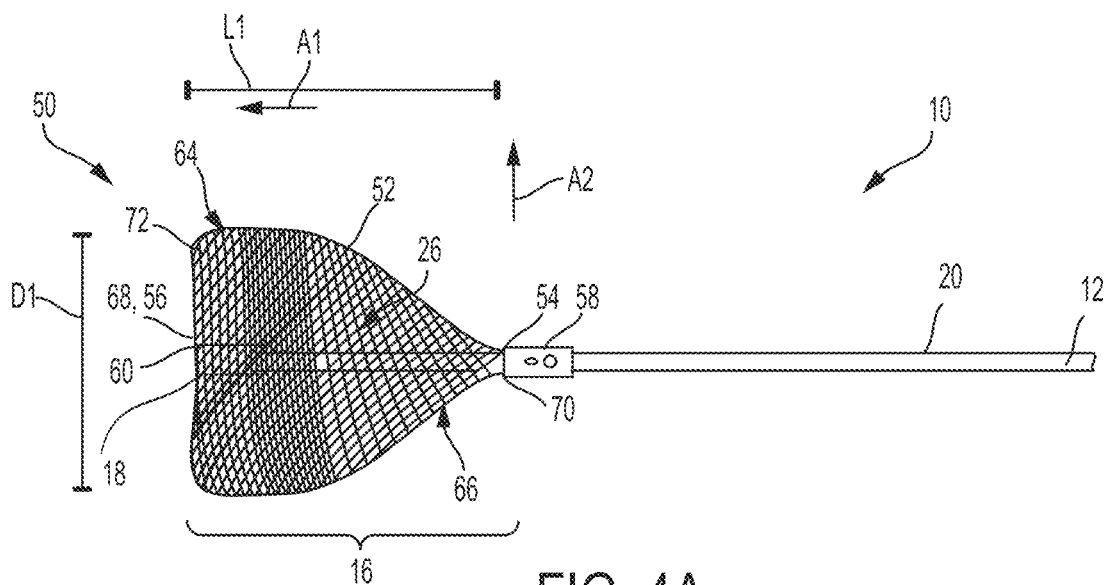
FIG. 4A is a side view of a urine collection catheter according to an example of the present disclosure.
Figure 4B:
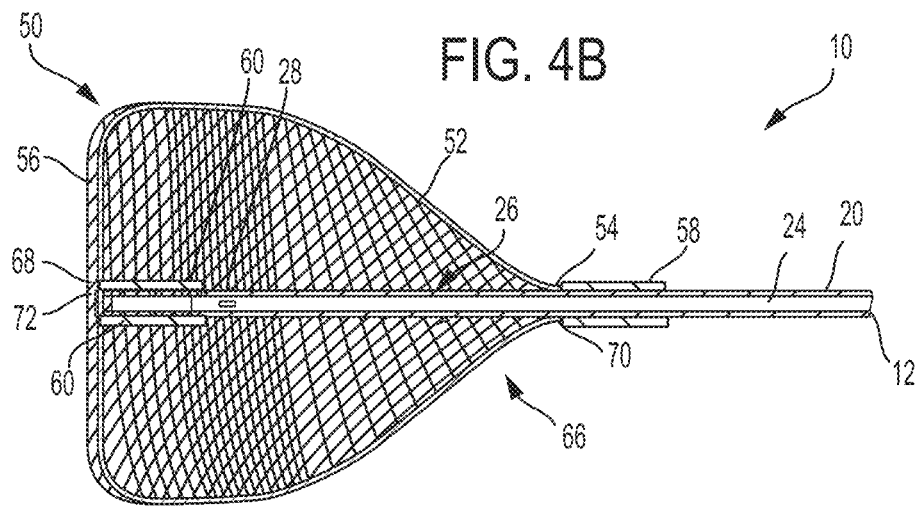
FIG. 4B is a cross-section view of the urine collection catheter of FIG. 4A.

In order to facilitate placement and removal of the urine collection catheter 10, the permeable tissue support 50 is configured to transition from a retracted position (shown in FIG. 5B) to a deployed position (shown in FIGS. 4A, 4B, and 5A). For example, the tissue support 50 can be maintained in a retracted position by a delivery catheter 90. The delivery catheter 90 generally comprises a tubular structure sized to receive at least a portion of the elongated tube 12 and the tissue support 50. The delivery catheter 90 may comprise a proximal end (not shown) configured to be located outside of the body, an open distal end 92 configured to be advanced through the urinary tract to the urethra or bladder 110, and a sidewall 94 expending therebetween. As was the case with the elongated tube 12, the length of the delivery catheter 90 is variable depending on age and gender of the patient. Generally, a length of a sterile portion of the delivery catheter 90 is about 1 in to 3 inches for women, to about 20 inches for men. The total length of the delivery catheter 90 including sterile and non-sterile portions can be several feet. The diameter of the delivery catheter 90 is generally slightly larger than the outer diameter of the elongated tube 12. For example, the delivery catheter 90 may be about 10 Fr to about 26 Fr. When retracted, the tissue support 50 is radially compressed such that an outer diameter of the retracted tissue support 50 is defined by an inner diameter ID of the delivery sheath or catheter 90, as shown in FIG. 5B.

As described in further detail in connection with FIGS. 9 and 10, the catheter 10 and tissue support 50 are deployed through the delivery catheter 90. Specifically, the tissue support 50 is maintained in its retracted position by the delivery catheter 90 and is advanced through the urinary tract to the bladder. In the bladder, the delivery catheter 90 is retracted to release the tissue support 50. Once the tissue support 50 is clear of the open distal end 92 of the delivery catheter 90 it can be biased to adopt the deployed position. At this point, the tissue support 50 generally floats freely within the bladder 110. When negative pressure is applied to the bladder 110, portions of the bladder wall are drawn against the tissue support 50. The bladder wall is prevented from occluding the drainage portion 26 of the elongated tube 12 by the tissue support 50. When ready to remove the distal portion 16 of the catheter 10 from the patient's bladder 110, a user retracts the tissue support 50 into the delivery catheter 90 causing the tissue support 50 to return to its retracted position. Once in the retracted position and enclosed in the delivery catheter 90, the user draws the delivery catheter 90 and urine collection catheter 10 from the urinary tract by, for example, pulling the delivery catheter 60 and structures contained therein through the urethra and from the body.

In other examples, the urine collection catheter 10 can include concentric slidable elongated tubes, in which a first portion of the tissue support 50 is mounted to a first or inner tube and a second portion of the tissue support is mounted to a second or outer tube. In that case, extending the inner tube through an open distal end of the outer tube causes deployment of the tissue support 50. Retracting the inner tube back into the outer tube causes the tissue support 50 to retract.

Having described the general structure of portions of the catheter 10 including the elongated tube 12 and tissue support 50, specific shapes of tissue supports 50 which can be used when providing negative pressure therapy to a patient will now be described in detail. As shown in FIGS. 4A-7B, these structures are each formed from elongated members or flexible wires 52 woven together to form a tissue support 50 having sufficient structural strength to counteract forces exerting by a contracting bladder 110 and sufficient permeability such that fluid or urine passes through the tissue support 50 and to the drainage portion 26 of the elongated tube 12.

In some examples, as shown in FIGS. 4A and 4B, the tissue support 50 comprises a substantially cylindrical distal portion 64 and tapered proximal portion 66. The substantially cylindrical distal portion 64 defines a substantially flat and circular distal surface 68. The tissue support 50 is formed from a mesh formed from the woven elongated members 52. The embodiment of FIGS. 4A and 4B includes a collar 58 which mounts proximal ends 54 of the elongated members or filament wires 52 to the elongated tube 12 and a collar 60 which mounts distal ends 56 of the elongated members to the tube 12. As shown in FIG. 4B, the drainage portion 26 of the tube extends distally beyond the collar 58 and is at least partially enclosed by the tissue support 50. The drainage portion 26 includes an opening 28. In other examples, as described above, the drainage portion 26 could include multiple openings 28 or perforations. The tissue support 50, shown in FIGS. 4A and 4B, is shown in a retracted state within a drainage catheter 90 in FIG. 5B.

Figure 6A:
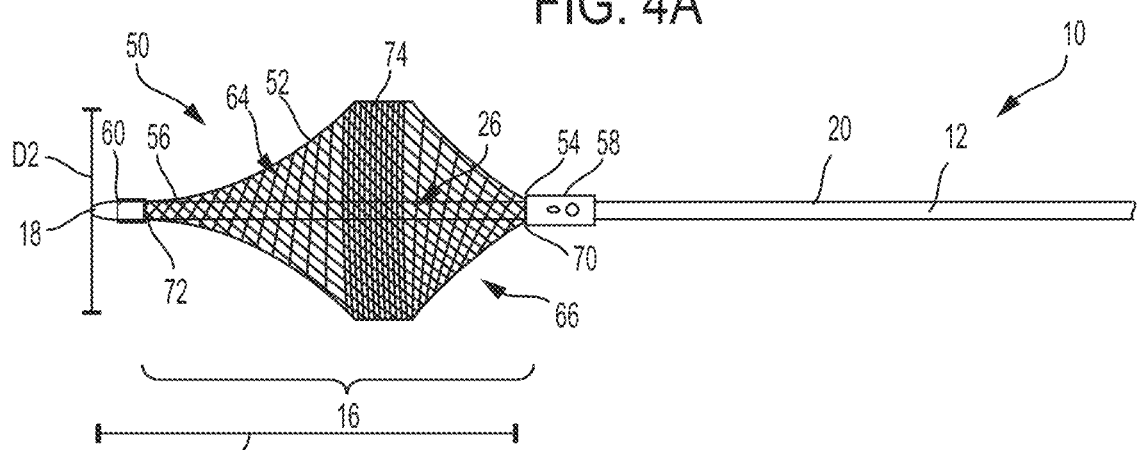
FIG. 6A is a side view of another urine collection catheter according to an example of the present disclosure.
Figure 6B:
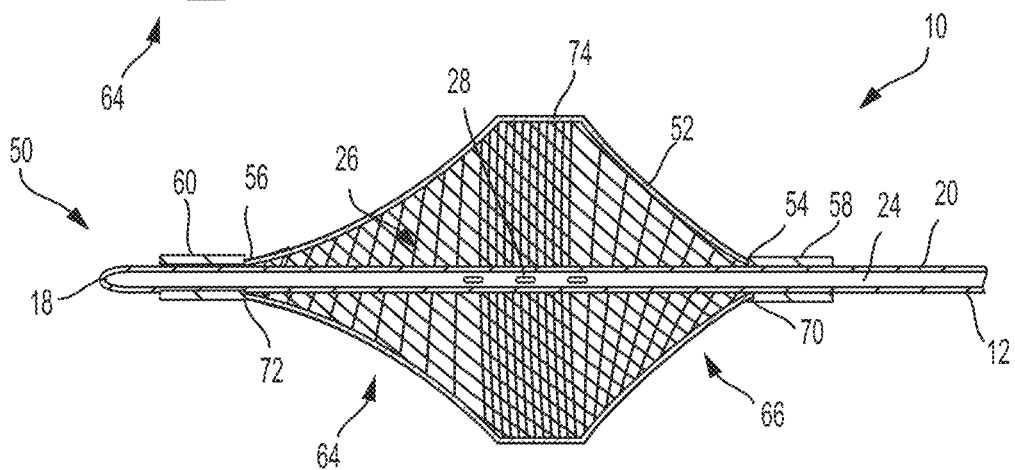
FIG. 6B is a cross-section view of the urine collection catheter of FIG. 6A.

With reference to FIGS. 6A and 6B, another embodiment of a permeable tissue support 50 of a urine collection catheter 10 is illustrated. The tissue support 50 can be formed from elongated members or wire filaments 52 woven together, as in previously described examples. The support 50 includes collars 58, 60 located at both the proximal and distal ends of the tissue support 50. Further, the elongated tube 12 extends through the entire tissue support 50, from a proximal end 70 to a distal end 72 thereof. As shown in FIGS. 6A and 6B, when deployed, a middle portion 74 of the permeable tissue support 50 bulges radially outward from proximal and distal portions 64, 66 thereof, such that an outer diameter of the permeable tissue support 50 increases from the proximal end 70 to the middle portion 74 thereof and decreases from the middle portion 74 to the distal end 72 thereof. A maximum outer diameter D2 of the middle portion 74 of the tissue support 50 can be from 5 mm to 40 mm, when configured to be deployed in the bladder 110. The tissue support 50 can have a longitudinal length L2 of from about 5 mm to about 40 mm. As in previous examples, the drainage portion 26 of the elongated tube 12 including openings 28 is at least partially enclosed by the tissue support 50. In other examples, openings 28 could be replaced by a section of tubing comprising perforations 30 as described previously.

Figure 7A:
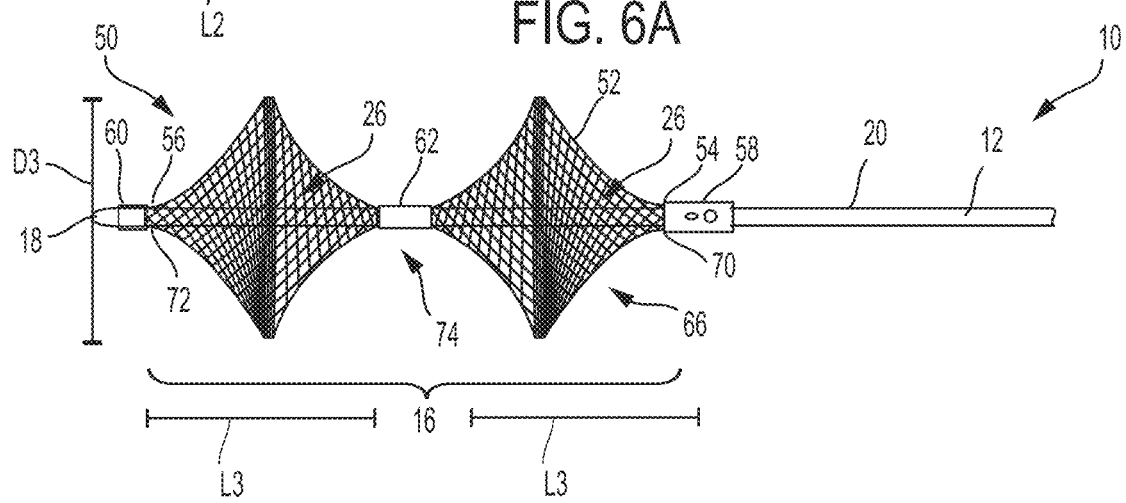
FIG. 7A is a side view of another urine collection catheter according to an example of the present disclosure.
Figure 7B:
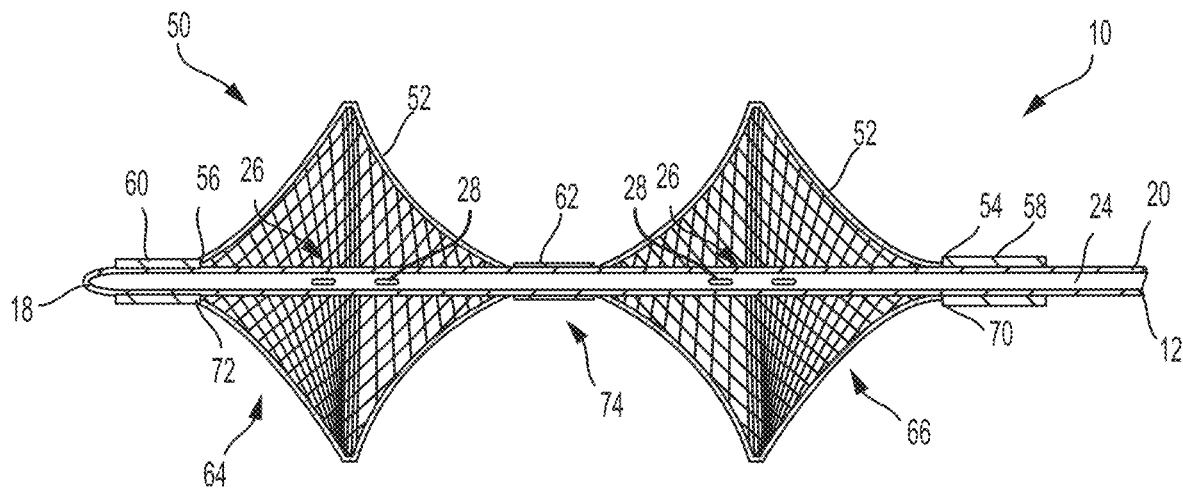
FIG. 7B is a cross-section view of the urine collection catheter of FIG. 7A.

With reference to FIGS. 7A and 7B, in another example, the permeable tissue support 50 comprises a narrow middle portion 74 between wider proximal and distal portions 64, 66. As in previous examples, the tissue support 50 has a maximum outer diameter D3 of from 10 mm to 100 mm, when configured to be deployed in a patient's bladder. In some examples, as shown in FIGS. 7A and 7B, the narrow middle portion 74 has a minimum outer diameter equal to or substantially equal to an outer diameter of the elongated tube 12, such that the distal portion 64 of the tissue support 50 is separate or spaced apart from the proximal portion 66, such that both the proximal portion 66 and the distal portion 64 have a length L3. The length L3 of the portions can be from about 2.5 mm to about 50 mm, when configured to be deployed in the bladder. In the configuration shown in FIGS. 7A and 7B, the tissue support 50 is sized such that, when deployed in the patient's bladder, the distal portion 64 extends beyond the trigone region and ureteral openings of the bladder 110. For example, the distal portion 64 can be sized to support the superior bladder wall when the bladder is empty. The proximal portion 66 can be positioned between the urethral opening and the ureteral openings. In this configuration, the proximal and distal portions 64, 66 provide support for portions of the bladder wall both above and below the ureteral openings. As such, the proximal and distal portions 64, 66 of the tissue support 50, desirably, counteract contraction of both superior and inferior walls of the bladder 110 to prevent portions of the contracted bladder wall from occluding or closing the ureteral orifices or openings.

In some examples, as shown in FIGS. 7A and 7B, the narrow middle portion 74 is formed by a metal collar 62 or crimped portion which holds or attaches middle portions of the elongated members or wire filaments 52 against the elongated tube 12. As such, as shown in FIGS. 7A and 7B, the proximal portion 66 and the distal portion 64 of the tissue support 50 are spaced apart and separated by the collar 62. Drainage portions 26 of the tube 12 can be enclosed in both the proximal and distal portions 64, 66 of the tissue support 50. For example, as shown in FIG. 7B, openings 28 are enclosed by each structure.

In other examples, the woven elongated members or wire filaments 52 may be biased or molded to form the narrow middle portion 74 of the tissue support 50, when the tissue support is deployed. For example, a heat setting process may be applied to the elongated members or wire filaments so that they conform to a desired shape. In some examples, as shown in FIGS. 7A and 7B, the narrow middle portion 74 extends all the way to the elongated tube (e.g., the narrow middle portion 74 has a minimum outer diameter equal to an outer diameter of the elongated tube 12). In other examples, the narrow middle portion 74 is an annular groove extending radially inwardly from other portions of the tissue support 50. For example, the groove may have a depth relative to the maximum outer diameter D3 of the tissue support 50, of from about 2.5 mm to about 10 mm. In a similar manner, the middle annular portion may have a minimum outer diameter of from about 10% to about 99% less than a maximum outer diameter of the permeable tissue support.

Ureteral Stents

As discussed above, the urine collection catheters 10 disclosed herein can be used to apply negative pressure therapy to increase renal perfusion. As such, negative pressure delivered through a urine collection catheter 10 deployed in the bladder 110 must transfer through the ureters 116, 118 to the kidneys 112, 114. In some examples, ureteral stents 352, 354 can be inserted through the ureters 116, 118 to maintain patency of the ureters 116, 118 and to ensure that the ureteral orifices or openings 124, 126 remain open upon application of negative pressure to the bladder.

As used herein, "maintain patency of fluid flow between a kidney and a bladder of the patient" means establishing, increasing or maintaining flow of fluid, such as urine, from the kidneys through the ureter(s), ureteral stent(s) and/or ureteral catheter(s) to the bladder. As used herein, "fluid" means urine and any other fluid from the urinary tract.

Figure 8:
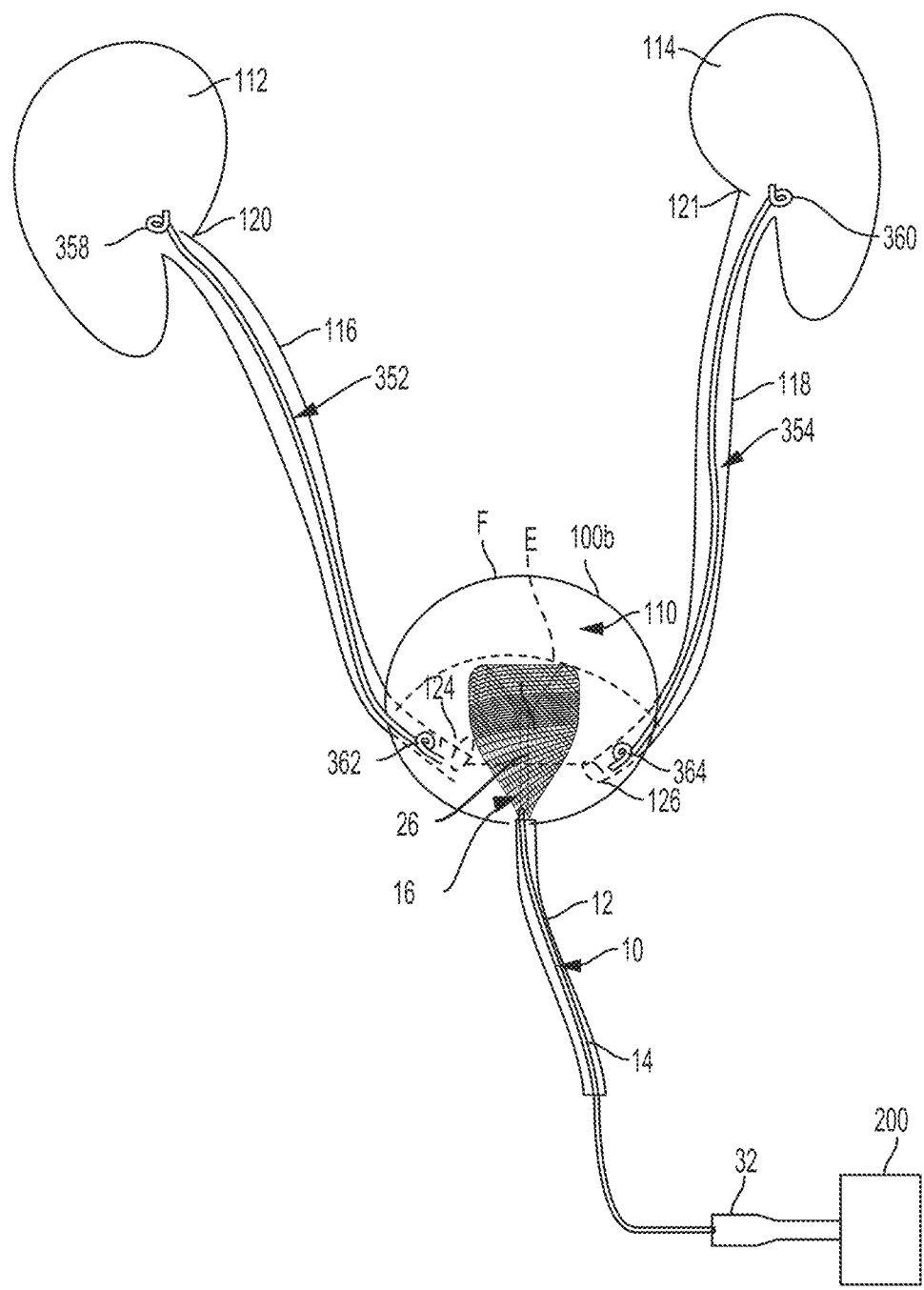
FIG. 8 is a schematic drawing of a urine collection system including a urine collection catheter deployed in a bladder and ureteral stents according to an example of the present disclosure.

An exemplary urine collection system including the urine collection catheter 10, permeable tissue support 50 deployed in the bladder, and the ureteral stents 352, 354 is shown in FIG. 8. The stent 352 is deployed in the right ureter 116, such that a distal end or retention portion of the stent 352 extends to the right kidney 112, or to the renal pelvis 120 adjacent to the right kidney 112. The ureteral stent 354 is deployed in the left ureter 118, such that a distal end of the stent 354 extends to the left renal pelvis 122 or left kidney 114. Typically, these stents 352, 354 are deployed by inserting a stent having a nitinol wire therethrough through the urethra 128 and bladder 110 up to the kidney 112, 114, then withdrawing the nitinol wire from the stent 352, 354, which permits the stent to assume a deployed configuration. Many of the above stents have a planar loop 358, 360 on the distal end (to be deployed in the kidney), and some also have a planar loop 362, 364 on the proximal end of the stent which is deployed in the bladder. When the nitinol wire is removed, the stent assumes the pre-stressed planar loop shape at the distal and/or proximal ends. To remove the stent 352, 354, a nitinol wire is inserted to straighten the stent and the stent is withdrawn from the ureter and urethra.

Some examples of ureteral stents 352, 354 that can be useful in the present systems and methods include CONTOUR™ ureteral stents, CONTOUR VL™ ureteral stents, POLARIS™ Loop ureteral stents, POLARIS™ Ultra ureteral stents, PERCUFLEX™ ureteral stents, PERCUFLEX™ Plus ureteral stents, STRETCH™ VL Flexima ureteral stents, each of which are commercially available from Boston Scientific Corporation of Natick, Mass. See "Ureteral Stent Portfolio", a publication of Boston Scientific Corp., (July 2010), hereby incorporated by reference herein. The CONTOUR™ and CONTOUR VL™ ureteral stents are constructed with soft Percuflex™ Material that becomes soft at body temperature and is designed for a 365-day indwelling time. Variable length coils on distal and proximal ends allow for one stent to fit various ureteral lengths. The fixed length stent can be 6F-8F with lengths ranging from 20 cm-30 cm, and the variable length stent can be 4.8F-7F with lengths of 22-30 cm. Other examples of suitable ureteral stents include INLAY® ureteral stents, INLAY® OPTIMA® ureteral stents, BARDEX® double pigtail ureteral stents, and FLUORO-4™ silicone ureteral stent, each of which are commercially available from C.R. Bard, Inc. of Murray Hill, N.J. See "Ureteral Stents", http://www.bard-medical.com/products/kidney-stone-management/ureteral-stents/ (Jan. 21, 2018), hereby incorporated by reference herein.

The stents 352, 354 can be deployed in one or both of the patient's kidneys or kidney area (renal pelvis or ureters adjacent to the renal pelvis), as desired. Typically, these stents are deployed by inserting a stent having a nitinol wire therethrough through the urethra and bladder up to the kidney, then withdrawing the nitinol wire from the stent, which permits the stent to assume a deployed configuration. Many of the above stents have a planar loop 358, 360 on the distal end (to be deployed in the kidney), and some also have a planar loop 362, 364 on the proximal end of the stent which is deployed in the bladder. When the nitinol wire is removed, the stent assumes the pre-stressed planar loop shape at the distal and/or proximal ends. To remove the stent, a nitinol wire is inserted to straighten the stent and the stent is withdrawn from the ureter and urethra.

Other examples of suitable ureteral stents 352, 354 are disclosed in PCT Patent Application Publication WO 2017/019974, which is incorporated by reference herein. In some examples, as shown, for example, in FIGS. 1-7 of WO 2017/019974 and in FIG. 9 herein (same as FIG. 1 of WO 2017/019974). As shown in FIG. 9, the exemplary ureteral stent 1000 the ureteral stent 1000 can comprise: an elongated body 1001 comprising a proximal end 1002, a distal end 1004, a longitudinal axis 1006, an outer surface 1008, and an inner surface 1010, wherein the inner surface 1010 defines a transformable bore 1011 that extends along the longitudinal axis 1006 from the proximal end 1002 to the distal end 1004; and at least two fins 1012 projecting radially away from the outer surface 1008 of the body 1001; wherein the transformable bore 1011 comprises: (a) a default orientation 1013A (shown on the left in FIG. 9) comprising an open bore 1014 defining a longitudinally open channel 1016; and (b) a second orientation 1013B (shown on the right in FIG. 9) comprising an at least essentially closed bore 1018 or closed bore defining a longitudinally essentially closed drainage channel 1020 along the longitudinal axis 1006 of the elongated body 1001, wherein the transformable bore 1011 is moveable from the default orientation 1013A to the second orientation 1013B upon radial compression forces 1022 being applied to at least a portion of the outer surface 1008 of the body 1001.

Figure 9:
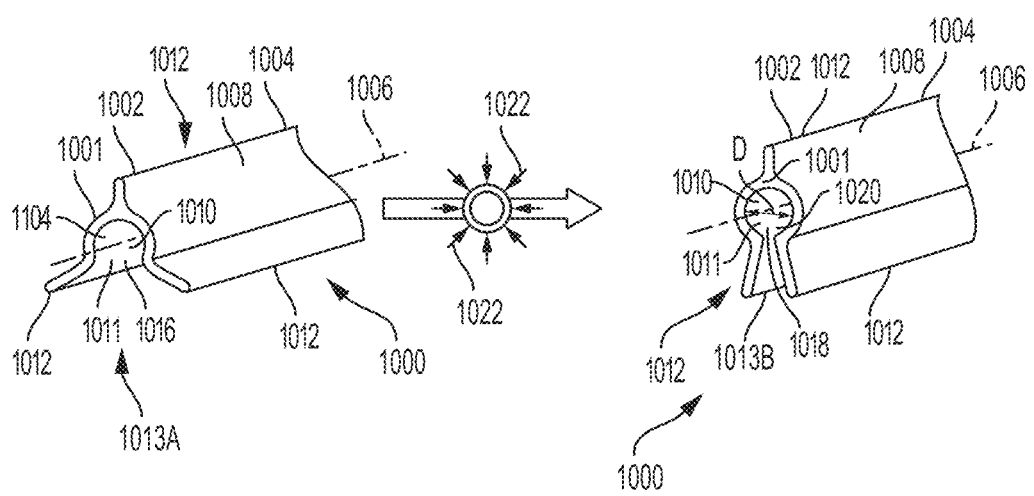
FIG. 9 is a schematic drawing of an exemplary ureteral stent as is known in the prior art.

In some examples, as shown in FIG. 9, the drainage channel 1020 of the ureteral stent 1000 has a diameter D which is reduced upon the transformable bore 1011 moving from the default orientation 1013A to the second orientation 1013B, wherein the diameter is reducible up to the point above where urine flow through the transformable bore 1011 would be reduced. In some examples, the diameter D is reduced by up to about 40% upon the transformable bore 1011 moving from the default orientation 1013A to the second orientation 1013B. In some examples, the diameter D in the default orientation 1013A can range from about 0.75 to about 5.5 mm, or about 1.3 mm or about 1.4 mm. In some examples, the diameter D in the second orientation 1013B can range from about 0.4 to about 4 mm, or about 0.9 mm.

In some examples, one or more fins 1012 comprise a flexible material that is soft to medium soft based on the Shore hardness scale. In some examples, the body 1001 comprises a flexible material that is medium hard to hard based on the Shore hardness scale. In some examples, one or more fins have a durometer between about 15 A to about 40 A. In some examples, the body 1001 has a durometer between about 80 A to about 90 A. In some examples, one or more fins 1012 and the body 1001 comprise a flexible material that is medium soft to medium hard based on the Shore hardness scale, for example having a durometer between about 40 A to about 70 A.

In some examples, one or more fins 1012 and the body 1001 comprise a flexible material that is medium hard to hard based on the Shore hardness scale, for example having a durometer between about 85 A to about 90 A.

In some examples, the default orientation 1013A and the second orientation 1013B support fluid or urine flow around the outer surface 1008 of the stent 1000 in addition to through the transformable bore 1011.

In some examples, one or more fins 1012 extend longitudinally from the proximal end 1002 to the distal end 1004. In some examples, the stent has two, three or four fins.

In some examples, the outer surface 1008 of the body has an outer diameter in the default orientation 1013A ranging from about 0.8 mm to about 6 mm, or about 3 mm. In some examples, the outer surface 1008 of the body has an outer diameter in the second orientation 1013B ranging from about 0.5 mm to about 4.5 mm, or about 1 mm. In some examples, one or more fins have a width or tip ranging from about 0.25 mm to about 1.5 mm, or about 1 mm, projecting from the outer surface 1008 of the body in a direction generally perpendicular to the longitudinal axis.

In some examples, the radial compression forces are provided by at least one of normal ureter physiology, abnormal ureter physiology, or application of any external force. In some examples, the ureteral stent 1000 purposefully adapts to a dynamic ureteral environment, the ureteral stent 1000 comprising: an elongated body 1001 comprising a proximal end 1002, a distal end 1004, a longitudinal axis 1006, an outer surface 1008, and an inner surface 1010, wherein the inner surface 1010 defines a transformable bore 1011 that extends along the longitudinal axis 1006 from the proximal end 1002 to the distal end 1004; wherein the transformable bore 1011 comprises: (a) a default orientation 113A comprising an open bore 114 defining a longitudinally open channel 116; and (b) a second orientation 1013B comprising an at least essentially closed bore 1018 defining a longitudinally essentially closed channel 1020, wherein the transformable bore is moveable from the default orientation 1013A to the second orientation 1013B upon radial compression forces 1022 being applied to at least a portion of the outer surface 1008 of the body 1001, wherein the inner surface 1010 of the body 1001 has a diameter D which is reduced upon the transformable bore 1011 moving from the default orientation 1013A to the second orientation 1013B, wherein the diameter is reducible up to the point above where fluid flow through the transformable bore 1011 would be reduced. In some examples, the diameter D is reduced by up to about 40% upon the transformable bore 1011 moving from the default orientation 1013A to the second orientation 1013B.

Other examples of suitable ureteral stents are disclosed in United States Patent Application Publication No. 2002/0183853 A1, which is incorporated by reference herein. In some examples, as shown, for example, in FIGS. 4, 5 and 7 of US 2002/0183853 A1 and in FIGS. 4-6 herein (same as FIGS. 1 of 4, 5 and 7 of US 2002/0183853 A1), the ureteral stent comprises an elongated, body 10 comprising a proximal end 12, a distal end 14 (not shown), a longitudinal axis 15, and at least one drainage channel (for example, 26, 28, 30 in FIGS. 4; 32, 34, 36 and 38 in FIG. 5; and 48 in FIG. 6) that extends along the longitudinal axis 15 from the proximal end 12 to the distal end 14 to maintain patency of fluid flow between a kidney and a bladder of the patient. In some examples, the at least one drainage channel is partially open along at least a longitudinal portion thereof. In some examples, the at least one drainage channel is closed along at least a longitudinal portion thereof. In some examples, the at least one drainage channel is closed along the longitudinal length thereof. In some examples, the ureteral stent is radially compressible. In some examples, the ureteral stent is radially compressible to narrow the at least one drainage channel. In some examples, the elongated body 10 comprises at least one external fin 40 along the longitudinal axis 15 of the elongated body 10. In some examples, the elongated body comprises one to four drainage channels. The diameter of the drainage channel can be the same as described above.

Figure 10A:
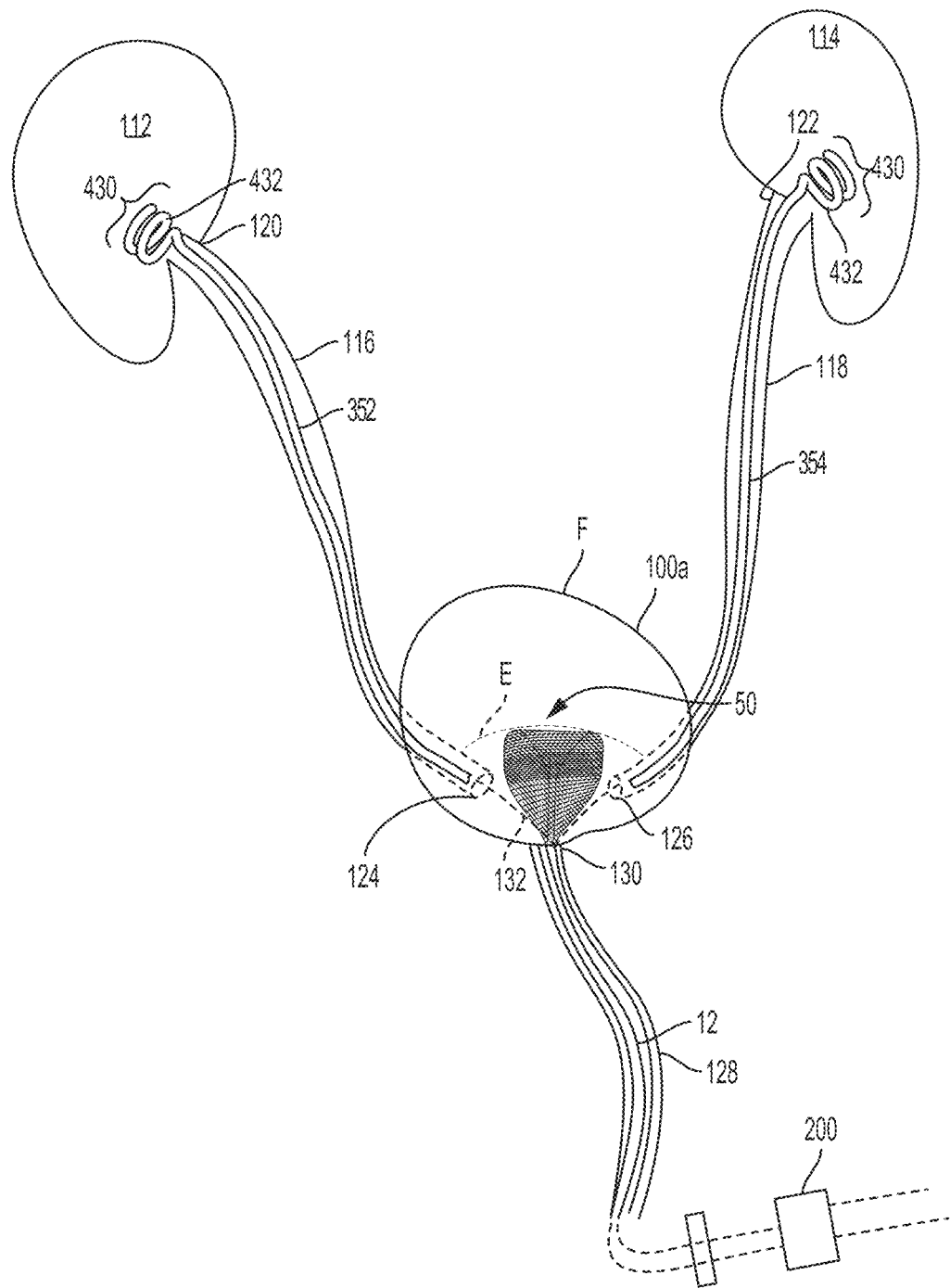
FIG. 10A is a schematic drawing of a urine collection system including a urine collection catheter deployed in the bladder and ureteral stents including a helical retention portion according to an example of the present disclosure.

With reference to FIG. 10A, other embodiments of exemplary ureteral stents 352, 354 which can be used within the scope of the present disclosure to maintain patency of fluid from the kidneys 112, 114 and the ureters 116, 118 to the bladder 110 comprises an elongated tube, which extends from a retention portion located in the bladder. The stents 352, 354 include a helical retention portion 430 comprising a plurality of coils 432 which maintains a distal end the tube in a desired position in a patient's renal pelvis 120, 122 or kidney 112, 114. For example, as described in further detail in connection with FIGS. 10B and 10C, the helical retention portion 432 can comprise at least a first coil having a first diameter; at least a second coil having a second diameter, the first diameter being less than the second diameter, the second coil being closer to an end of the distal portion of the drainage lumen than the first coil; and one or more perforations on a sidewall of the coiled retention portion of the distal portion of the drainage lumen for permitting fluid flow into the drainage lumen. In some examples, the helical stents 352, 354 could be configured such that, prior to insertion into a patient's urinary tract, a portion of the drainage lumen that is proximal to the retention portion defines a straight or curvilinear central axis, and wherein, when deployed, the first coil and the second coil of the retention portion extend about an axis of the retention portion that is at least partially coextensive with the straight or curvilinear central axis of the portion of the drainage lumen.

Figure 10B:
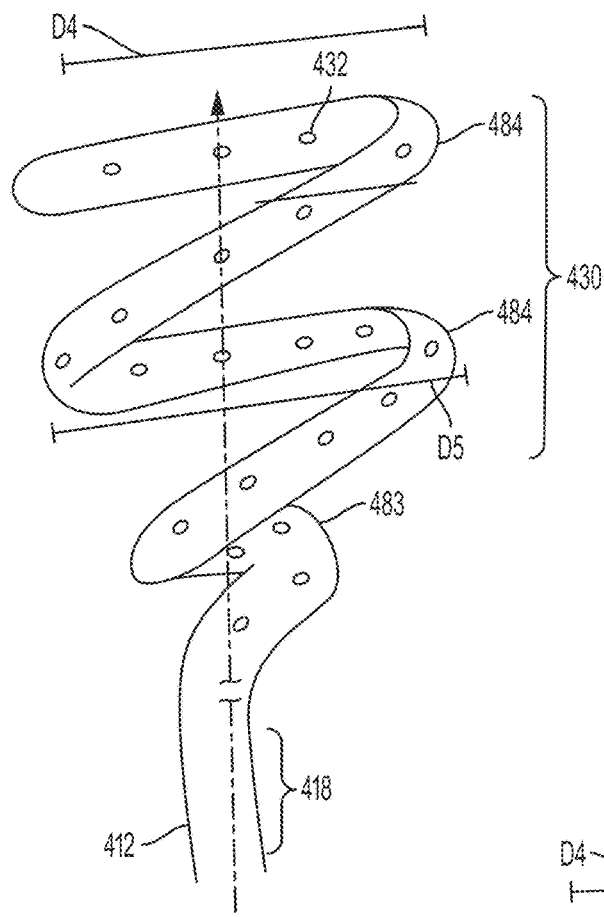
FIG. 10B is a schematic drawing of the helical retention portion of the ureteral stent of FIG. 10A.
Figure 10C:
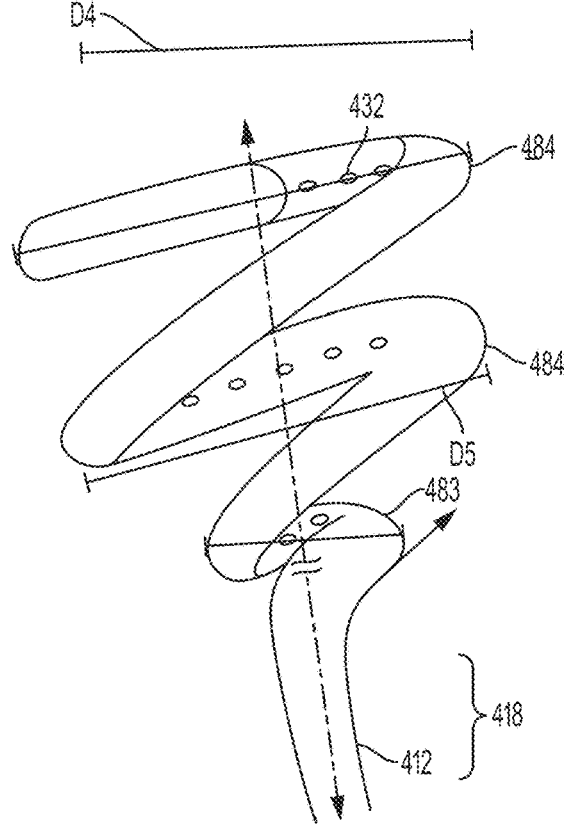
FIG. 10C is a schematic drawing of another embodiment of a helical retention portion of a ureteral stent according to an example of the present disclosure.

As shown in FIGS. 10B and 10C, an exemplary retention portion 430 comprising a plurality of helical coils, which can be used to anchor the ureteral stents disclosed herein are illustrated. The retention portions 430 generally comprise one or more full coils 484 and one or more half or partial coils 483. The retention portion 430 is capable of moving between a contracted position and the deployed position with the plurality of helical coils. For example, a substantially straight guidewire can be inserted through the retention portion 430 to maintain the retention portion 430 in a substantially straight contracted position. When the guidewire is removed, the retention portion 430 can transition to its coiled configuration. In some examples, the coils 483, 484 extend radially and longitudinally from the distal portion 418 of the tube 412. In a preferred exemplary embodiment, the retention portion 430 comprises two full coils 484 and one half coil 483. The outer diameter of the full coils 484, shown by line D4, can be about 18±2 mm. The half coil 483 diameter D5 can be about 14 mm±2 mm. The retention portion 430 can further comprise the one or more drainage holes 432 configured to draw fluid into an interior of the elongated tube 412 of the stent.

Ureteral Catheters

Figure 11:
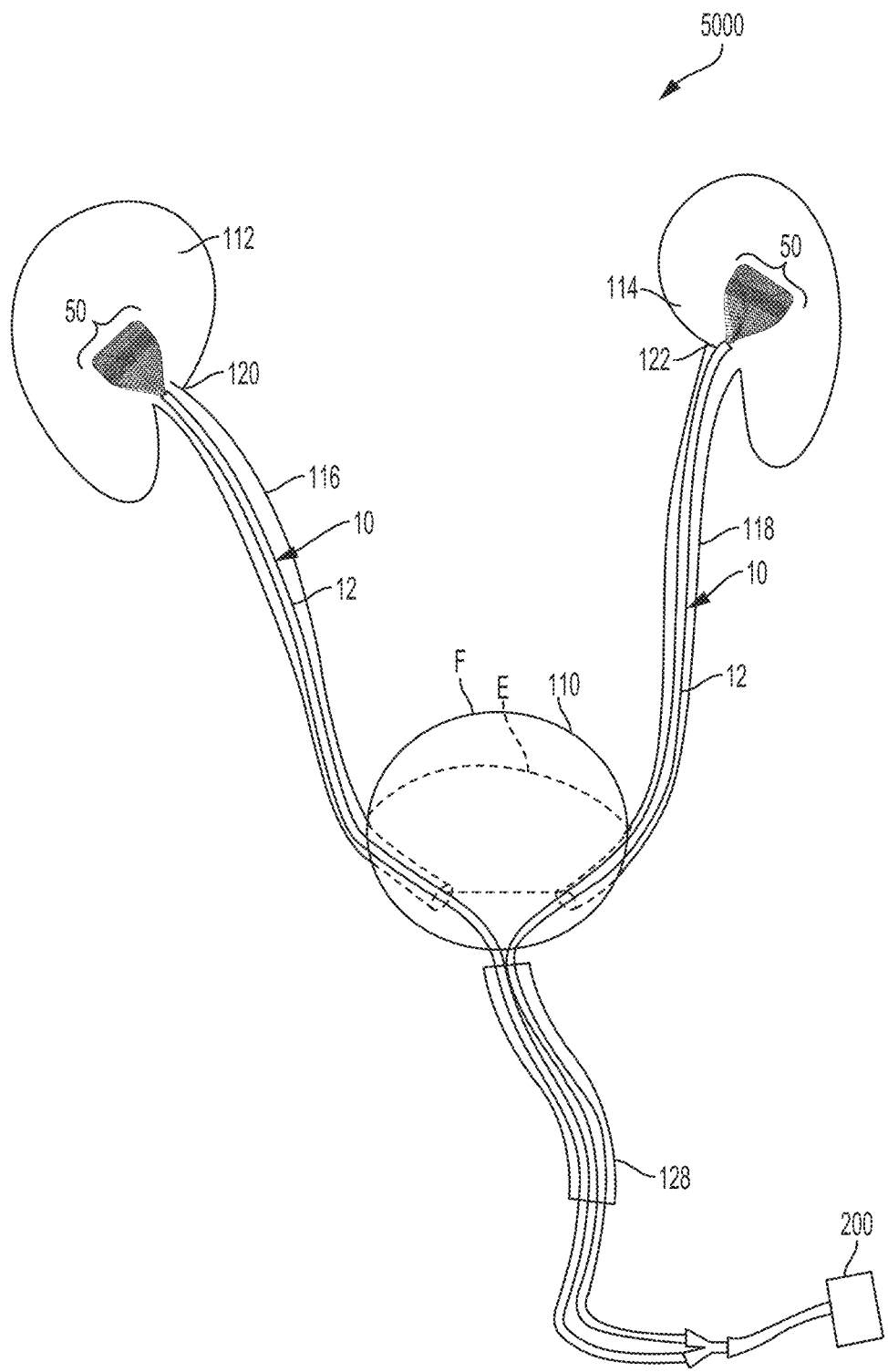
FIG. 11 is a schematic drawing of a urine collection system including urine collection catheters deployed in the renal pelvis or kidney of a patient according to an example of the present disclosure.

The urine collection catheter 10 tissue support 50 disclosed herein and described in detail in connection with FIGS. 1-7B can also be adopted for use as a ureteral catheter in which the tissue support 50 is deployed in the renal pelvis 120, 122 or kidney 112, 114 adjacent to the renal pelvis 120, 122. The elongated tube 12 can extend from the tissue support 50, through the patient's ureter 116, 118, bladder 110, urethra 128, and from the body as shown in FIG. 11. The ureteral catheters can be connected to the pump 200 using conventional connectors, such as luer fittings, snap connectors, and similar mechanisms, as are known in the art. In other examples, as shown in FIG. 11, the ureteral catheters 10 can be connected to the pump 200 through a y-connector.

In order to adopt the urine collection catheters 10 disclosed above for use as ureteral catheters, the dimensions of the catheter 10 and tissue support 50 are adjusted to fit within the renal pelvis and/or kidney adjacent to the renal pelvis. In addition, a cross-sectional shape of the tissue support 50 may need to be adjusted to fit within the renal pelvis and/or to ensure that the ureter remains open between the kidney and bladder when an interior negative pressure is applied to the kidney through the ureteral catheter. For example, since the renal pelvis is a cornucopia shaped structure, a cross sectional shape of the tissue support could be selected having a similar cornucopia shape. In addition, the drainage portion of the elongated tube may be curved to correspond to a curvature of the cornucopia shaped renal pelvis.

In some examples, when configured to be deployed in the renal pelvis 120, 122 or kidneys 112, 114, as shown in FIG. 11, the tissue support 50 can have a maximum outer diameter of about 1.5 mm to about 25 mm and a length of about 1.5 mm to about 25 mm. A volume of a three dimensional shape defined by the tissue support 50, when configured for deployment in the renal pelvis or kidney is from about 0.1 $cm^3$ to about 25 $cm^3$.

Figure 12A:
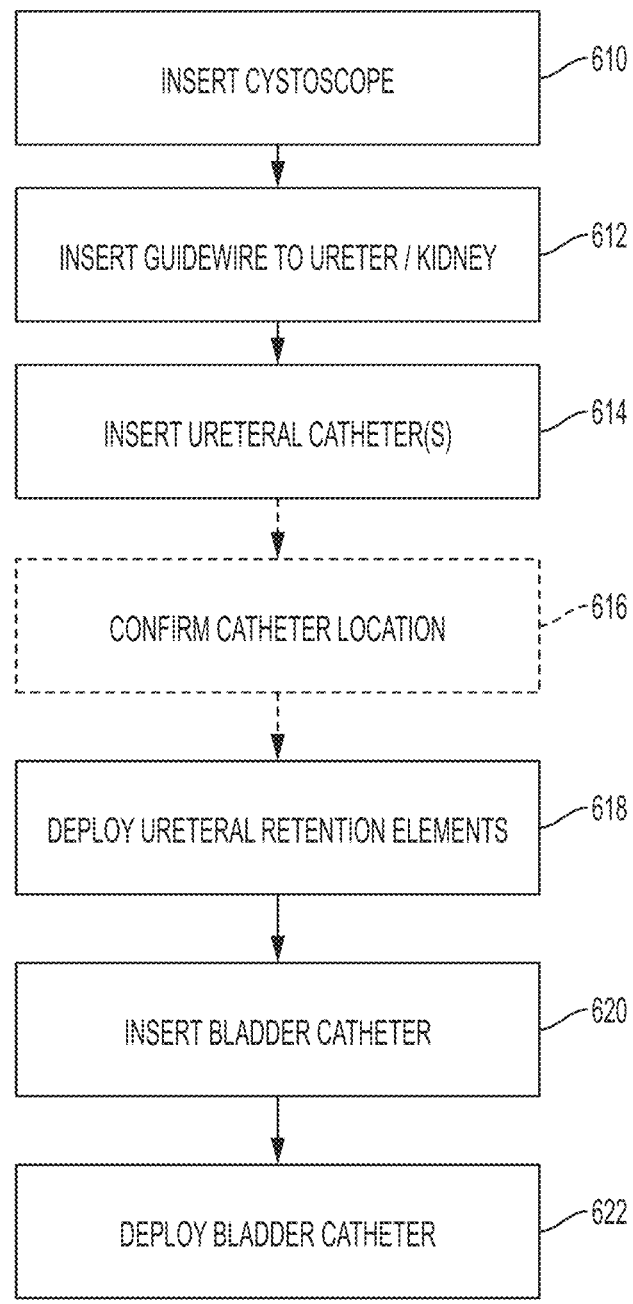
FIG. 12A is a flow chart illustrating a process for insertion and deployment of a ureteral catheter or urine collection assembly according to an example of the present disclosure.

With reference to FIG. 12A, steps for positioning a fluid collection assembly in a patient's body and, optionally, for inducing negative pressure in a patient's ureter and/or kidneys are illustrated. As shown at box 610, a medical professional or caregiver inserts a flexible or rigid cystoscope through the patient's urethra and into the bladder to obtain visualization of the ureteral orifices or openings. Once suitable visualization is obtained, as shown at box 612, a guidewire is advanced through the urethra, bladder, ureteral opening, ureter, and to a desired fluid collection position, such as the renal pelvis of the kidney. Once the guidewire is advanced to the desired fluid collection position, a ureteral catheter of the present invention (examples of which are discussed in detail above) is inserted over the guidewire to the fluid collection position, as shown at box 614. In some examples, the location of the ureteral catheter can be confirmed by fluoroscopy, as shown at box 616. Once the position of the distal end of the catheter is confirmed, as shown at box 618, the retention portion of the ureteral catheter can be deployed. For example, the guidewire can be removed from the catheter, thereby allowing the distal end and/or retention portion to transition to a deployed position. In some examples, the deployed distal end portion of the catheter does not entirely occlude the ureter and/or renal pelvis, such that urine is permitted to pass outside the catheter and through the ureters into the bladder. Since moving the catheter can exert forces against urinary tract tissues, avoiding complete blockage of the ureters avoids application of force to the ureter sidewalls, which may cause injury.

After the ureteral catheter is in place and deployed, the same guidewire can be used to position a second ureteral catheter in the other ureter and/or kidney using the same insertion and positioning methods described herein. For example, the cystoscope can be used to obtain visualization of the other ureteral opening in the bladder, and the guidewire can be advanced through the visualized ureteral opening to a fluid collection position in the other ureter. A catheter can be drawn alongside the guidewire and deployed in the manner described herein. Alternatively, the cystoscope and guidewire can be removed from the body. The cystoscope can be reinserted into the bladder over the first ureteral catheter. The cystoscope is used, in the manner described above, to obtain visualization of the ureteral opening and to assist in advancing a second guidewire to the second ureter and/or kidney for positioning of the second ureteral catheter. Once the ureteral catheters are in place, in some examples, the guidewire and cystoscope are removed. In other examples, the cystoscope and/or guidewire can remain in the bladder to assist with placement of the bladder catheter.

A bladder catheter can also be used either as the only source of negative pressure (as in the examples described in connection with FIGS. 1-10) or to provide an additional drainage conduit for the fluid collection system of FIG. 11. In some examples, the bladder catheter is inserted without use of a cystoscope or other imaging apparatus. Instead, the bladder catheter is merely inserted in its collapsed state through the urethra and into the bladder. The bladder catheter is deployed by retracting the deployment catheter as described above. In other examples, the bladder catheter is inserted over the same guidewire used to position the ureteral catheters.

When used in combination with urine collection catheters deployed in the ureters (as shown in FIG. 11), the bladder catheter can be either a conventional Foley bladder catheter or a bladder catheter of the present invention as discussed in detail above. In any case, once inserted in the bladder, as shown at box 622, an anchor of a Foley catheter or the tissue support is expanded to a deployed position. For example, when an expandable or inflatable catheter is used, fluid may be directed through an inflation lumen of the bladder catheter to expand a balloon structure located in the patient's bladder. In some examples, the urine is permitted to drain by gravity from the urethra. In other examples, a negative pressure is induced in the ureteral catheter and/or bladder catheter to facilitate drainage of the urine.

Figure 12B:
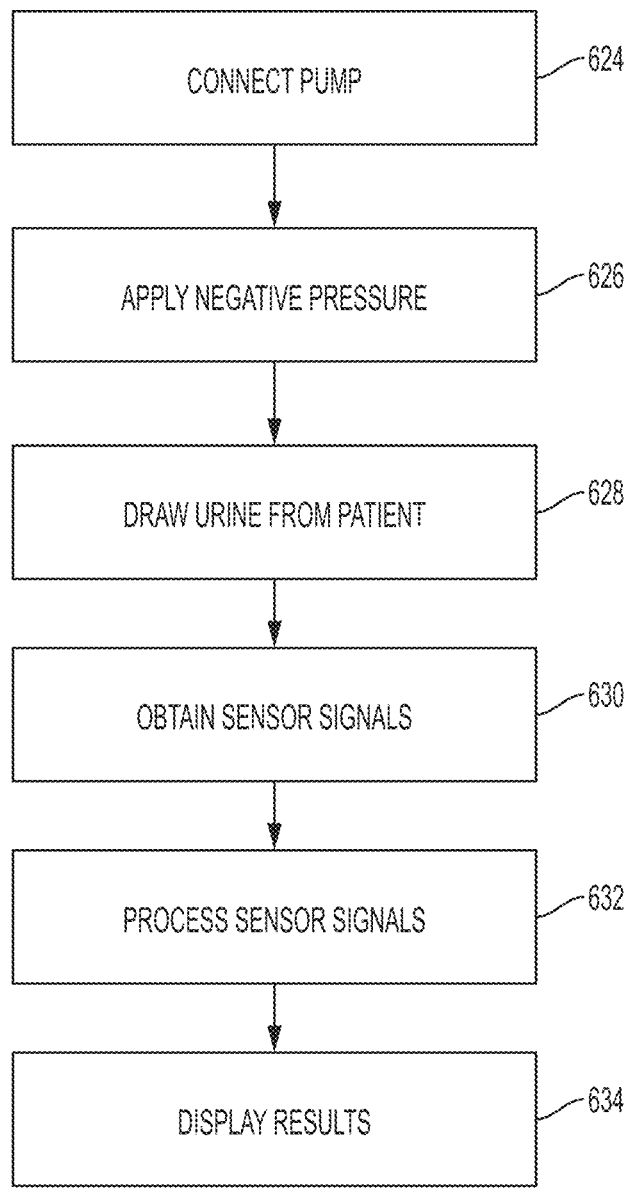
FIG. 12B is a flow chart illustrating a process for applying negative pressure using a ureteral catheter or urine collection assembly according to an example of the present disclosure.

With reference to FIG. 12B, steps for using the urine collection assembly for inducement of negative pressure in the ureter(s) and/or kidney(s) are illustrated. As shown at box 624, after the indwelling portions of the bladder and/or ureteral catheters are correctly positioned and anchoring/retention structures are deployed, the external proximal ends of the catheter(s) are connected to fluid collection or pump assemblies. For example, the ureteral catheter(s) can be connected to a pump for inducing negative pressure at the patient's renal pelvis and/or kidney. In a similar manner, the bladder catheter can be connected directly to a urine collection container for gravity drainage of urine from the bladder or connected to a pump for inducing negative pressure at the bladder.

Once the catheter(s) and pump assembly are connected, negative pressure is applied to the renal pelvis and/or kidney and/or bladder through the drainage lumens of the ureteral catheters and/or bladder catheter, as shown at box 626. The negative pressure is intended to counter congestion mediated interstitial hydrostatic pressures due to elevated intra-abdominal pressure and consequential or elevated renal venous pressure or renal lymphatic pressure. The applied negative pressure is therefore capable of increasing flow of filtrate through the medullary tubules and of decreasing water and sodium re-absorption.

In some examples, mechanical stimulation can be provided to portions of the ureters and/or renal pelvis to supplement or modify therapeutic affects obtained by application of negative pressure. For example, mechanical stimulation devices, such as linear actuators and other known devices for providing, for example, vibration waves, disposed in distal portions of the ureteral catheter(s) can be actuated. While not intending to be bound by theory, it is believed that such stimulation effects adjacent tissues by, for example, stimulating nerves and/or actuating peristaltic muscles associated with the ureter(s) and/or renal pelvis. Stimulation of nerves and activation of muscles may produce changes in pressure gradients or pressure levels in surrounding tissues and organs which may contribute to or, in some cases, enhance therapeutic benefits of negative pressure therapy. In some examples, the mechanical stimulation can comprise pulsating stimulation. In other examples, low levels of mechanical stimulation can be provided continuously as negative pressure is being provided through the ureteral catheter(s). In other examples, inflatable portions of the ureteral catheter could be inflated and deflated in a pulsating manner to stimulate adjacent nerve and muscle tissue, in a similar manner to actuation of the mechanical stimulation devices described herein.

As a result of the applied negative pressure, as shown at box 628, urine is drawn into the catheter at the plurality of drainage ports or openings at the distal end thereof, through the drainage lumen of the catheter, and to a fluid collection container for disposal. As the urine is being drawn to the collection container, at box 630, sensors disposed in the fluid collection system provide a number of measurements about the urine that can be used to assess the volume of urine collected, as well as information about the physical condition of the patient and composition of the urine produced. In some examples, the information obtained by the sensors is processed, as shown at box 632, by a processor associated with the pump and/or with another patient monitoring device and, at box 634, is displayed to the user via a visual display of an associated feedback device.

Exemplary Fluid Collection System

Having described an exemplary urine collection devices, systems, and method of positioning such an assembly in the patient's body, with reference to FIG. 13, a system 700 for inducing negative pressure to a patient's ureter(s) and/or kidney(s) will now be described. The system 700 can comprise the ureteral catheter(s), bladder catheter or the urine collection assembly 100 described hereinabove. As shown in FIG. 13, urine collection catheter 10 comprising the tissue support 50 is connected to one or more fluid collection containers 712 for collecting urine drawn from the renal pelvis and/or bladder. The fluid collection container 712 connected to the urine collection catheter 10 can be in fluid communication with an external fluid pump 710 for generating negative pressure in the ureter(s) and kidney(s) through the catheter 10. The pump 710 can be the pump 200 shown in FIGS. 3 and 8. In other examples, the pump 710 can be a vacuum pump, rotary pump, or other negative pressure source, as is known in the art. As discussed herein, such negative pressure can be provided for overcoming interstitial pressure and forming urine in the kidney or nephron. In some examples, a connection between the fluid collection container 712 and pump 710 can comprise a fluid lock or fluid barrier to prevent air from entering the renal pelvis or kidney in case of incidental therapeutic or non-therapeutic pressure changes. For example, inflow and outflow ports of the fluid container can be positioned below a fluid level in the container. Accordingly, air is prevented from entering medical tubing or the catheter through either the inflow or outflow ports of the fluid container 712. As discussed previously, external portions of the tubing extending between the fluid collection container 712 and the pump 710 can include one or more filters to prevent urine and/or particulates from entering the pump 710.

As shown in FIG. 13, the system 700 further comprises a controller 714, such as a microprocessor, electronically coupled to the pump 710 and having or associated with computer readable memory 716. In some examples, the memory 716 comprises instructions that, when executed, cause the controller 714 to receive information from sensors 174 located on or associated with portions of the catheter 10. Information about a condition of the patient can be determined based on information from the sensors 174. Information from the sensors 174 can also be used to determine and implement operating parameters for the pump 710.

In some examples, the controller 714 is incorporated in a separate and remote electronic device in communication with the pump 710, such as a dedicated electronic device, computer, tablet PC, or smart phone. Alternatively, the controller 714 can be included in the pump 710 and, for example, can control both a user interface for manually operating the pump 710, as well as system functions such as receiving and processing information from the sensors 174.

The controller 714 is configured to receive information from the one or more sensors 174 and to store the information in the associated computer-readable memory 716. For example, the controller 714 can be configured to receive information from the sensor 174 at a predetermined rate, such as once every second, and to determine a conductance based on the received information. In some examples, the algorithm for calculating conductance can also include other sensor measurements, such as urine temperature, to obtain a more robust determination of conductance.

The controller 714 can also be configured to calculate patient physical statistics or diagnostic indicators that illustrate changes in the patient's condition over time. For example, the system 700 can be configured to identify an amount of total sodium excreted. The total sodium excreted may be based, for example, on a combination of flow rate and conductance over a period of time.

With continued reference to FIG. 13, the system 700 can further comprise a feedback device 720, such as a visual display or audio system, for providing information to the user. In some examples, the feedback device 720 can be integrally formed with the pump 710. Alternatively, the feedback device 720 can be a separate dedicated or a multipurpose electronic device, such as a computer, laptop computer, tablet PC, smart phone, or other handheld electronic devices. The feedback device 720 is configured to receive the calculated or determined measurements from the controller 714 and to present the received information to a user via the feedback device 720. For example, the feedback device 720 may be configured to display current negative pressure (in mmHg) being applied to the urinary tract. In other examples, the feedback device 720 is configured to display current flow rate of urine, temperature, current conductance in mS/m of urine, total urine produced during the session, total sodium excreted during the session, other physical parameters, or any combination thereof.

In some examples, the feedback device 720 further comprises a user interface module or component that allows the user to control operation of the pump 710. For example, the user can engage or turn off the pump 710 via the user interface. The user can also adjust pressure applied by the pump 710 to achieve a greater magnitude or rate of sodium excretion and fluid removal.

Optionally, the feedback device 720 and/or pump 710 further comprise a data transmitter 722 for sending information from the device 720 and/or pump 710 to other electronic devices or computer networks. The data transmitter 722 can utilize a short-range or long-range data communications protocol. An example of a short-range data transmission protocol is Bluetooth®. Long-range data transmission networks include, for example, Wi-Fi or cellular networks. The data transmitter 722 can send information to a patient's physician or caregiver to inform the physician or caregiver about the patient's current condition. Alternatively, or in addition, information can be sent from the data transmitter 722 to existing databases or information storage locations, such as, for example, to include the recorded information in a patient's electronic health record (EHR).

With continued reference to FIG. 13, in addition to the urine sensors 174, in some examples, the system 700 further comprises one or more patient monitoring sensors 724. Patient monitoring sensors 724 can include invasive and non-invasive sensors for measuring information about the patient's urine composition, as discussed in detail above, blood composition (e.g., hematocrit ratio, analyte concentration, protein concentration, creatinine concentration) and/or blood flow (e.g., blood pressure, blood flow velocity). Hematocrit is a ratio of the volume of red blood cells to the total volume of blood. Normal hematocrit is about 25% to 40%, and preferably about 35% and 40% (e.g., 35% to 40% red blood cells by volume and 60% to 65% plasma).

Non-invasive patient monitoring sensors 724 can include pulse oximetry sensors, blood pressure sensors, heart rate sensors, and respiration sensors (e.g., a capnography sensor). Invasive patient monitoring sensors 724 can include invasive blood pressure sensors, glucose sensors, blood velocity sensors, hemoglobin sensors, hematocrit sensors, protein sensors, creatinine sensors, and others. In still other examples, sensors may be associated with an extracorporeal blood system or circuit and configured to measure parameters of blood passing through tubing of the extracorporeal system. For example, analyte sensors, such as capacitance sensors or optical spectroscopy sensors, may be associated with tubing of the extracorporeal blood system to measure parameter values of the patient's blood as it passes through the tubing. The patient monitoring sensors 724 can be in wired or wireless communication with the pump 710 and/or controller 714.

In some examples, the controller 714 is configured to cause the pump 710 to provide treatment for a patient based information obtained from the urine analyte sensor 174 and/or patient monitoring sensors 724, such as blood monitoring sensors. For example, pump 710 operating parameters can be adjusted based on changes in the patient's blood hematocrit ratio, blood protein concertation, creatinine concentration, urine output volume, urine protein concentration (e.g., albumin), and other parameters. For example, the controller 714 can be configured to receive information about a blood hematocrit ratio or creatinine concentration of the patient from the patient monitoring sensors 724 and/or analyte sensors 174. The controller 714 can be configured to adjust operating parameters of the pump 710 based on the blood and/or urine measurements. In other examples, hematocrit ratio may be measured from blood samples periodically obtained from the patient. Results of the tests can be manually or automatically provided to the controller 714 for processing and analysis.

As discussed herein, measured hematocrit values for the patient can be compared to predetermined threshold or clinically acceptable values for the general population. Generally, hematocrit levels for females are lower than for males. In other examples, measured hematocrit values can be compared to patient baseline values obtained prior to a surgical procedure. When the measured hematocrit value is increased to within the acceptable range, the pump 710 may be turned off ceasing application of negative pressure to the ureter or kidneys. In a similar manner, the intensity of negative pressure can be adjusted based on measured parameter values. For example, as the patient's measured parameters begin to approach the acceptable range, intensity of negative pressure being applied to the ureter and kidneys can be reduced. In contrast, if an undesirable trend (e.g., a decrease in hematocrit value, urine output rate, and/or creatinine clearance) is identified, the intensity of negative pressure can be increased in order to produce a positive physiological result. For example, the pump 710 may be configured to begin by providing a low level of negative pressure (e.g., between about 0.1 mmHg and 10 mmHg). The negative pressure may be incrementally increased until a positive trend in patient creatinine level is observed. However, generally, negative pressure provided by the pump 710 will not exceed about 50 mmHg.

Figure 14A:
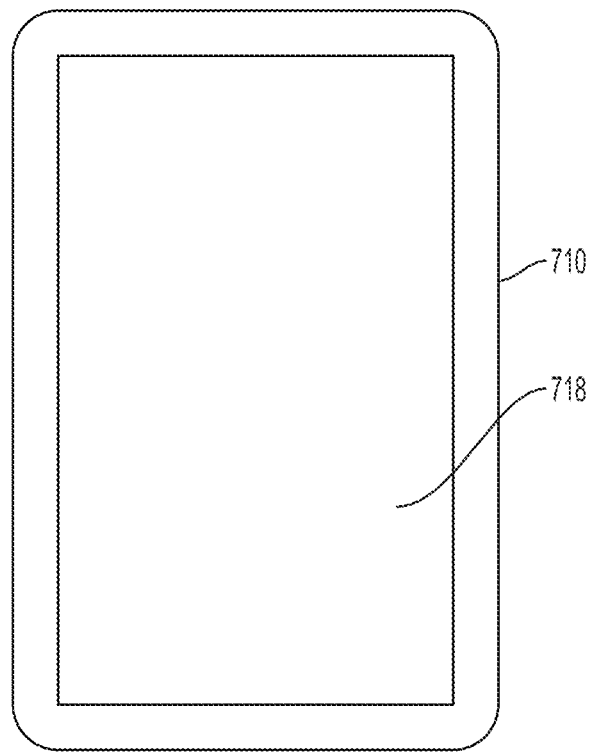
FIG. 14A is a plan view of a pump for use with the system of FIG. 13 according to an example of the present disclosure.
Figure 14B:
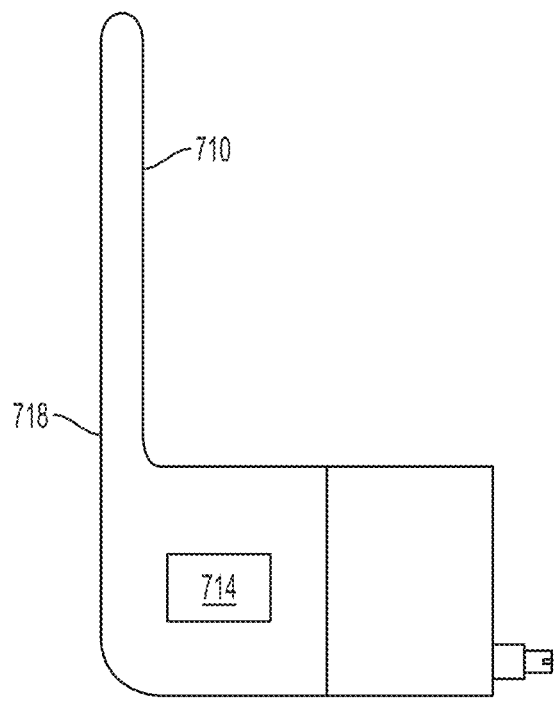
FIG. 14B is a side elevation view of the pump of FIG. 14A.

With reference to FIGS. 14A and 14B, an exemplary pump 710 for use with the system is illustrated. In some examples, the pump 710 is a micro-pump configured to draw fluid from the catheter(s) 1000 and having a sensitivity or accuracy of about 10 mmHg or less. Desirably, the pump 710 is capable of providing a range of flow of urine between 0.05 ml/min and 3 ml/min for extended periods of time, for example, for about 8 hours to about 24 hours per day, for one (1) to about 30 days or longer. At 0.2 ml/min, it is anticipated that about 300 mL of urine per day is collected by the system 700. The pump 710 can be configured to provide a negative pressure to the bladder of the patient, the negative pressure ranging between about 0.1 mmHg and 50 mmHg or about 5 mmHg to about 20 mmHg (gauge pressure at the pump 710). For example, a micro-pump manufactured by Langer Inc. (Model BT100-2J) can be used with the presently disclosed system 700. Diaphragm aspirator pumps, as well as other types of commercially available pumps, can also be used for this purpose. Peristaltic pumps can also be used with the system 700. In other examples, a piston pump, vacuum bottle, or manual vacuum source can be used for providing negative pressure. In other examples, the system can be connected to a wall suction source, as is available in a hospital, through a vacuum regulator for reducing negative pressure to therapeutically appropriate levels.

In some examples, at least a portion of the pump assembly can be positioned within the patient's urinary tract, for example within the bladder. For example, the pump assembly can comprise a pump module and a control module coupled to the pump module, the control module being configured to direct motion of the pump module. At least one (one or more) of the pump module, the control module, or the power supply may be positioned within the patient's urinary tract. The pump module can comprise at least one pump element positioned within the fluid flow channel to draw fluid through the channel. Some examples of suitable pump assemblies, systems and methods of use are disclosed in U.S. Patent Application No. 62/550,259, entitled "Indwelling Pump for Facilitating Removal of Urine from the Urinary Tract", filed concurrently herewith, which is incorporated by reference herein in its entirety.

In some examples, the pump 710 is configured for extended use and, thus, is capable of maintaining precise suction for extended periods of time, for example, for about 8 hours to about 24 hours per day, for 1 to about 30 days or longer. Further, in some examples, the pump 710 is configured to be manually operated and, in that case, includes a control panel 718 that allows a user to set a desired suction value. The pump 710 can also include a controller or processor, which can be the same controller that operates the system 700 or can be a separate processor dedicated for operation of the pump 710. In either case, the processor is configured for both receiving instructions for manual operation of the pump and for automatically operating the pump 710 according to predetermined operating parameters. Alternatively, or in addition, operation of the pump 710 can be controlled by the processor based on feedback received from the plurality of sensors associated with the catheter.

In some examples, the processor is configured to cause the pump 710 to operate intermittently. For example, the pump 710 may be configured to emit pulses of negative pressure followed by periods in which no negative pressure is provided. In other examples, the pump 710 can be configured to alternate between providing negative pressure and positive pressure to produce an alternating flush and pump effect. For example, a positive pressure of about 0.1 mmHg to 20 mmHg, and preferably about 5 mmHg to 20 mmHg can be provided followed by a negative pressure ranging from about 0.1 mmHg to 50 mmHg.

Treatment for Removing Excess Fluid from a Patient with Hemodilution

According to another aspect of the disclosure, a method for removing excess fluid from a patient with hemodilution is provided. In some examples, hemodilution can refer to an increase in a volume of plasma in relation to red blood cells and/or a reduced concentration of red blood cells in circulation, as may occur when a patient is provided with an excessive amount of fluid. The method can involve measuring and/or monitoring patient hematocrit levels to determine when hemodilution has been adequately addressed. Low hematocrit levels are a common post-surgical or post-trauma condition that can lead to undesirable therapeutic outcomes. As such, management of hemodilution and confirming that hematocrit levels return to normal ranges is a desirable therapeutic result for surgical and post-surgical patient care.

Figure 15:
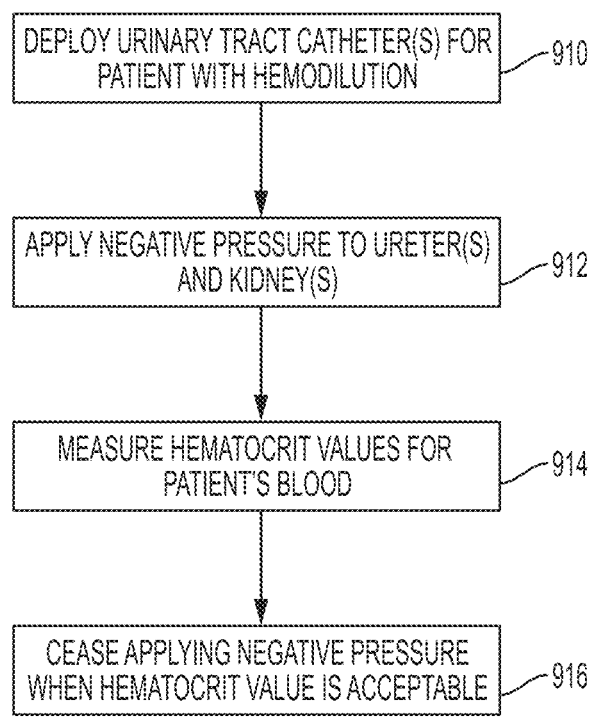
FIG. 15 is a flow chart illustrating a process for reducing creatinine and/or protein levels of a patient according to an example of the disclosure.

Steps for removing excess fluid from a patient using the devices and systems described herein are illustrated in FIG. 15. As shown in FIG. 15, the treatment method comprises deploying a urinary tract catheter, such as the urine collection catheter configured to be deployed in the bladder or renal pelvis of the present invention, in the ureter and/or kidney of a patient such that flow of urine from the ureter and/or kidney, as shown at box 910. The catheter may be placed to avoid occluding the ureter and/or kidney. In some examples, a fluid collecting portion of the catheter may be positioned in the renal pelvis of the patient's kidney. In some examples, a ureter catheter may be positioned in each of the patient's kidneys. In other examples, a urine collection catheter may be deployed in the bladder or ureter. In some examples, the ureteral catheter comprises one or more of any of the retention portions described herein. For example, the ureteral catheter can comprise a tube defining a drainage lumen comprising a helical retention portion and a plurality of drainage ports. In other examples, the catheter can include an inflatable retention portion (e.g., a balloon catheter), funnel-shaped fluid collection and retention portion, or a pigtail coil.

As shown at box 912, the method further comprises applying negative pressure to the ureter and/or kidney through the catheter to induce production of urine in the kidney(s) and to extract urine from the patient. Desirably, negative pressure is applied for a period of time sufficient to reduce the patient's blood creatinine levels by a clinically significant amount.

Negative pressure may continue to be applied for a predetermined period of time. For example, a user may be instructed to operate the pump for the duration of a surgical procedure or for a time period selected based on physiological characteristics of the patient. In other examples, patient condition may be monitored to determine when sufficient treatment has been provided. For example, as shown at box 914, the method may further comprise monitoring the patient to determine when to cease applying negative pressure to the patient's ureter and/or kidneys. In a preferred and non-limiting example, a patient's hematocrit level is measured. For example, patient monitoring devices may be used to periodically obtain hematocrit values. In other examples, blood samples may be drawn periodically to directly measure hematocrit. In some examples, concentration and/or volume of urine expelled from the body through the catheter may also be monitored to determine a rate at which urine is being produced by the kidneys. In a similar manner, expelled urine output may be monitored to determine protein concentration and/or creatinine clearance rate for the patient. Reduced creatinine and protein concentration in urine may be indicative of over-dilution and/or depressed renal function. Measured values can be compared to the predetermined threshold values to assess whether negative pressure therapy is improving patient condition, and should be modified or discontinued. For example, as discussed herein, a desirable range for patient hematocrit may be between 25% and 40%. In other preferred and non-limiting examples, as described herein, patient body weight may be measured and compared to a dry body weight. Changes in measured patient body weight demonstrate that fluid is being removed from the body. As such, a return to dry body weight represents that hemodilution has been appropriately managed and the patient is not over-diluted.

As shown at box 916, a user may cause the pump to cease providing negative pressure therapy when a positive result is identified. In a similar manner, patient blood parameters may be monitored to assess effectiveness of the negative pressure being applied to the patient's kidneys. For example, a capacitance or analyte sensor may be placed in fluid communication with tubing of an extracorporeal blood management system. The sensor may be used to measure information representative of blood protein, oxygen, creatinine, and/or hematocrit levels. Measured blood parameter values may be measured continuously or periodically and compared to various threshold or clinically acceptable values. Negative pressure may continue to be applied to the patient's kidney or ureter until a measured parameter value falls within a clinically acceptable range. Once a measured values fails within the threshold or clinically acceptable range, as shown at box 916, application of negative pressure may cease.

Treatment of Patients Undergoing a Fluid Resuscitation Procedure

According to another aspect of the disclosure, a method for removing excess fluid for a patient undergoing a fluid resuscitation procedure, such as coronary graft bypass surgery, by removing excess fluid from the patient is provided. During fluid resuscitation, solutions such as saline solutions and/or starch solutions, are introduced to the patient's bloodstream by a suitable fluid delivery process, such as an intravenous drip. For example, in some surgical procedures, a patient may be supplied with between 5 and 10 times a normal daily intake of fluid. Fluid replacement or fluid resuscitation can be provided to replace bodily fluids lost through sweating, bleeding, dehydration, and similar processes. In the case of a surgical procedure such as coronary graft bypass, fluid resuscitation is provided to help maintain a patient's fluid balance and blood pressure within an appropriate rate. Acute kidney injury (AKI) is a known complication of coronary artery graft bypass surgery. AKI is associated with a prolonged hospital stay and increased morbidity and mortality, even for patients who do not progress to renal failure. See Kim, et al., *Relationship between a perioperative intravenous fluid administration strategy and acute kidney injury following off-pump coronary artery bypass surgery: an observational study, Critical Care* 19:350 (1995). Introducing fluid to blood also reduces hematocrit levels which has been shown to further increase mortality and morbidity. Research has also demonstrated that introducing saline solution to a patient may depress renal functional and/or inhibit natural fluid management processes. As such, appropriate monitoring and control of renal function may produce improved outcomes and, in particular, may reduce post-operative instances of AKI.

Figure 16:
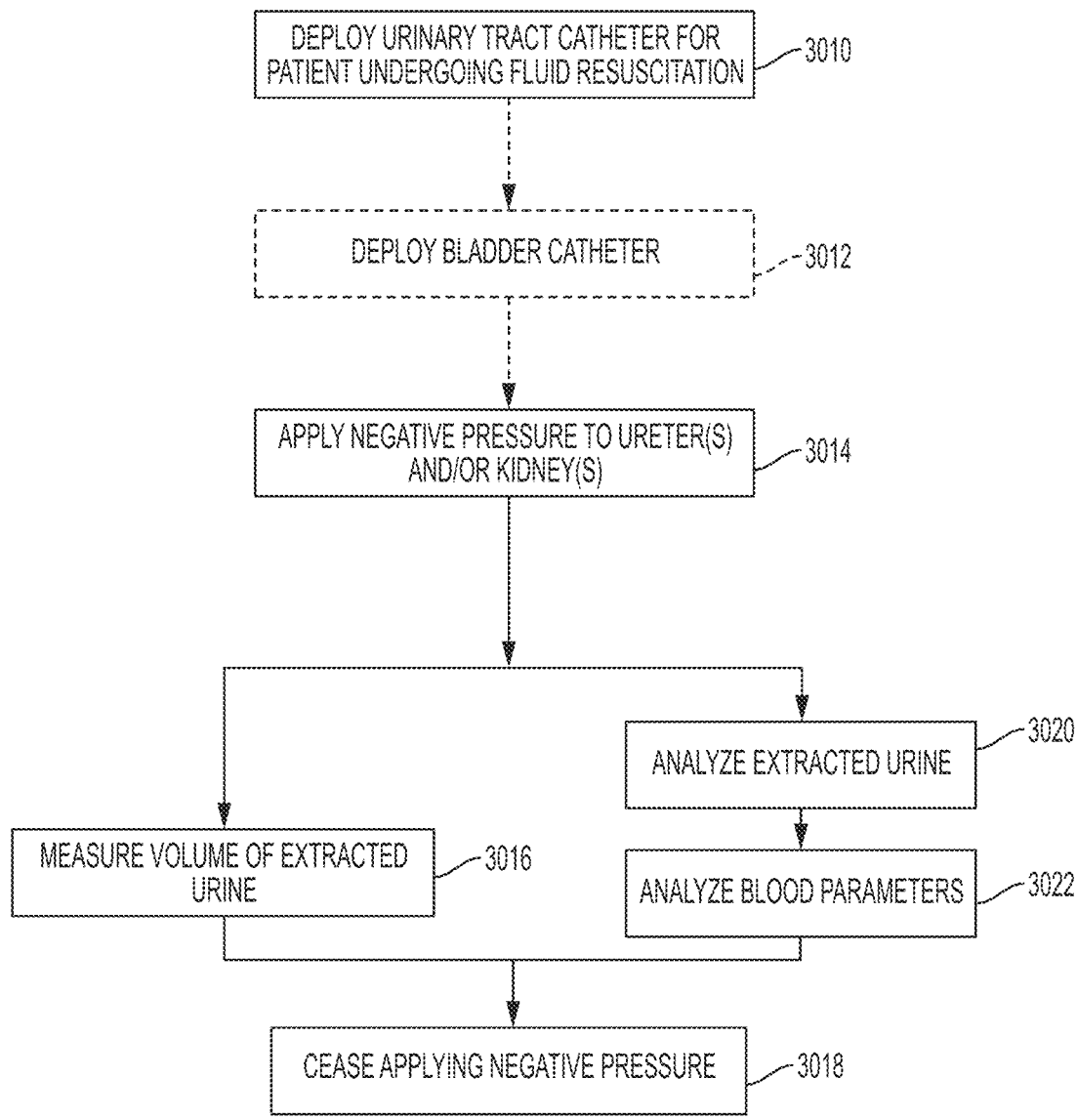
FIG. 16 is a flow chart illustrating a process for treating a patient undergoing fluid resuscitation according to an example of the disclosure.

A method of treating a patient undergoing fluid resuscitation is illustrated in FIG. 16. As shown at box 3010, the method comprises deploying a ureteral catheter in the ureter and/or kidney of a patient such that flow of urine from the ureter and/or kidney is not prevented by occlusion of the ureter and/or kidney. For example, a fluid collecting portion of the catheter may be positioned in the renal pelvis. In other examples, the catheter may be deployed in the bladder or ureter. The catheter can comprise one or more of the urine collection catheters configured to be deployed in the bladder or renal pelvis as described herein. For example, the catheter can comprise a tube defining a drainage lumen and comprising a helical retention portion and a plurality of drainage ports. In other examples, the catheter can include an inflatable retention portion (e.g., a balloon catheter) or a pigtail coil.

As shown at box 3012, optionally, a bladder catheter may also be deployed in the patient's bladder. For example, the bladder catheter may be positioned to seal the urethra opening to prevent passage of urine from the body through the urethra. The bladder catheter can include an inflatable anchor (e.g., a Foley catheter) for maintaining the distal end of the catheter in the bladder. As described herein, other arrangements of coils and helices may also be used to obtain proper positioning of the bladder catheter. The bladder catheter can be configured to collect urine which entered the patient's bladder prior to placement of the ureteral catheter(s). The bladder catheter may also collect urine which flows past the fluid collection portion(s) of the ureteral catheter and enters the bladder. In some examples, a proximal portion of the ureteral catheter may be positioned in a drainage lumen of the bladder catheter. In a similar manner, the bladder catheter may be advanced into the bladder using the same guidewire used for positioning of the ureteral catheter(s). In some examples, negative pressure may be provided to the bladder through the drainage lumen of the bladder catheter. In other examples, negative pressure may only be applied to the ureteral catheter(s). In that case, the bladder catheter drains by gravity.

As shown at box 3014, following deployment of the ureteral catheter(s), negative pressure is applied to the ureter and/or kidney through the ureteral catheter(s). For example, negative pressure can be applied for a period of time sufficient to extract urine comprising a portion of the fluid provided to the patient during the fluid resuscitation procedure. As described herein, negative pressure can be provided by an external pump connected to a proximal end or port of the catheter. The pump can be operated continually or periodically dependent on therapeutic requirements of the patient. In some cases, the pump may alternate between applying negative pressure and positive pressure.

Negative pressure may continue to be applied for a predetermined period of time. For example, a user may be instructed to operate the pump for the duration of a surgical procedure or for a time period selected based on physiological characteristics of the patient. In other examples, patient condition may be monitored to determine when a sufficient amount of fluid has been drawn from the patient. For example, as shown at box 3016, fluid expelled from the body may be collected and a total volume of obtained fluid may be monitored. In that case, the pump can continue to operate until a predetermined fluid volume has been collected from the ureteral and/or bladder catheters. The predetermined fluid volume may be based, for example, on a volume of fluid provided to the patient prior to and during the surgical procedure. As shown at box 3018, application of negative pressure to the ureter and/or kidneys is stopped when the collected total volume of fluid exceeds the predetermined fluid volume.

In other examples, operation of the pump can be determined based on measured physiological parameters of the patient, such as measured creatinine clearance, blood creatinine level, or hematocrit ratio. For example, as shown at box 3020, urine collected form the patient may be analyzed by one or more sensors associated with the catheter and/or pump. The sensor can be a capacitance sensor, analyte sensor, optical sensor, or similar device configured to measure urine analyte concentration. In a similar manner, as shown at box 3022, a patient's blood creatinine or hematocrit level could be analyzed based on information obtain from the patient monitoring sensors discussed hereinabove. For example, a capacitance sensor may be placed in an existing extracorporeal blood system. Information obtained by the capacitance sensor may be analyzed to determine a patient's hematocrit ratio. The measured hematocrit ratio may be compared to certain expected or therapeutically acceptable values. The pump may continue to apply negative pressure to the patient's ureter and/or kidney until measured values within the therapeutically acceptable range are obtained. Once a therapeutically acceptable value is obtained, application of negative pressure may be stopped as shown at box 3018.

In other examples, patient body weight may be measured to assess whether fluid is being removed from the patient by the applied negative pressure therapy. For example, a patient's measured bodyweight (including fluid introduced during a fluid resuscitation procedure) can be compared to a patient's dry body weight. As used herein, dry weights is defined as normal body weight measured when a patient is not over-diluted. For example, a patient who is not experiencing one or more of: elevated blood pressure, lightheadedness or cramping, swelling of legs, feet, arms, hands, or around the eyes, and who is breathing comfortably, likely does not have excess fluid. A weight measured when the patient is not experiencing such symptoms can be a dry body weight. Patient weight can be measured periodically until the measured weight approaches the dry body weight. When the measured weight approaches (e.g., is within between 5% and 10% of dry body weight), as shown at box 3018, application of negative pressure can be stopped.

EXPERIMENTAL EXAMPLES

Inducement of negative pressure within the renal pelvis of farm swine was performed for the purpose of evaluating effects of negative pressure therapy on renal congestion in the kidney. An objective of these studies was to demonstrate whether a negative pressure delivered into the renal pelvis significantly increases urine output in a swine model of renal congestion. In Example 1, a pediatric Fogarty catheter, normally used in embolectomy or bronchoscopy applications, was used in the swine model solely for proof of principle for inducement of negative pressure in the renal pelvis. It is not suggested that a Fogarty catheter be used in humans in clinical settings to avoid injury of urinary tract tissues.

Example 1

Method

Figure 17:
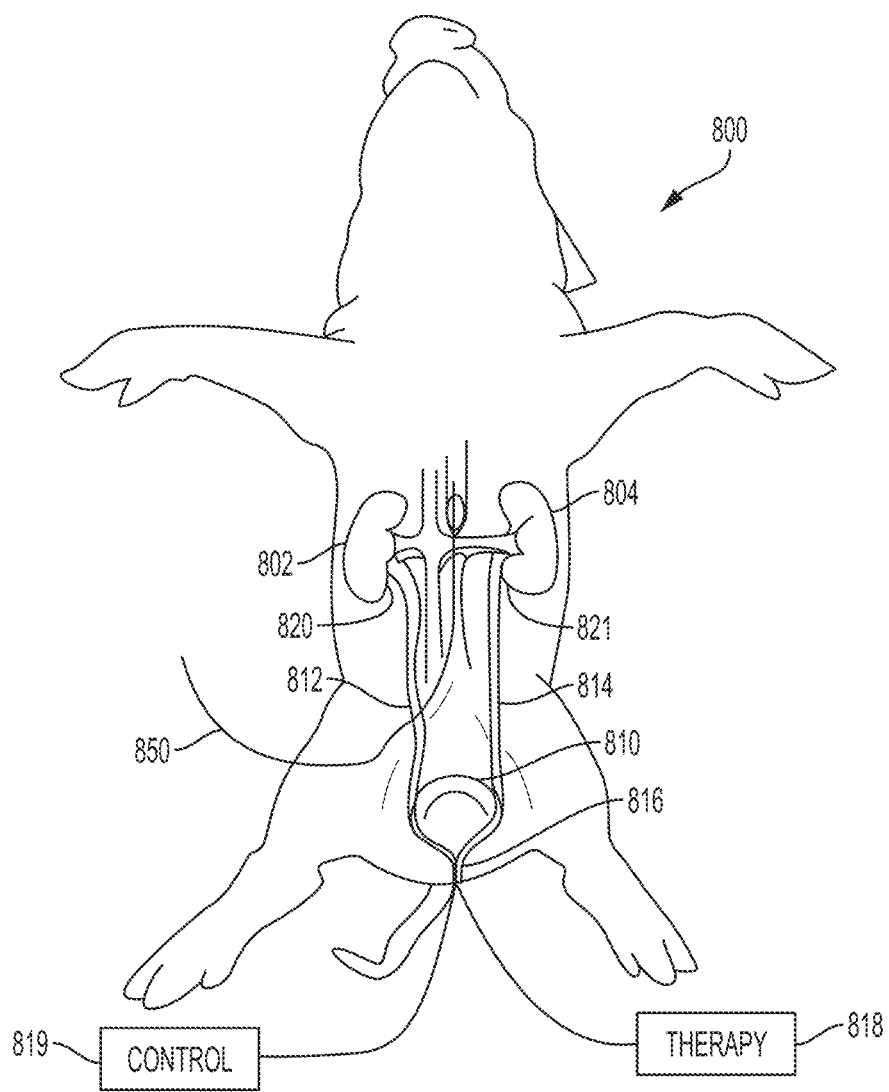
FIG. 17 is a schematic drawing of an experimental set-up for evaluating negative pressure therapy in a swine model.

Four farm swine 800 were used for purposes of evaluating effects of negative pressure therapy on renal congestion in the kidney. As shown in FIG. 17, pediatric Fogarty catheters 812, 814 were inserted to the renal pelvis region 820, 821 of each kidney 802, 804 of the four swine 800. The catheters 812, 814 were deployed within the renal pelvis region by inflating an expandable balloon to a size sufficient to seal the renal pelvis and to maintain the position of the balloon within the renal pelvis. The catheters 812, 814 extend from the renal pelvis 802, 804, through a bladder 810 and urethra 816, and to fluid collection containers external to the swine.

Urine output of two animals was collected for a 15 minute period to establish a baseline for urine output volume and rate. Urine output of the right kidney 802 and the left kidney 804 were measured individually and found to vary considerably. Creatinine clearance values were also determined.

Renal congestion (e.g., congestion or reduced blood flow in the veins of the kidney) was induced in the right kidney 802 and the left kidney 804 of the animal 800 by partially occluding the inferior vena cava (IVC) with an inflatable balloon catheter 850 just above to the renal vein outflow. Pressure sensors were used to measure IVC pressure. Normal IVC pressures were 1-4 mmHg. By inflating the balloon of the catheter 850 to approximately three quarters of the IVC diameter, the IVC pressures were elevated to between 15-25 mmHg. Inflation of the balloon to approximately three quarters of IVC diameter resulted in a 50-85% reduction in urine output. Full occlusion generated IVC pressures above 28 mmHg and was associated with at least a 95% reduction in urine output.

One kidney of each animal 800 was not treated and served as a control ("the control kidney 802"). The ureteral catheter 812 extending from the control kidney was connected to a fluid collection container 819 for determining fluid levels. One kidney ("the treated kidney 804") of each animal was treated with negative pressure from a negative pressure source (e.g., a therapy pump 818 in combination with a regulator designed to more accurately control the low magnitude of negative pressures) connected to the ureteral catheter 814. The pump 818 was an Air Cadet Vacuum Pump from Cole-Parmer Instrument Company (Model No. EW-07530-85). The pump 818 was connected in series to the regulator. The regulator was an V-800 Series Miniature Precision Vacuum Regulator—1/8 NPT Ports (Model No. V-800-10-W/K), manufactured by Airtrol Components Inc.

The pump 818 was actuated to induce negative pressure within the renal pelvis 820, 821 of the treated kidney according to the following protocol. First, the effect of negative pressure was investigated in the normal state (e.g., without inflating the IVC balloon). Four different pressure levels (−2, −10, −15, and −20 mmHg) were applied for 15 minutes each and the rate of urine produced and creatinine clearance were determined. Pressure levels were controlled and determined at the regulator. Following the −20 mmHg therapy, the IVC balloon was inflated to increase the pressure by 15-20 mmHg. The same four negative pressure levels were applied. Urine output rate and creatinine clearance rate for the congested control kidney 802 and treated kidney 804 were obtained. The animals 800 were subject to congestion by partial occlusion of the IVC for 90 minutes. Treatment was provided for 60 minutes of the 90 minute congestion period.

Following collection of urine output and creatinine clearance data, kidneys from one animal were subjected to gross examination then fixed in a 10% neutral buffered formalin. Following gross examination, histological sections were obtained, examined, and magnified images of the sections were captured. The sections were examined using an upright Olympus BX41 light microscope and images were captured using an Olympus DP25 digital camera. Specifically, photomicrograph images of the sampled tissues were obtained at low magnification (20× original magnification) and high magnification (100× original magnification). The obtained images were subjected to histological evaluation. The purpose of the evaluation was to examine the tissue histologically and to qualitatively characterize congestion and tubular degeneration for the obtained samples.

Surface mapping analysis was also performed on obtained slides of the kidney tissue. Specifically, the samples were stained and analyzed to evaluate differences in size of tubules for treated and untreated kidneys. Image processing techniques calculated a number and/or relative percentage of pixels with different coloration in the stained images. Calculated measurement data was used to determine volumes of different anatomical structures.

Results

Urine Output and Creatinine Clearance

Urine output rates were highly variable. Three sources of variation in urine output rate were observed during the study. The inter-individual and hemodynamic variability were anticipated sources of variability known in the art. A third source of variation in urine output, upon information and belief believed to be previously unknown, was identified in the experiments discussed herein, namely, contralateral intra-individual variability in urine output.

Baseline urine output rates were 0.79 ml/min for one kidney and 1.07 ml/min for the other kidney (e.g., a 26% difference). The urine output rate is a mean rate calculated from urine output rates for each animal.

When congestion was provided by inflating the IVC balloon, the treated kidney urine output dropped from 0.79 ml/min to 0.12 ml/min (15.2% of baseline). In comparison, the control kidney urine output rate during congestion dropped from 1.07 ml/min to 0.09 ml/min (8.4% of baseline). Based on urine output rates, a relative increase in treated kidney urine output compared to control kidney urine output was calculated, according to the following equation:

(Therapy Treated/Baseline Treated)/(Therapy Control/Baseline Control)=Relative increase (0.12 ml/min/0.79 ml/min)/(0.09 ml/min/1.07 ml/min)=180.6%

Thus, the relative increase in treated kidney urine output rate was 180.6% compared to control. This result shows a greater magnitude of decrease in urine production caused by congestion on the control side when compared to the treatment side. Presenting results as a relative percentage difference in urine output adjusts for differences in urine output between kidneys.

Figure 18:
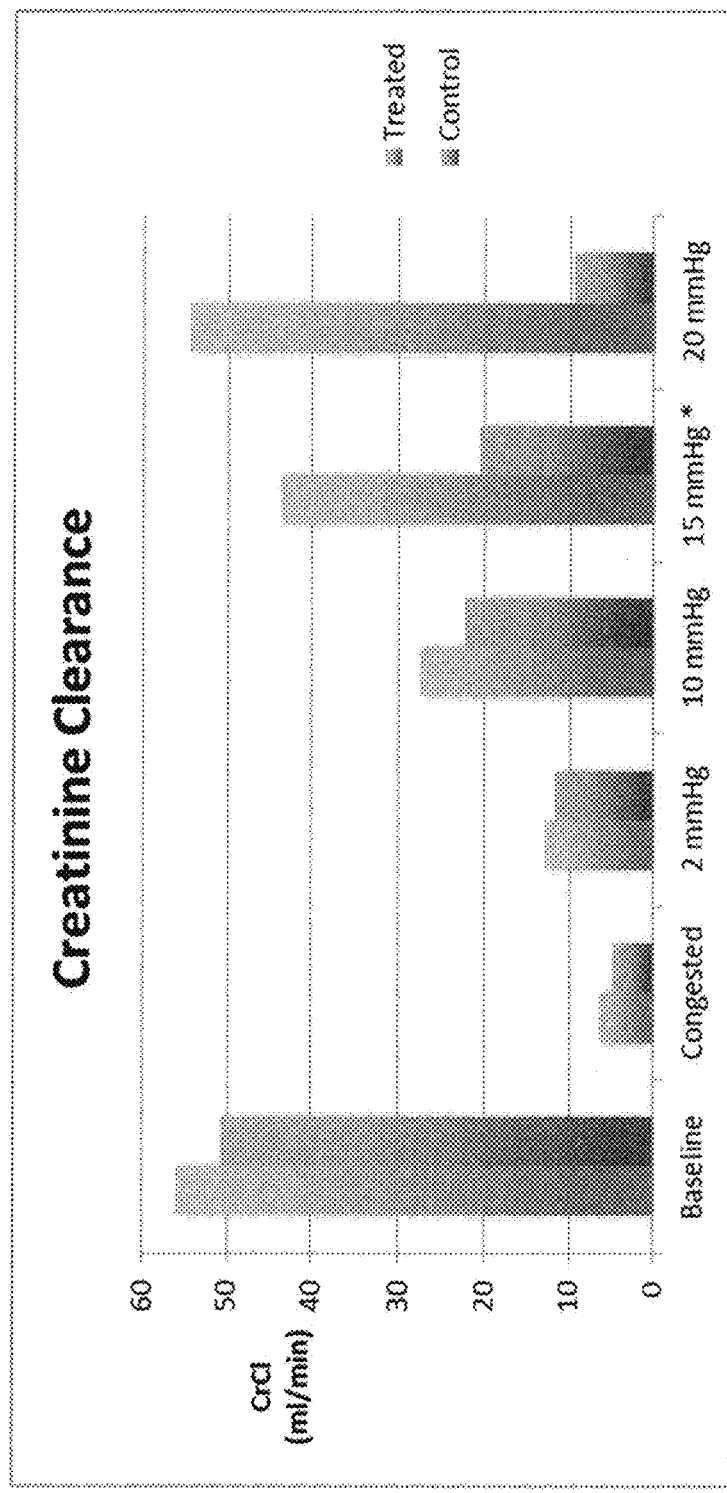
FIG. 18 is a graph of creatinine clearance rates for tests conducted using the experimental set-up shown in FIG. 17.

Creatinine clearance measurements for baseline, congested, and treated portions for one of the animals are shown in FIG. 18.

Gross Examination and Histological Evaluation

Based on gross examination of the control kidney (right kidney) and treated kidney (left kidney), it was determined that the control kidney had a uniformly dark red-brown color, which corresponds with more congestion in the control kidney compared to the treated kidney. Qualitative evaluation of the magnified section images also noted increased congestion in the control kidney compared to the treated kidney. Specifically, as shown in Table 1, the treated kidney exhibited lower levels of congestion and tubular degeneration compared to the control kidney. The following qualitative scale was used for evaluation of the obtained slides.

| Congestion | |
| --- | --- |
| Lesion | Score |
| None: | 0 |
| Mild: | 1 |
| Moderate: | 2 |
| Marked: | 3 |
| Severe: | 4 |

| Tubular degeneration | |
|---|---|
| Lesion | Score |
| None: | 0 |
| Mild: | 1 |
| Moderate: | 2 |
| Marked: | 3 |
| Severe: | 4 |

TABLE 1

TABULATED RESULTS

| | | Histologic lesions | | |
|---|---|---|---|---|
| Animal ID/Organ/Gross lesion | Slide number | Congestion | Tubular hyaline casts | Granulomas |
| 6343/Left Kidney/Normal | R16-513-1 | 1 | 1 | 0 |
| 6343/Left Kidney/Normal with hemorrhagic streak | R16-513-2 | 1 | 1 | 0 |
| 6343/Right Kidney/Congestion | R16-513-3 | 2 | 2 | 1 |
| 6343/Right Kidney/Congestion | R16-513-4 | 2 | 1 | 1 |

As shown in Table 1, the treated kidney (left kidney) exhibited only mild congestion and tubular degeneration. In contrast, the control kidney (right kidney) exhibited moderate congestion and tubular degeneration. These results were obtained by analysis of the slides discussed below.

Figure 19A:
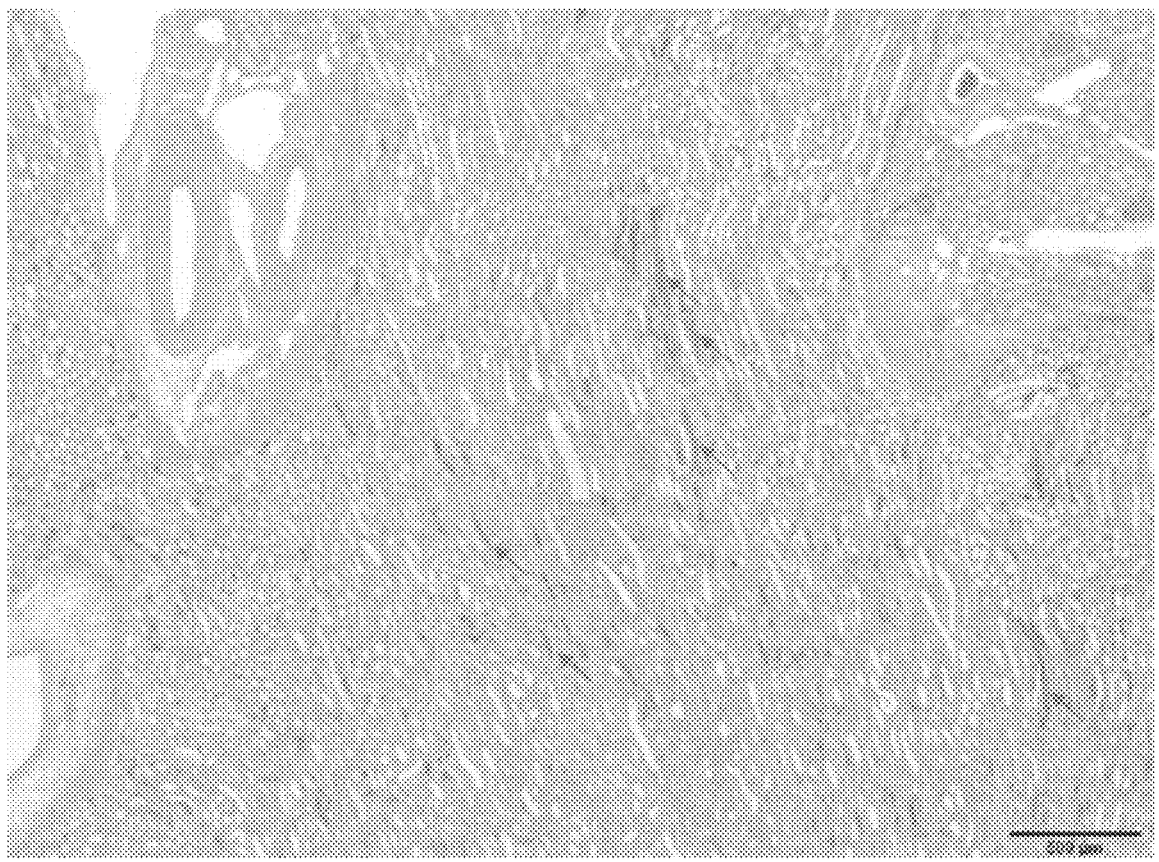
FIG. 19A is a low magnification photomicrograph of kidney tissue from a congested kidney treated with negative pressure therapy.
Figure 19B:
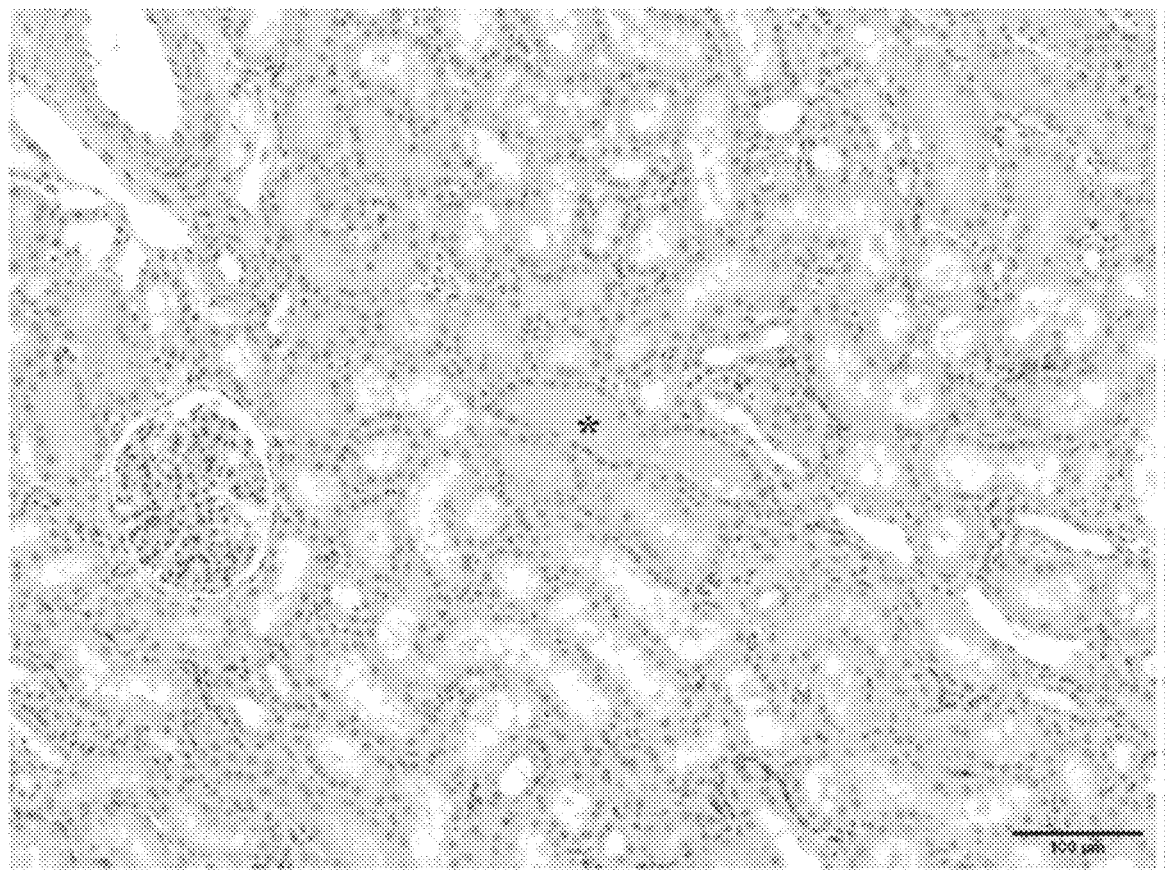
FIG. 19B is a high magnification photomicrograph of the kidney tissue shown in FIG. 19A.

FIGS. 19A and 19B are low and high magnification photomicrographs of the left kidney (treated with negative pressure) of the animal. Based on the histological review, mild congestion in the blood vessels at the corticomedullary junction was identified, as indicated by the arrows. As shown in FIG. 19B, a single tubule with a hyaline cast (as identified by the asterisk) was identified.

Figure 19C:
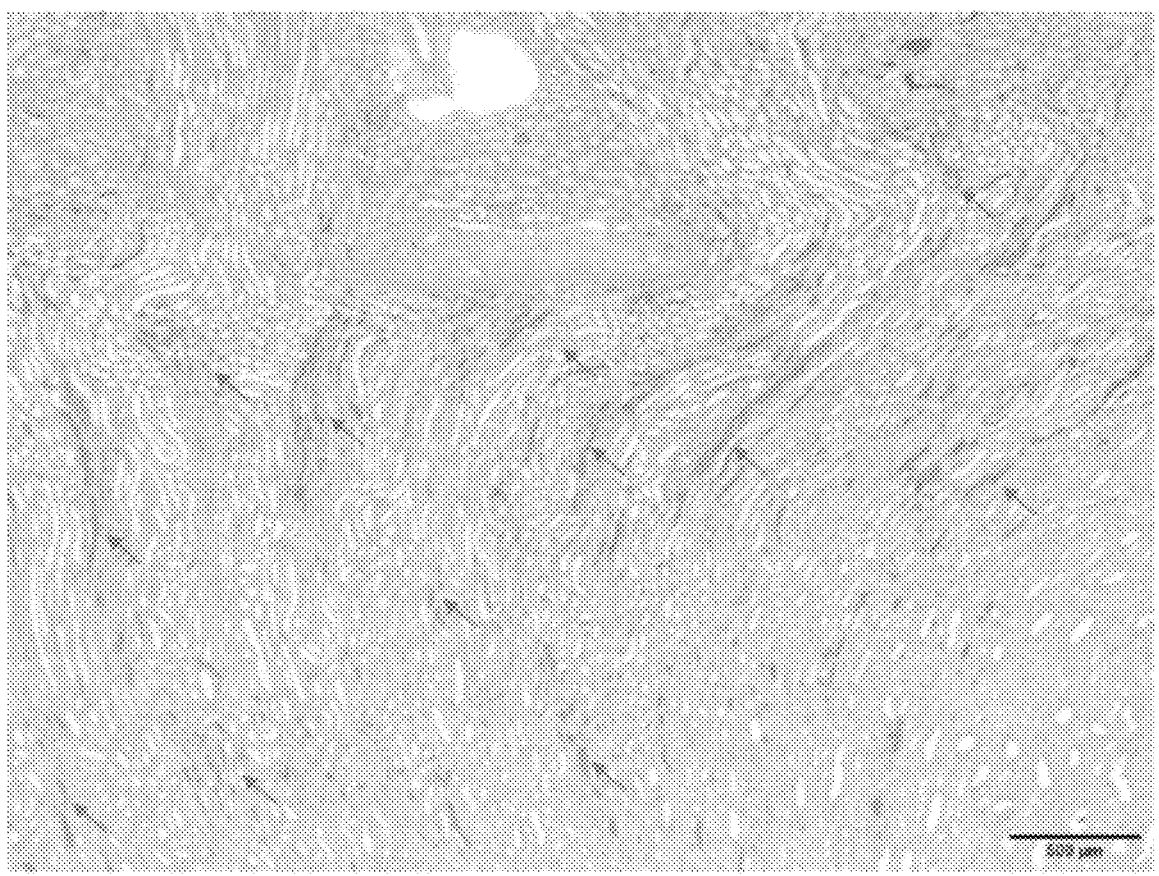
FIG. 19C is a low magnification photomicrograph of kidney tissue from a congested and untreated (e.g., control) kidney.
Figure 19D:
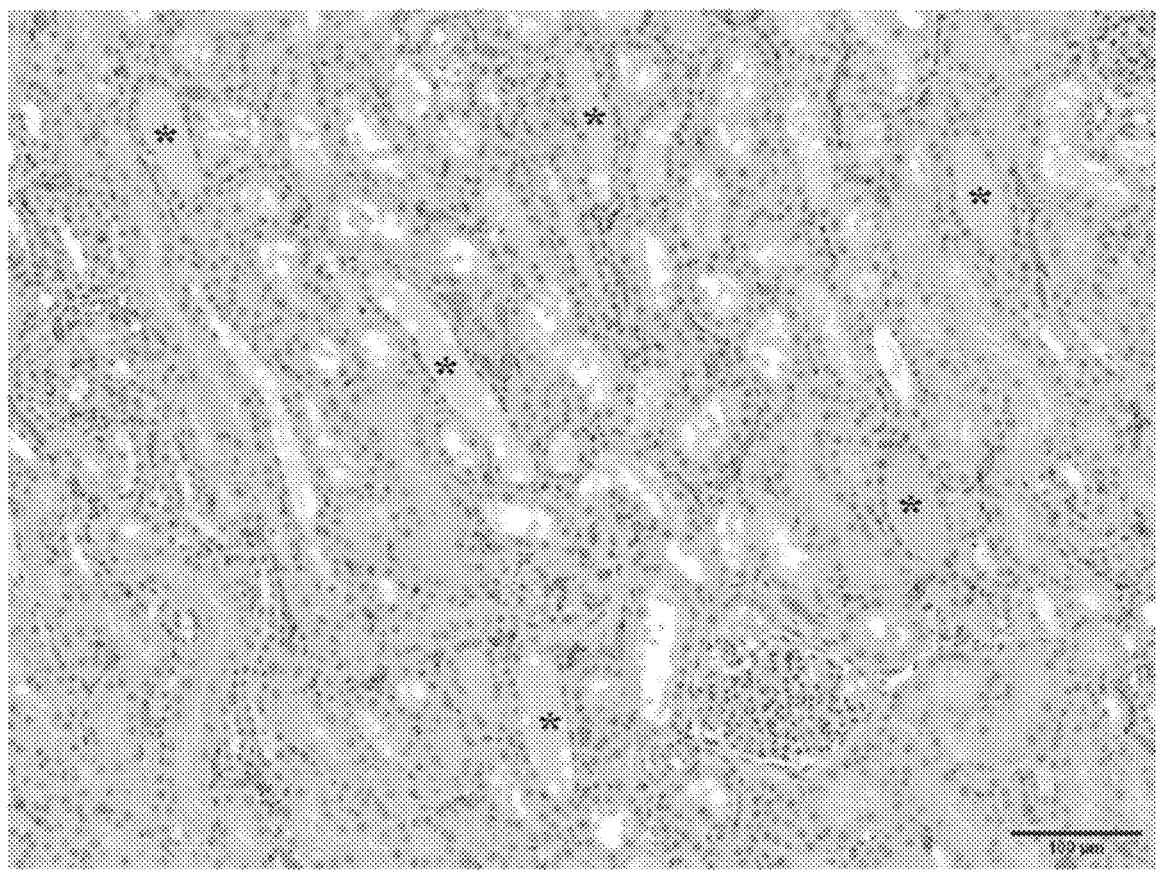
FIG. 19D is a high magnification photomicrograph of the kidney tissue shown in FIG. 19C.

FIGS. 19C and 19D are low and high resolution photomicrographs of the control kidney (right kidney). Based on the histological review, moderate congestion in the blood vessel at the corticomedullary junction was identified, as shown by the arrows in FIG. 19C. As shown in FIG. 19D, several tubules with hyaline casts were present in the tissue sample (as identified by asterisks in the image). Presence of a substantial number of hyaline casts is evidence of hypoxia.

Surface mapping analysis provided the following results. The treated kidney was determined to have 1.5 times greater fluid volume in Bowman's space and 2 times greater fluid volume in tubule lumen. Increased fluid volume in Bowman's space and the tubule lumen corresponds to increased urine output. In addition, the treated kidney was determined to have 5 times less blood volume in capillaries compared to the control kidney. The increased volume in the treated kidney appears to be a result of (1) a decrease in individual capillary size compared to the control and (2) an increase in the number of capillaries without visible red blood cells in the treated kidney compared to the control kidney, an indicator of less congestion in the treated organ.

Summary

These results indicate that the control kidney had more congestion and more tubules with intraluminal hyaline casts, which represent protein-rich intraluminal material, compared to the treated kidney. Accordingly, the treated kidney exhibits a lower degree of loss of renal function. While not intending to be bound by theory, it is believed that as severe congestion develops in the kidney, hypoxemia of the organ follows. Hypoxemia interferes with oxidative phosphorylation within the organ (e.g., ATP production). Loss of ATP and/or a decrease in ATP production inhibits the active transport of proteins causing intraluminal protein content to increase, which manifests as hyaline casts. The number of renal tubules with intraluminal hyaline casts correlates with the degree of loss of renal function. Accordingly, the reduced number of tubules in the treated left kidney is believed to be physiologically significant. While not intending to be bound by theory, it is believed that these results show that damage to the kidney can be prevented or inhibited by applying negative pressure to a catheter inserted into the renal pelvis to facilitate urine output.

Example 2

Method

Inducement of negative pressure within the renal pelvis of farm swine was performed for the purpose of evaluating effects of negative pressure therapy on hemodilution of the blood. An objective of these studies was to demonstrate whether a negative pressure delivered into the renal pelvis significantly increases urine output in a swine model of fluid resuscitation.

Two pigs were sedated and anesthetized using ketamine, midazolam, isoflurane and propofol. One animal (#6543) was treated with a ureteral catheter and negative pressure therapy as described herein. The other, which received a Foley type bladder catheter, served as a control (#6566). Following placement of the catheters, the animals were transferred to a sling and monitored for 24 hours.

Fluid overload was induced in both animals with a constant infusion of saline (125 mL/hour) during the 24 hour follow-up. Urine output volume was measured at 15 minute increments for 24 hours. Blood and urine samples were collected at 4 hour increments. As shown in FIG. 17, a therapy pump 818 was set to induce negative pressure within the renal pelvis 820, 821 (shown in FIG. 17) of both kidneys using a pressure of −45 mmHg (+/−2 mmHg).

Results

Figure 20:
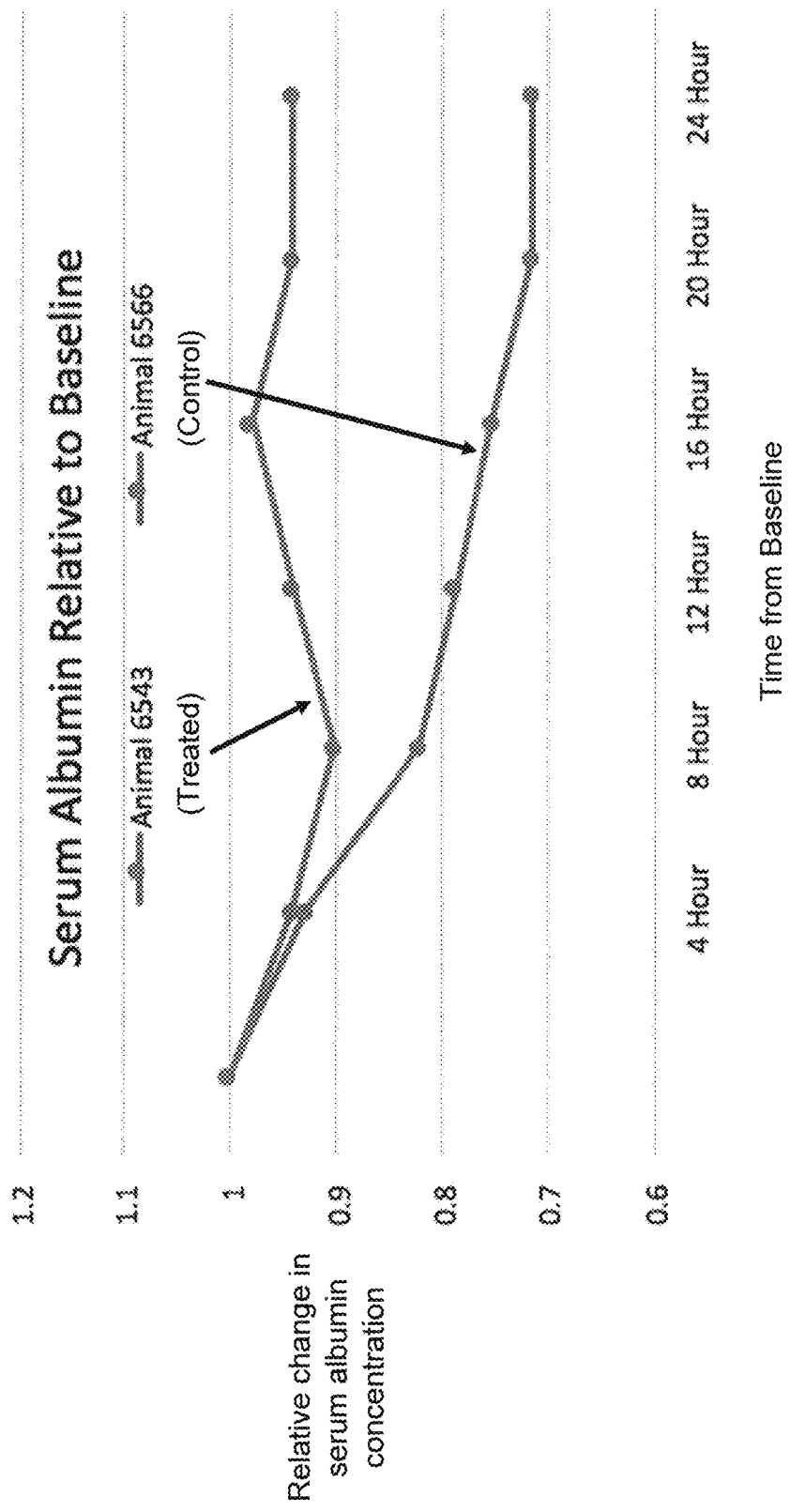
FIG. 20 is a graph of serum albumin relative to baseline for tests conduct on swine using the experimental method described herein.

Both animals received 7 L of saline over the 24 hour period. The treated animal produced 4.22 L of urine while the control produced 2.11 L. At the end of 24 hours, the control had retained 4.94 L of the 7 L administered, while the treated animal retained 2.81 L of the 7 L administered. FIG. 20 illustrates the change in serum albumin. The treated animal had a 6% drop in the serum albumin concentration over 24 hours, while the control animal had a 29% drop.

Summary

While not intending to be bound by theory, it is believed that the collected data supports the hypothesis that fluid overload induces clinically significant impact on renal function and, consequently induces hemodilution. In particular, it was observed that administration of large quantities of intravenous saline cannot be effectively removed by even healthy kidneys. The resulting fluid accumulation leads to hemodilution. The data also appears to support the hypothesis that applying negative pressure diuresis therapy to fluid overloaded animals can increase urine output, improve net fluid balance and decrease the impact of fluid resuscitation on development of hemodilution.

The preceding examples and embodiments of the invention have been described with reference to various examples. Modifications and alterations will occur to others upon reading and understanding the foregoing examples. Accordingly, the foregoing examples are not to be construed as limiting the disclosure.

What is claimed is:

1. A ureteral catheter configured to be deployed in a urinary tract, comprising:
    an elongated tube comprising a proximal portion configured for placement in a ureter, a distal portion comprising a distal end, and a sidewall extending between a proximal end and the distal end of the elongated tube defining at least one drainage lumen extending through the tube; and
    a permeable material directly or indirectly connected to the distal portion of the elongated tube and extending axially and/or radially therefrom, the permeable material being configured to be deployed in the urinary tract to maintain the distal end of the elongated tube at a predetermined position in a ureter, a renal pelvis, or a kidney, wherein the ureteral catheter is free of a balloon,
    wherein, when deployed, the permeable material defines a three-dimensional shape of sufficient size to permit flow of at least a portion of fluid from the urinary tract through the permeable material and drainage lumen of the elongated tube upon application of negative pressure through the catheter, wherein a diameter of a distal portion of the three-dimensional shape of the permeable material is greater than a diameter of a proximal portion of the three-dimensional shape of the permeable material.

2. The catheter of claim 1, wherein, when deployed, the permeable material at least partially encloses the distal end of the elongated tube.

3. The catheter of claim 1, wherein the permeable material comprises at least one of biocompatible polymer fiber(s); metallic fiber(s), porous film(s), film(s) comprising one or more apertures, fabric(s), or any combination thereof.

4. The catheter of claim 1, wherein the permeable material comprises at least one of porous film(s), film(s) comprising one or more apertures, fabric(s), or any combination thereof.

5. The catheter of claim 1, wherein, when deployed in the ureter, renal pelvis, or kidney, the permeable material is configured to maintain a volume of the three dimensional shape when an interior of the ureter, renal pelvis, or kidney is exposed to negative pressure.

6. The catheter of claim 1, wherein, when deployed in the ureter, renal pelvis, or kidney, the permeable material is configured to inhibit tissue of the urinary tract from occluding at least a portion of the distal end of the elongated tube.

7. The catheter of claim 1, wherein, when deployed, the permeable material is configured to inhibit ureteral, renal pelvis or kidney tissue from occluding at least a portion of the expandable retention portion or distal end of the elongated tube upon application of negative pressure through the catheter.

8. The catheter of claim 1, wherein the permeable material comprises a substantially cylindrical distal portion and tapered proximal portion.

9. The catheter of claim 1, wherein the permeable material comprises a plurality of elongated members.

10. The catheter of claim 9, wherein the plurality of elongated members comprises at least one of biocompatible plastic(s), metal(s), biocompatible polymer fiber(s); metallic fiber(s), or any combination thereof.

11. The catheter of claim 9, wherein the plurality of elongated members is directly connected to the distal portion of the elongated tube.

12. The catheter of claim 11, wherein at least one of porous film(s), film(s) comprising one or more apertures, fabric(s), or any combination thereof is connected to the plurality of elongated members.

13. The catheter of claim 1, wherein the sidewall comprises at least one perforation permitting fluid to flow through the sidewall of the elongated tube into the at least one drainage lumen.

14. The catheter of claim 1, wherein, when deployed in the ureter, renal pelvis, or kidney, the permeable material is configured to inhibit any portion of a wall of the ureter, renal pelvis, or kidney from occluding the at least one perforation of the sidewall and/or the distal end of the elongated tube upon delivery of negative pressure to an interior of the ureter, renal pelvis, or kidney through the drainage lumen of the elongated tube.

15. The catheter of claim 1, further comprising at least one collar slidably connected to the elongated tube, wherein at least a portion of the permeable material is connected to the collar, wherein sliding the collar along the elongated tube deploys or retracts the permeable material.

16. The catheter of claim 1, wherein the ureteral catheter is configured to be deployed in a urinary tract of a patient, wherein the patient is a human.

17. A system for drawing urine from a urinary tract, the system comprising:
    a ureteral catheter comprising:
        an elongated tube comprising a proximal portion configured for placement in a ureter, renal pelvis, or kidney, a distal portion comprising a distal end, and a sidewall extending between a proximal end and the distal end of the elongated tube defining at least one drainage lumen extending through the tube; and
        a permeable material directly or indirectly connected to the distal portion of the elongated tube and extending axially and/or radially therefrom, the permeable material being configured to be deployed in the urinary tract to maintain the distal end of the elongated tube at a predetermined position in a ureter, a renal pelvis, or a kidney, wherein, when deployed, the permeable material defines a three-dimensional shape of sufficient size to permit flow of at least a portion of fluid from the urinary tract through the permeable material and the at least one drainage lumen extending through the elongated tube, wherein a diameter of a distal portion of the three-dimensional shape of the permeable material is greater than a diameter of a proximal portion of the three-dimensional shape of the permeable material wherein the ureteral catheter is free of a balloon; and
    a pump in fluid connection with the drainage lumen of the elongated tube, wherein the pump is configured to introduce negative pressure through the drainage lumen to the urinary tract to draw urine from the urinary tract.

18. The system of claim 17, wherein the sidewall comprises at least one perforation permitting fluid to flow through the sidewall of the elongated tube into the at least one drainage lumen.

19. The system of claim 18, wherein, when deployed in the ureter, renal pelvis, or kidney, the permeable material is configured to inhibit any portion of a wall of the ureter, renal pelvis, or kidney from occluding the at least one perforation of the sidewall and/or the distal end of the elongated tube upon delivery of negative pressure to an interior of the ureter, renal pelvis, or kidney through the drainage lumen of the elongated tube.

20. The system of claim 17, wherein the permeable material is configured to be deployed in a urinary tract of a patient, wherein the patient is a human.

21. A method of inducing a negative pressure in a urinary tract for enhancing urine excretion therefrom, the method comprising:

inserting a distal portion of an elongated tube of a ureteral catheter into the urinary tract, the elongated tube comprising a proximal portion configured for placement in a ureter, a distal portion comprising a distal end, and a sidewall extending between a proximal end and the distal end of the elongated tube defining at least one drainage lumen extending through the tube;

deploying a permeable material directly or indirectly connected to and extending axially and/or radially from the elongated tube at a predetermined position in a ureter, a renal pelvis, or a kidney, wherein the permeable material is configured to be deployed in the urinary tract to maintain the distal end of the elongated tube at the predetermined position, and wherein, when deployed, the permeable material defines a three-dimensional shape of sufficient size to permit flow of at least a portion of fluid from the urinary tract through the permeable material and the at least one drainage lumen extending through the elongated tube upon application of negative pressure through the catheter, wherein a diameter of a distal portion of the three-dimensional shape of the permeable material is greater than a diameter of a proximal portion of the three-dimensional shape of the permeable material, wherein the ureteral catheter is free of a balloon; and inducing a negative pressure through the at least one drainage lumen of the elongated tube to draw urine from the urinary tract into the drainage lumen.

22. The method of claim 21, wherein the permeable material is deployed in a urinary tract of a patient, wherein the patient is a human.

* * * * *